(12) United States Patent
Luscher et al.

(10) Patent No.: US 10,465,163 B2
(45) Date of Patent: Nov. 5, 2019

(54) METHODS, SYSTEMS, AND APPARATUS FOR PERFORMING FLOW CYTOMETRY

(71) Applicant: MICROBIX BIOSYSTEMS INC., Mississauga (CA)

(72) Inventors: Mark Luscher, Toronto (CA); Randall Marks, San Jose, CA (US)

(73) Assignee: MICROBIX BIOSYSTEMS INC., Mississauga (CA)

( * ) Notice: Subject to any disclaimer, the term of this patent is extended or adjusted under 35 U.S.C. 154(b) by 455 days.

(21) Appl. No.: 15/419,830

(22) Filed: Jan. 30, 2017

(65) Prior Publication Data

US 2017/0137780 A1 May 18, 2017

Related U.S. Application Data

(63) Continuation of application No. 13/985,859, filed as application No. PCT/US2012/025176 on Feb. 15, 2012, now Pat. No. 9,556,416.

(Continued)

(51) Int. Cl.
*G01N 15/14* (2006.01)
*C12N 5/071* (2010.01)
(Continued)

(52) U.S. Cl.
CPC ........... *C12N 5/0612* (2013.01); *C12N 5/061* (2013.01); *G01N 15/1404* (2013.01);
(Continued)

(58) Field of Classification Search
None
See application file for complete search history.

(56) References Cited

U.S. PATENT DOCUMENTS 2,656,508 A    10/1953 Coulter
3,380,584 A    4/1968 Fulwyler
(Continued)

FOREIGN PATENT DOCUMENTS

CA    2045287 A1    12/1992
DE    1815352 A1    1/1971
(Continued)

OTHER PUBLICATIONS

International Preliminary Report on Patentability and Written Opinion for International Application No. PCT/US2012/025176, dated Aug. 21, 2013.

(Continued)

*Primary Examiner* — Neil N Turk
(74) *Attorney, Agent, or Firm* — Marshall, Gerstein & Borun LLP

(57) ABSTRACT

An apparatus for identifying analytes of a first type in a fluid sample having a plurality of types includes a closed flow cell. The flow cell includes a sample inlet, a sample outlet. A flow path, between the inlet and outlet, passing through an interrogation region and at least a portion extending from immediately upstream to immediately downstream of the interrogation region is bounded by a flow cell well to form a continuous closed flow path. The apparatus also includes a spherical element having a center point coincident with the interrogation region. A hydrodynamic focusing element upstream of the interrogation region creates a core-in-sheath flow along a flow axis of the flow path as it passes through the interrogation region. Further, the apparatus includes a concave, ellipsoidal collector element having a first focal point disposed in the interrogation region of the flow path. A plurality of beams of electromagnetic energy converge non-axisymmetrically at the interrogation region, each of the plurality of beams orthogonal to the flow axis.

9 Claims, 33 Drawing Sheets

Related U.S. Application Data

(60) Provisional application No. 61/482,504, filed on May 4, 2011, provisional application No. 61/443,178, filed on Feb. 15, 2011, provisional application No. 61/443,174, filed on Feb. 15, 2011.

(51) Int. Cl.

| | | |
|---|---|---|
| *C12N 5/076* | (2010.01) | |
| *G01N 33/487* | (2006.01) | |
| *G01N 33/49* | (2006.01) | |
| G01N 33/48 | (2006.01) | |
| G01N 15/00 | (2006.01) | |
| G01N 15/10 | (2006.01) | |

(52) U.S. Cl.
CPC ....... *G01N 15/147* (2013.01); *G01N 15/1434* (2013.01); *G01N 15/1436* (2013.01); *G01N 15/1459* (2013.01); *G01N 33/487* (2013.01); *G01N 33/4915* (2013.01); G01N 2015/0065 (2013.01); G01N 2015/1006 (2013.01); G01N 2015/149 (2013.01)

(56) References Cited

U.S. PATENT DOCUMENTS

| | | |
|---|---|---|
| 3,497,690 A | 2/1970 | Wheeless, Jr. et al. |
| 3,529,896 A | 9/1970 | Padawer |
| 3,657,537 A | 4/1972 | Wheeless, Jr. et al. |
| 3,710,933 A | 1/1973 | Fulwyler et al. |
| 3,954,341 A | 5/1976 | Uffenheimer |
| 4,021,117 A | 5/1977 | Gohde et al. |
| 4,188,542 A | 2/1980 | Hogg et al. |
| 4,284,355 A | 8/1981 | Hansen et al. |
| 4,395,397 A | 7/1983 | Shapiro |
| 4,606,636 A | 8/1986 | Monin et al. |
| 4,629,687 A | 12/1986 | Schindler et al. |
| 4,998,022 A | 3/1991 | Tregay |
| 5,135,759 A | 8/1992 | Johnson |
| 5,153,679 A | 10/1992 | Gilby |
| 5,158,889 A | 10/1992 | Hirako et al. |
| 5,184,192 A | 2/1993 | Gilby et al. |
| 5,406,421 A | 4/1995 | Kashima et al. |
| 5,495,105 A | 2/1996 | Nishimura et al. |
| 5,544,182 A | 8/1996 | Nagaishi et al. |
| 5,608,517 A | 3/1997 | Munk |
| 5,650,847 A | 7/1997 | Maltsev et al. |
| 5,658,892 A | 8/1997 | Flotte et al. |
| 5,739,902 A | 4/1998 | Gjelsnes et al. |
| 6,010,647 A | 1/2000 | Nomura et al. |
| 6,143,535 A | 11/2000 | Palsson |
| 6,245,508 B1 | 6/2001 | Heller et al. |
| 6,320,705 B1 | 11/2001 | Dube' |
| 6,388,746 B1 | 5/2002 | Eriksson et al. |
| 6,473,238 B1 | 10/2002 | Daniell |
| 6,534,308 B1 | 3/2003 | Palsson et al. |
| 6,594,009 B2 | 7/2003 | Saccomanno |
| 6,797,139 B2 | 9/2004 | Bahatt et al. |
| 6,816,182 B2 | 11/2004 | Kubota et al. |
| 7,106,528 B2 | 9/2006 | Ohmori et al. |
| 7,118,676 B2 | 10/2006 | Mueth et al. |
| 7,193,775 B2 | 3/2007 | Olszak et al. |
| 7,355,696 B2 | 4/2008 | Mueth et al. |
| 7,403,125 B2 | 7/2008 | Rich |
| 7,586,604 B2 | 9/2009 | Sharpe et al. |
| 8,004,661 B2 | 8/2011 | Luscher |
| 2002/0096123 A1 | 7/2002 | Whittier et al. |
| 2002/0125230 A1 | 9/2002 | Haight et al. |
| 2003/0087860 A1 | 5/2003 | Mileham et al. |
| 2003/0137661 A1 | 7/2003 | Ortyn et al. |
| 2003/0180955 A1 | 9/2003 | Ozasa et al. |
| 2004/0012676 A1 | 1/2004 | Weiner et al. |
| 2004/0189977 A1 | 9/2004 | Nagai et al. |
| 2005/0019842 A1 | 1/2005 | Prober et al. |
| 2005/0110996 A1 | 5/2005 | Sharpe et al. |
| 2005/0112541 A1 | 5/2005 | Durack et al. |
| 2005/0194546 A1 | 9/2005 | Saccomanno |
| 2006/0170912 A1 | 8/2006 | Mueth et al. |
| 2006/0192940 A1 | 8/2006 | Phi-Wilson |
| 2006/0203226 A1 | 9/2006 | Roche et al. |
| 2006/0263829 A1 | 11/2006 | Evans et al. |
| 2007/0047868 A1 | 3/2007 | Beaulieu et al. |
| 2007/0117086 A1 | 5/2007 | Evans et al. |
| 2007/0215817 A1 | 9/2007 | Shirai et al. |
| 2008/0094627 A1 | 4/2008 | Oldham et al. |
| 2008/0144037 A1 | 6/2008 | Mueth et al. |
| 2008/0213915 A1 | 9/2008 | Durack et al. |
| 2008/0268469 A1 | 10/2008 | Srienc et al. |
| 2009/0116011 A1 | 5/2009 | Kenyon |
| 2009/0325217 A1 | 12/2009 | Luscher |
| 2010/0047761 A1 | 2/2010 | MacDonald et al. |
| 2010/0284016 A1 | 11/2010 | Teitell et al. |
| 2011/0089315 A1 | 4/2011 | Walt et al. |
| 2011/0165025 A1 | 7/2011 | Gransee et al. |

FOREIGN PATENT DOCUMENTS

| | | |
|---|---|---|
| EP | 1365237 A1 | 11/2003 |
| EP | 2264428 A2 | 12/2010 |
| GB | 2403289 A | 12/2004 |
| WO | WO-94/22001 A1 | 9/1994 |
| WO | WO-98/34094 A1 | 8/1998 |
| WO | WO-99/05504 A2 | 2/1999 |
| WO | WO-01/29538 A1 | 4/2001 |
| WO | WO-02/059273 A2 | 8/2002 |
| WO | WO-2004/017041 A2 | 2/2004 |
| WO | WO-2004/088283 A2 | 10/2004 |
| WO | WO-2004/104178 A2 | 12/2004 |
| WO | WO-2005/075629 A1 | 8/2005 |
| WO | WO-2008/128630 A1 | 10/2008 |
| WO | WO-2009002537 A1 | 12/2008 |
| WO | WO-2009/014643 A1 | 1/2009 |
| WO | WO-2009/151624 A1 | 12/2009 |
| WO | WO-2010/001254 A2 | 1/2010 |
| WO | WO-2010/0007880 A1 | 1/2010 |

OTHER PUBLICATIONS

Patent Examination Report No. 1 issued in Australian Patent Application No. 2012217757 dated Nov. 27, 2014.
First Examination Report issued in New Zealand Patent Application No. 614034 dated Mar. 24, 2014.
Further Examination Report issued in New Zealand Patent Application No. 614034 dated Dec. 3, 2014.
Examination Report issued in Pakistan Patent Application No. 95/2012 dated Oct. 22, 2013.
International Search Report issued in PCT/US2012/025176 dated May 29, 2012.
Abramowitz, et al., "Molecular Expressions Optical Microscopy Primer Anatomy of the Microscope," The Florida State University, Downloaded from http://micro.magnet.fsu.edu/primer/anatomy/kohler.html on Jun. 8, 2009 (Last modified 2003).
Abramowitz, et al., "Molecular Expressions Optical Microscopy Primer Specialized Techniques," The Florida State University, Downloaded from http://micro.magnet.fsu.edu/primer/techiques/oblique/obliqueintro.html on Jun. 8, 2009 (Last modified 2003).
Bakker Schut, et al., "A New Principle of Cell Sorting by Using Selective Electroporation in a Modified Flow Cytometer," Cytometry, vol. 11, pp. 659-666 (1990).
Balak, et al., "Regenerated Hair Cells Can Originate from Supporting Cell Progeny: Evidence from Phototoxicity and Laser Ablation Experiments in the Lateral Line System," The Journal of Neuroscience, vol. 10, No. 8, pp. 2502-2512 (1990).
Brenner, et al., "Water Immersion Objectives," Nikon Instruments, Inc., Available at http://www.microscopyu.com/articles/optics/waterimmersionobjectives.html (date unknown, accessed Apr. 23, 2009).
Crosland-Taylor, "A Device for Counting Small Particles suspended in a Fluid through a Tube," Nature, vol. 171, pp. 37-38 (1953).

(56) References Cited

OTHER PUBLICATIONS

Cytop®, "Amorphous Fluorocarbon Polymer," (undated) Available at http://www.belexinternational.com/Cytopflyer.pdf.
Dilla, et al., "Cell Microfluorometry: A Method for Rapid Fluorescence Measurement," Science, New Series, vol. 163, No. 3872, pp. 1213-1214 (1969).
Egner, et al., "Aberrations in Confocal and Multi-Photon Fluorescence Microscopy Induced by Refractive Index Mismatch," Handbook of Biological Confocal Microscopy, third edition, (2006).
Evenson, et al., "Comparative Sperm Chromatin Structure Assay Measurements on Epiillumination and Orthogonal Axes Flow Cytometers," Cytometry, vol. 19, pp. 295-303 (1995).
Fulwyler, "Electronic Separation of Biological Cells by Volume," Science, New Series, vol. 150, No. 3698, pp. 910-911 (1965).
Fulwyler, "Hydrodynamic Orientation of Cells," The Journal of Histochemistry and Cytochemistry, vol. 25, No. 7, pp. 781-783 (1977).
Garner, et al., "Quantification of the X- and Y-Chromosome-Bearing Spermatozoa of Domestic Animals by Flow Cytometry," Biology of Reproduction 28, pp. 312-321 (1983).
Gledhill, "Cytometry of Mammalian Sperm," Gamete Research, vol. 12, pp. 423-438 (1985).
Gledhill, et al., "Flow Microfluorometric Analysis of Sperm DNA Content: Effect of Cell Shape on the Fluorescence Distribution," J. Cell. Physiol., vol. 87, pp. 367-376 (1975).
H.M. Shapiro, "Practical Flow Cytometry," John Wiley & Sons, Inc., Available at http://dx.doi.org/10.1002/0471722731.ch8, pp. 266-267 (2003).
He, et al., "Targeted photoporation and transfection in human HepG2 cells by a fiber femtosecond laser at 1554 nm," Optics Letters, vol. 33, No. 24, pp. 2961-2963 (2008).
Herweijer, et al., "High-Speed Photodamage Cell Selection Using Bromodeoxyuridine/Hoechst 33342 Photosensitized Cell Killing," Cytometry vol. 9, pp. 143-149 (1988).
Hung, et al., "Fluorinated Plastics, Amorphous," Concise Polymer Materials Encyclopedia, pp. 499-501 (1998).
Kang, et al., "Cancer-Cell Targeting and Photoacoustic Therapy Using Carbon Nanotubes as "Bomb" Agents," Carbon Nanobtubes for Photoacoustic Cancer Therapy, Small 2009, Available at http://www.smalljournal.com (2009).
Kashima, "Development of Laser Scanning Microscopy Using a Near Ultraviolet Laser," Scanning, vol. 17, pp. 66-69 (1995).
Kawano, et al., "Ultrafast dynamics in a live cell irradiated by femtosecond laser pulses," Biophotonics 2007: Optics in Life Science, edited by Jürgen Popp, Gert von Bally, Proc. of SPIE-OSA Biomedical Optics, SPIE vol. 6633, pp. 66330J-1-66330J-9(2007).
Keij, et al., "Coincidence in High-Speed Flow Cytometry: Models and Measurements," Cytometry, vol. 12, pp. 398-404 (1991).
Keij, et al., "High-Speed Photodamage Cell Selection Using a Frequency-Doubled Argon Ion Laser," Cytometry, vol. 19, pp. 209-216 (1995).
Keij, et al., "High-Speed Photodamage Cell Sorting: An Evaluation of the ZAPPER Prototype," Methods in Cell Biology, vol. 42, pp. 371-386 (1994).
Kerker, et al., "An Optical Model for Fluorescence of Mammalian Sperm in Flow Cytometry," Cytometry vol. 1, No. 2, pp. 161-167 (1980).
Keu, et al., "Reduced Photoinactivation of 10-Dodecyl Acridine Orange-Sensitized Yeast Cells at High Fluence Rates: Measurements and Computer Simulations," Photochemistry and Photobiology, vol. 60, No. 5, pp. 503-509, (1994).
Koller, et al., "High-Throughput Laser-Mediated In Situ Cell Purification with High Purity and Yield," Cytometry Part A, vol. 61A, pp. 153-161 (2004).
König, et al., "Effects of ultraviolet exposure and near infrared laser tweezers on human spermatozoa," Human Reproduction vol. 11 No. 10, pp. 2162-2164 (1996).
Lapotko, et al., "Spectral Evaluation of Laser-Induced Cell Damage with Photothermal Microscopy," Lasers in Surgery and Medicine, vol. 36, pp. 22-30 (2005).
Lee, et al., "Optical detection of intracellular cavitation during selective laser targeting of the retinal pigment epithelium: dependence of cell death mechanism on pulse duration," Journal of Biomedical Optics, vol. 12, No. 6, pp. 064034-1-064034-14 (2007).
M. Li, "POFnet TM, Plastic Optical Fiber (POF) The Last Few Hundred Meters," Hakko Optical, (2007).
Martin, et al., "Photodamage, a Basis for Super High Speed Cell Selection," Cytometry vol. 2, p. 2 (Abstract) (1981).
Meistrich, et al., "Resolution of X and Y spermatids by pulse cytophotometry," Nature, vol. 274, pp. 290-291 (1978).
Merrill, et al. "An Improved Cell Volume Analyzer," The Review of Scientific Instruments, vol. 42, No. 8, pp. 1157-1163 (1971).
Mir, et al., "Two-photon absorption of copper tetrasulfophthalocyanine induces phototoxicity towards Jurkat cells in vitro," Photochemical and Photobiological Sciences, vol. 5, pp. 1024-1030 (2006).
Mullaney, et al., "Cell Sizing: A Light Scattering Photometer for Rapid Volume Determination," The Review of Scientific Instruments, vol. 40, No. 8, pp. 1029-1032 (1969).
Oldfield, "Light Microscopy: An Illustrated Guide," A Mosby Ltd., p. 160 (1993).
Otto, et al., "Flow Cytometry of Human Spermatozoa," Histochemistry 62, pp. 249-254 (1979).
PHYWE, Impulscytophotometrie ICP 22 Datasheet (1976).
PHYWE, Impulscytophotometrie ICP11 Book, pp. 1-24 (1973).
Pinkel, et al., "Flow Cytometric Determination of the Proportions of X-andY-Chromosome-Bearing Sperm in Samples of Purportedly Separated Bull Sperm," Journal of Animal Science 60:1303-1307, (1985).
Pinkel, et al., "High Resolution DNA Content Measurements of Mammalian Sperm," Cytometry vol. 3, No. 1, pp. 1-9 (1982).
Pinkel, et al., "Sex Preselection in Mammals? Separation of Sperm Bearing Y and "O" Chromosomes in the Vole Microtus oregoni," Science, vol. 218, pp. 904-906 (1982).
Pitsillides, et al., "Selective Cell Targeting with Light-Absorbing Microparticles and Nanoparticles,"Biophysical Journal, vol. 84, pp. 4023-4032 (2003).
Roegener, et al., "Pump-probe detection of laser-induced microbubble formation in retinal pigment epithelium cells," Journal of Biomedical Optics, vol. 9, No. 2, pp. 367-371 (2004).
Sarkar, et al., "Constancy in Human Sperm DNA Content," Proceedings of the National Academy of Sciences, vol. 71, No. 9, pp. 2512-3516 (1974).
Severin, et al., "A New Flow Chamber and Processing Electronics for Combined Laser and Mercury Arc Illumination in an Impulscytophotometer Flow Cytometer," Cytometry, vol. 3, No. 4, pp. 308-310 (1983).
Sharpe, et al., "Radially Symmetric Excitation and Collection Optics for Flow Cytometric Sorting of Aspherical Cells," Cytometry, vol. 29, pp. 363-370 (1997).
Steinkamp, et al., "A New Multiparameter Separator for Microscopic Particles and Biological Cells," Rev. Sci. Instrum., vol. 44, No. 9, pp. 1301-1310 (1973).
Steinkamp, et al., "Dual-Laser Flow Cytometry of Single Mammalian Cells," The Journal of Histochemistry and Cytochemistry, vol. 27, No. 1, pp. 273-276 (1979).
Takahahi, et al., "Further advancement of wide-angle EUSO telescope with holographic and Fresnel lenses," 29th International Cosmic Ray Conference Pune 8, pp. 355-358 (2005).
Takizawa, et al., "Advancement of the wide-angle JEM-EUSO optical system with holographic and Fresnel lenses," 30th International Cosmic Ray Conference ICRC 2007 Proceedings—Pre-Conference Edition (2007).
Tanabe, et al., "Multiphoton excitation-evoked chromophore-assisted laser inactivation using green fluorescent protein," Natural Methods, vol. 2, No. 7, pp. 503-505 (2005).
Thøgersen, et al., "Reproductive death of cancer cells induced by femtosecond laser pulses," Int. J. Radiat. Biol., vol. 83, No. 5, pp. 289-299 (2007).
Tirlapur, et al., "Targeted transfection by femtosecond laser," Nature, vol. 418, pp. 290-291 (2002).
Van Dilla, et al., "Measurement of Mammalian Sperm Deoxyribonucleic Acid by Flow Cytometry," The Journal of Histochemistry and Cytochemistry, vol. 25, No. 7, pp. 763-773 (1977).

(56) References Cited

OTHER PUBLICATIONS

Vogel, et al., "Femtosecond Plasma-Mediated Nanosurgery of Cells and Tissues," Laser Ablation and its Applications, pp. 231-280 (2007).
White, et al., "Manufacture of Perfluorinated Plastic Optical Fibers," Optical Fiber Communication Conference, Available at http://ieeexplore.ieee.org/xpl/freeabs_all.jsp?arnumber=1362102 (2004).
Zohdy, et al., "Acoustic Estimation of Thermal Distribution in the Vicinity of Femtosecond Laser-Induced Optical Breakdown," IEEE Transactions on Biomedical Engineering, vol. 53, No. 11, pp. 2347-2355 (2006).
Zohdy, et al., "Optical and Acoustic Detection of Laser-Generated Microbubbles in Single Cells," IEEE Transactions on Ultrasonics, Ferroelectrics, and Frequency Control, vol. 52, No. 1, pp. 117-125 (2006).
International Search Report and Written Opinion for Application No. PCT/IB2009/006480, dated Feb. 16, 2010.
Asbury, et al., "Polarization of Scatter and Fluorescence Signals in Flow Cytometry," Cytometry vol. 40 pp. 88-101 (2000).
Fouque, et al., "Multiple wavelength fluorescence enhancement on glass substrates for biochip and cell analyses," Biosensors an Bioelectronics vol. 20 pp. 2335-2340 (2005).
Kummrow, et al., "Microfluidic structures for flow cytometric analysis of hydrodynamically focussed blood cells fabricated by ultraprecision micromachining," The Royal Society of Chemistry vol. 9 pp. 972-981(1999).
Seitzinger, et al., "Ray tracing analysis of the image quality of a high collection efficiency mirror system," Applied Optics vol. 29, No. 28 (1990).
Gledhill et al., "Flow Cytometry and Sorting of Sperm and Male Germ Cells," Flow Cytometry and Sorting Wiley-Liss, (1990) pp. 531-551.
An-Shik Yang et al., "Hydrodynamic Focusing Investigation in a Micro-Flow Cytometer," 9 Biomedical Microdevices 113, 113 (Apr. 2007).
John Sharpe, Flow Cytometry Instrumentation, in Flow Cytometry Educational Guide 2d. Ed., 9 (Dako, 2006).
Howard M. Shapiro, Practical Flow Cytometry (Wiley-Liss, 4th ed. 2003).
Flow Cytometry (Michael G. Ormerod ed., Oxford 3d ed., 2000).
Hercher et al., "Detection and Discrimination of Individual Viruses by Flow Cytometry," 27 Journal of Histochemistry and Cytochemistry pp. 350-352 (1979).
BD FACSCanto II Flow Cytometry Reference Manual, Becton Dickinson and Company (2006).
Johnson, et al., "Flow Sorting of X and Y Chromosome-Bearing Spermatozoa into Two Populations," Gamette Research 16 (1987) pp. 1-9.
Claim Chart Applying Cited Art to All Claims for Which Reexamination is Requested Under 37 C.F.R. 1915(b), Request for Ex Parte Reexamination of U.S. Pat. No. 8,004,661 (Control No. 90/009,985, filed Feb. 13, 2012).
Declaration of Daniel Pinkel, Ph.D., filed with Request for Inter-Partes Reexamination of U.S. Pat. No. 8,004,661 (Control No. 95/000,643, filed Aug. 30, 2011).
Declaration of John Sharpe, Ph.D., filed with Request for Ex Parte Reexamination of U.S. Pat. No. 8,004,661 (Control No. 90/009,985, filed Feb. 13, 2012).
Decision Granting Inter Partes Reexamination of U.S. Pat. No. 8,004,661 (Control No. 95/000,643, filed Dec. 15, 2011).
Office Action in Inter Partes Reexamination of U.S. Pat. No. 8,004,661 (Control No. 95/000,643, filed Dec. 15, 2011).
Lindmo et al., "Flow Sorters for Biological Cells," Flow Cytometry and Sorting 145 (Melamed et al., eds., Wiley-Liss 1990).
Johnson et al., "Sex Preselection in Rabbits: Live Births from X and Y Sperm Separated by DNA and Cell Sorting," Biology of Reproduction 41, pp. 199-203 (1989).
Notice of Allowance (dated Jun. 8, 2011) for U.S. Appl. No. 12/495,406.
Beisker et al., "Double Beam Autocompensation for Fluorescence Polarization Measurements in Flow Cytometry," J. Biophys. vol. 47 (1985) pp. 607-612.
Request for Inter-Partes Reexamination of U.S. Pat. No. 8,004,661 (Control No. 95/000,643, filed Aug. 30, 2011).
Request for Ex Parte Reexamination of U.S. Pat. No. 8,004,661 (Control No. 90/009,985, filed Feb. 13, 2012).
Office Action for U.S. Appl. No. 12/495,437 dated Nov. 14, 2011.
Johnson, et al., *Flow Sorting of X and Y Chromosome-Bearing Spermatozoa Into Two Populations*, Gamete Research 16:1-9 (1987).
Declaration of J. Paul Robinson, Ph.D.
Response to Office Action dated Jul. 13, 2012 in Ex Parte Reexamination of U.S. Pat. No. 8,004,661 filed Sep. 13, 2012.
Chinese Office Action issued in Chinese Pat. Appl. No. 201280009586.7 dated Dec. 22, 2014.
Second Official Office Action for Mexican Patent Application No. <X/a/2013/009377, dated Apr. 15, 2015.
Examination Report issued in New Zealand Pat. Appl. No. 706531 dated Nov. 26, 2015.
Office Action issued in Mexican Patent Application No. A/2013/009377 dated Oct. 29, 2015.
Chinese Office Action issued in Chinese Patent Application No. 201280009586.7 dated Nov. 11, 2015.
Chinese Office Action issued in Application No. 2012800095867 dated May 3, 2016.
Office Action issued in Colombian Patent Application No. 14-268193 dated Jun. 27, 2016.
Office Action issued in Canadian Patent Application No. 2,826,914 dated May 27, 2016.
Office Action issued in New Zealand Patent Application No. 706531 dated May 5, 2016.
Office Action issued in Chinese Patent Application No. 201280009586.7 dated Dec. 18, 2018.
Examination Report issued in Indian Patent Application No. 6408/CHENP/2013 dated Aug. 28, 2018.
Office Action issued in Canadian Patent Application No. 2,991,625 dated Nov. 16, 2018.
Mollet et al., "Computer Simulations of the Energy Dissipation Rate in a Fluorescence-Activated Cell Sorter: Implications to Cells," *Department of Chemical and Biomolecular Engineering*, (2007).

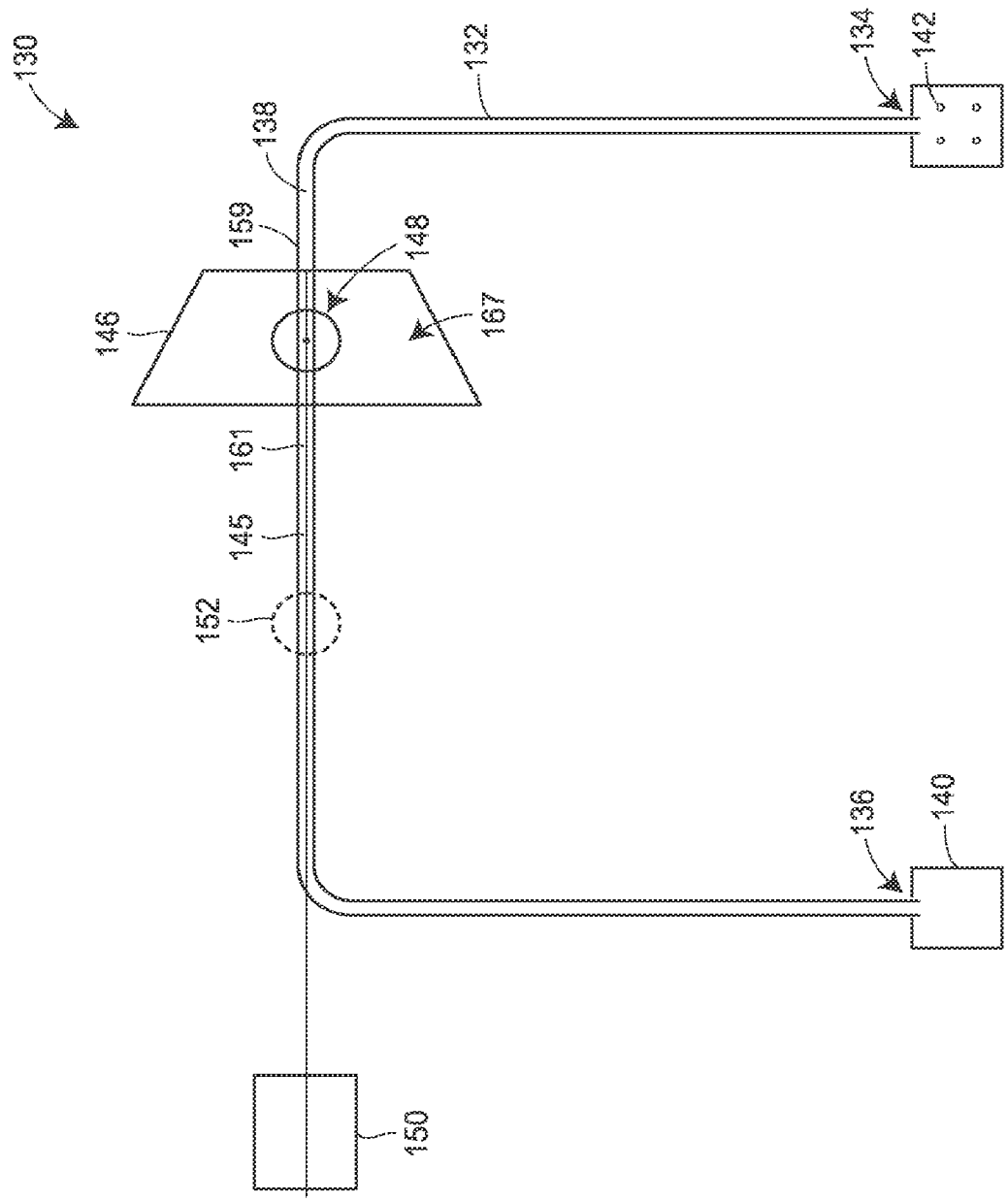

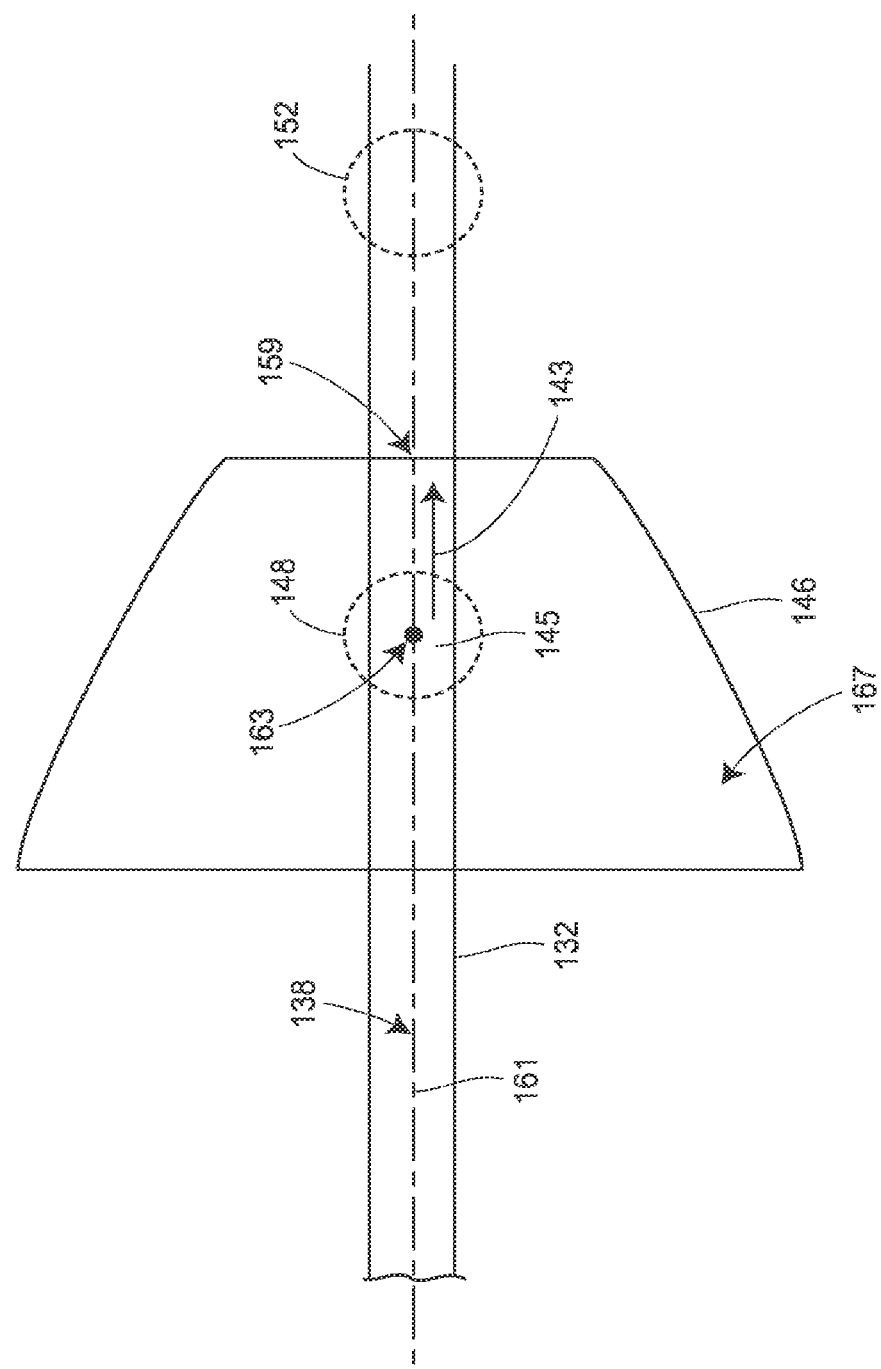

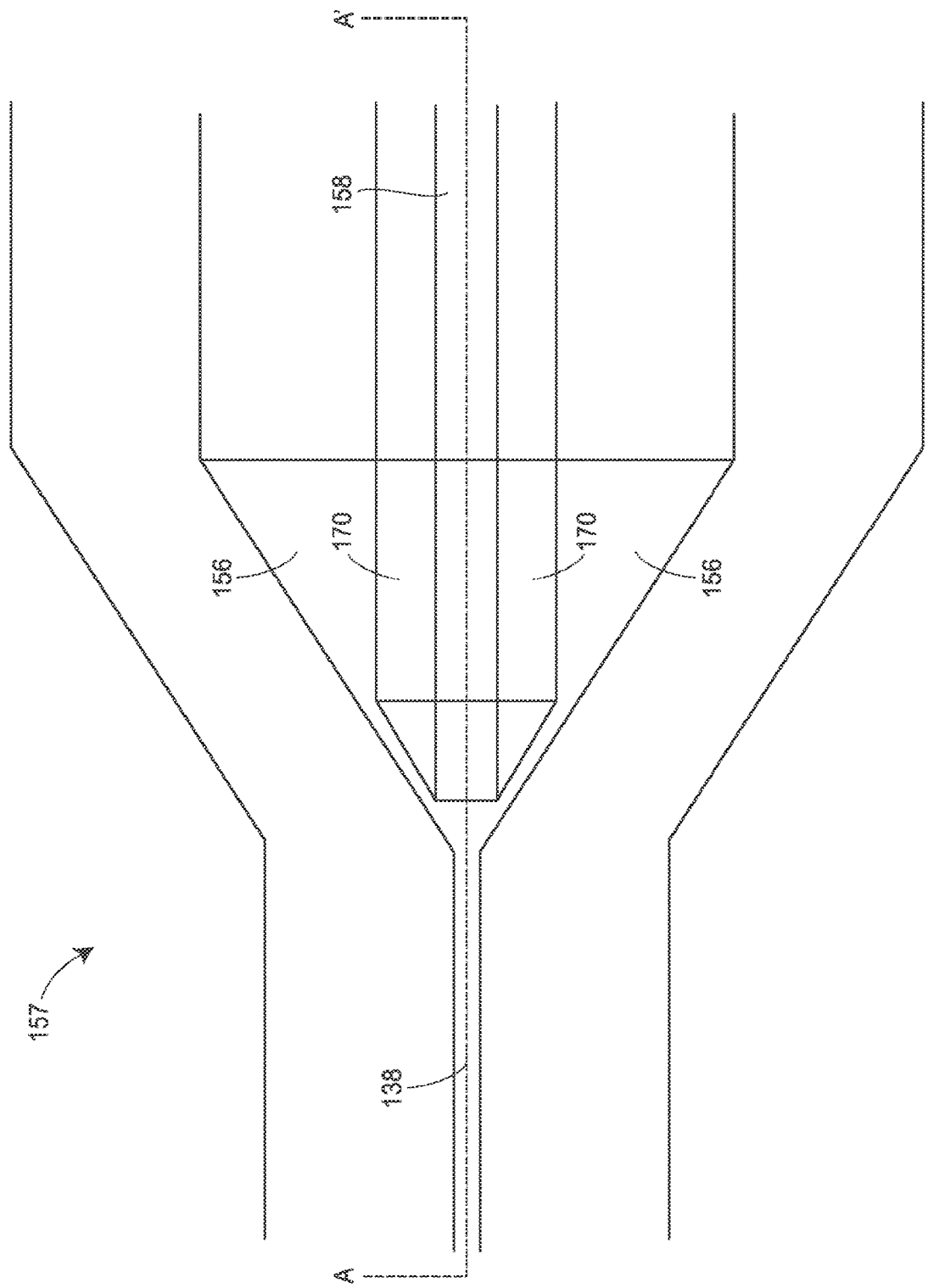

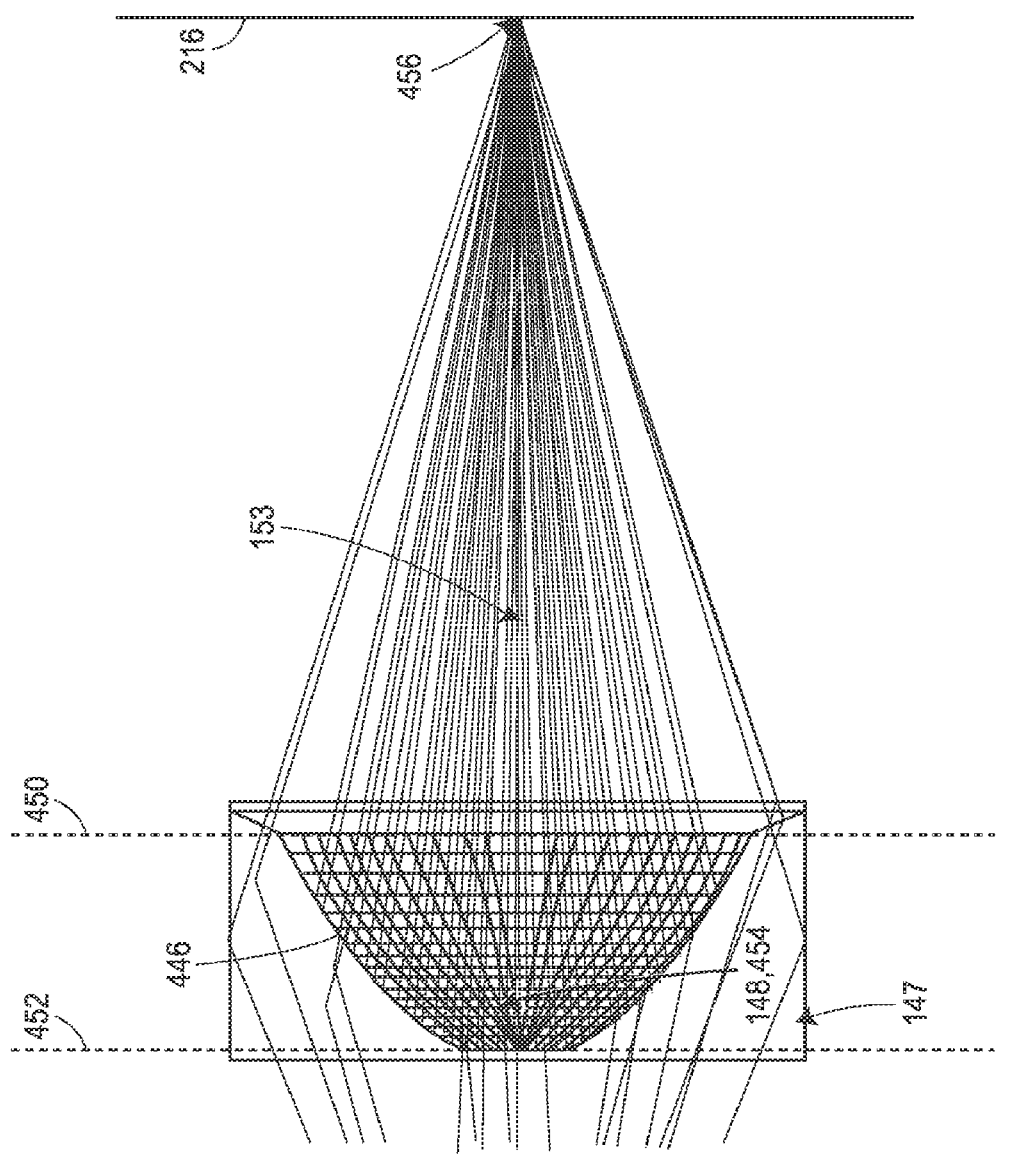

METHODS, SYSTEMS, AND APPARATUS FOR PERFORMING FLOW CYTOMETRY

CROSS REFERENCE TO RELATED APPLICATIONS

This application claims the benefit of priority under 35 U.S.C. § 120 of U.S. patent application Ser. No. 13/985,859, now U.S. Pat. No. 9,556,416, filed Sep. 30, 2013, which is a PCT national stage application of International Application PCT/US2012/025176, filed Feb. 15, 2012, and which claims priority under 35 U.S.C. § 119(e) of U.S. Provisional Patent Application Nos. 61/443,174 filed Feb. 15, 2011, 61/443,178 filed Feb. 15, 2011, and 61/482,504 filed May 4, 2011, the respective disclosures of which are incorporated herein by reference in their entireties.

BACKGROUND

Field of the Disclosure

The present disclosure relates, in general, to methods, apparatus, and systems for detecting an analyte and, in particular, for detecting an analyte in a sample flowing through a closed flow cell and optionally using a controlled energy source to affect at least a portion of the analyte within the closed flow cell after detection.

Brief Description of Related Technology

Flow cytometric sorting permits the selection, enrichment, apportionment, or division of populations of cells, viruses, bodies or particles of interest (hereinafter referred to as cells). The selection criteria include measurable properties of individual cells that can be detected from outside the cell, with or without the aid of chemical reagents or of complexes or bodies that are, or that may be caused to be, associated with the cell. For instance, properties of cells may be measured or approximated by detecting and/or quantifying the association of the cells with one or more labels, such as molecules, complexes, or bodies that fluoresce or have been modified to be rendered fluorescent. Such fluorescent molecules, complexes, and/or bodies may differentially associate with cells on the basis of qualitative or quantitative properties of the cells, including their composition with respect to proteins, lipids, phosphoproteins, glycoproteins, phospholipids, glycolipids, nucleic acids (including the quantity, sequence, or organization of nucleic acids), carbohydrates, salts/ions, and any other molecules in, on, or associated with the cells. Further, such fluorescent molecules, complexes, and/or bodies may differentially associate with cells based on physical or physiological characteristics of the cells, examples of which include but are not limited to membrane permeability, membrane composition, membrane fluidity, chemical or membrane potential, viability, chemical gradients, motility, reduction of oxidation potential or state, and other parameters or properties.

Other measurable properties of cells, whether labeled or unlabelled, modified or unmodified, that may provide a basis for cell selection may include but are not limited to:

properties of light interacting with the cells, such as fluorescence, absorbance, reflectance, scatter, polarization, or other properties;

electrical properties of the cells or of the effect of the cells on their environment, including conductance, inductance, resistance, membrane potential or voltage, or other properties;

magnetic or electromagnetic properties of cells, including magnetism, paramagnetism, magnetic resonance, and/or interaction of the cells with electromagnetic energy;

the appearance, image, or morphological properties of the cells; and the makeup of the cells with respect to any substance or parameter, measured directly or indirectly in any way.

Furthermore, the measurement of such quantities and qualities, directly or indirectly, singularly or in combination, may reflect simple or complex properties of interest of the cells.

One example of such a property is the sex chromosome included in the diploid, haploid, or gamete genome, which may be an X chromosome, a Y chromosome, a Z chromosome, a W chromosome, or the lack of a sex chromosome (referred to as '0'), or combinations thereof depending on the cell type and the organism. Further, other sex determining systems are known that are related to the presence of other chromosomes or DNA sequences. In many cases, the determination of sex chromosome content of cells may be inferred using direct or indirect measurements or determinations using one or more methods. Such methods include the measurement of the DNA content of the cells determined relatively or absolutely; the presence or absence of certain DNA sequences, or markers of the presence or absence of certain DNA sequences; the size of the cells or of portions or organelles of the cells; the presence, localization, or absence of proteins or other markers characteristic of the sex chromosome content of the cells, or combinations or patterns of expression of such markers; or any other measurement that reflects the sex chromosome composition of the cell. Many other such measurements may be made, or properties determined, to identify cells that are of interest in a particular instance, situation, system, disease, condition, process, or circumstance.

Such cytometric measurements permit quantitative and/or qualitative determinations about cells, populations of cells, organs, tissues, or organisms. Such determinations may be used in many ways including, but not limited to, diagnosis, biomedical research, engineering, epidemiology, medicine, agriculture, animal husbandry, livestock management, zoology, biopharmaceutical industry, and other fields. In addition to the ability to perform such measurements, current methods and instrumentation permit the separation of cells based on characteristics or parameters measured by cytometry as described above. Cells can be selected positively or negatively by the concentration, collection, separation, or partitioning of cells of interest or by the removal of cells that are not desired or of interest in the preparation. Such selection may be controlled on the basis of any parameter, characteristic, or combination of parameters or characteristics that may be determined as described above.

Cells identified by methods including or related to those described above may be separated, partitioned, concentrated, depleted, or collected into any arbitrary number of groups. One common separation method (depicted in FIG. 1A) uses electrostatic forces to divert an electrically or electrostatically charged stream, droplet, or droplets containing a cell or cells having desired or undesired properties. The diverted cells are collected or discarded as appropriate to the particular application, as illustrated in FIG. 1A. Other separation methods include the use of fluidic devices including valves, or other methods that alter the flow properties or direction of a stream of gas or liquid, to divert cells in a fluid stream to alternate pathways, channels, tubes, or elements for subsequent collection or disposal, as illustrated in FIG. 1B. Yet other methods include the use of methods disruptive to the flow, such as intersection by a controllable second stream, to divert a portion of a stream containing a cell or particle of interest in order to divert cells in the fluid stream to alternate pathways, channels, tubes, or elements for subsequent collection or disposal, as illustrated in FIG. 1B. Separation of the fluid stream into alternate, diverging pathways can be achieved in a variety of ways. For example, U.S. Pat. No. 6,400,453 describes diversion of the fluid using a fluid switch of liquid or compressed gas. International Patent Publication No WO 2010/149739 describes yet another means of diverting the flow into different pathways using a laser to heat the fluid flow causing a disruption in the flow and diversion of the flow path.

There exist a number of methods and systems for performing flow cytometric sorting of cells. Among these are methods and systems designed to perform flow cytometric sorting of mammalian sperm cells and, in particular, to sort the sperm cells into populations of sperm cells bearing X chromosomes and/or populations of sperm cells bearing Y chromosomes, with the purpose of increasing the probability that fertilization of an egg with the sorted sperm will result in offspring with a desired sex. For example, a dairy farmer may desire to sort the sperm of a bull so that bovine embryos may be produced, by artificial insemination, in vitro fertilization, or other means, using a preparation of sperm cells having an increased frequency of X chromosome-bearing sperm cells, to produce additional female bovine offspring.

Flow cytometric sorting methods present a number of challenges, particularly with respect to sorting mammalian sperm cells for later use in producing offspring. Importantly, methods used to label and/or to differentiate between the cells and/or methods used to sort the cells must not adversely affect the viability of the cells. Often, one or more goals of the methods and/or systems involved (e.g., faster sorting, improved accuracy, etc.) conflict with other goals of the methods and/or systems. Various factors must be balanced and considered, including the temperatures, temperature changes, pressures and/or pressure changes to which the cells are subjected, the fluidic environments to which the cells are exposed, the chemical environments and substances to which the cells are exposed, the forces applied to the cells, and the lifespan of the cell. For example, the rate at which a fluorescent molecule (e.g., a fluorochrome) enters a cell to bind to DNA within the nucleus of the cell (i.e., the rate at which cells may be stained), may increase as temperature increases. Thus, the throughput of a system (at least the throughput of the staining process) may increase with an increase in the temperature of the cells' environment. However, increased temperature may prove detrimental to the viability of the cells and/or the length of time that the cells remain viable. By contrast, maintaining the cells at a reduced temperature to promote the maintenance of good viability may increase the time required for staining (and consequently of the entire operation comprising measuring and sorting) the cells, such that the process takes longer than is practical or such that the cells are not viable after the time required to complete the process.

Another challenge associated with sorting cells relates to the physical and optical properties of the cells. In particular, flattened or otherwise asymmetrical cells, such as some mammalian red blood cells or sperm cells, may exhibit anisotropic emission of energy (e.g., light). The complex geometries of a cell's interior and/or the complex geometries of the cell's boundaries act to transmit, refract and/or reflect light in ways that are highly dependent on the orientation of the cell with respect to any illumination sources and/or detectors used to differentiate between cells. For example, flow cytometry sorting of mammalian sperm cells into populations having increased frequency of cells containing X or Y chromosomes usually involves staining the cells with a molecule that binds to DNA within the cells and fluoresces brightly when bound. The variation in DNA content between the X and Y chromosomes of most mammalian species (Y chromosomes generally containing less DNA than X chromosomes) results in relatively greater fluorescence from cells containing X chromosomes. However, the difference in DNA content of X and Y chromosome bearing cells is typically on the order of only a few percent and, often, cell geometry and/or orientation may affect the detected fluorescence by a percentage that exceeds the percentage difference in DNA content between the X and Y chromosomes. Additionally, such analysis requires that cells pass through the detection region singly, such that a detector does not interpret fluorescence from two cells as fluorescence from a single cell.

Flow cytometry sorting systems frequently employ a core-in-sheath fluidic mechanism to carry the cells through the detection region. As depicted in FIG. 1C, a relatively slow moving stream 750 of an aqueous suspension of cells 752 is injected into a relatively faster moving flow 754 of sheath fluid. This arrangement focuses the cells 752 into a stream 756, referred to as the core stream. With appropriate selection of the pressures, of the shape, dimensions, orientation, and materials of the boundaries and components of the fluidic system, and the consequent velocities and organization of the core suspension and sheath fluid, the core stream is narrowed by hydrodynamic forces exerted by the sheath flow, and the cells in the core stream are distributed longitudinally such that they are carried mostly one by one in the flow. The forces that elongate and narrow the core stream have the additional benefit of orienting the cells 752 such that a lengthwise axis 758 of the cell 752 is generally parallel to the direction of flow of the single file stream 756. However, the orientation of the cells about the lengthwise axis 758 remains more or less random in systems where the core and sheath flows are designed to be generally cylindrically symmetric about the flow axis. Thus, as each cell 752 passes through the detection area, light incident upon the cell, light emitted from the cell (e.g., fluorescent light or scattered light or transmitted light), and light reflected off of the cell, remain dependent on the orientation of the cell 752. This is especially true of many types of mammalian sperm cells.

There are a number of solutions to the problem of sperm cell orientation with respect to illumination and detection of cells within flow cytometry systems. For example, FIG. 1D illustrates one solution, which solution employs a cut, beveled tip 760 on a tube 762 injecting a sample stream 764 into a sheath flow 766. The flattened, beveled tip 760 helps to orient the cells about their lengthwise axes 758 (illustrated in FIG. 1C) within the sheath flow 766 such that the flat faces of the cells tend to align in a consistent direction. Another solution (which may be combined with the beveled tip solution) employs two detectors 768 and 770 orthogonal to each other (a 0-degree detector 68 and a 90-degree detector 770) which are used in combination to estimate the orientation of each cell as it passes through a detection area 772 and to measure the fluorescence of those cells that are found to be appropriately oriented such that precise quantitation of the fluorescent signal is possible. The solutions employing hydrodynamic orientation of cells around the lengthwise axis generally yield populations in which the desired alignment for fluorescence measurement is achieved for about 60% to about 80% of the cells in the sample flow, which decreases the throughput of the instrument and results in the discarding of improperly oriented cells.

Still another solution to the problems associated with cell geometry and orientation utilizes optical detection along the same axis as the core-in-sheath flow that carries the cells. In one such solution, epi-illumination optics are used to illuminate the cell and detect light emitted by the cell. As depicted in FIG. 1E, a sample stream 774 carried by a sheath flow 776 travels directly towards a microscope objective lens 778, eliminating the dependence on the orientation of the cell (e.g., a sperm cell 780) about a lengthwise axis 782 of the cell 780. However, the trajectory of the cell 780 towards the objective lens 778 requires that the cell 780 change trajectory immediately after passing through a detection area 782 (i.e., the focal point 784 of the objective lens 778). The system accomplishes this trajectory change by using a transverse flow 786 of fluid. Uncertainty in the position of individual cells may be introduced after the analysis by the convergence 788 of the transverse fluid flow 786 and the sheath flow 776 and sample stream 774. Such position uncertainty may render the system inoperable to perform cell sorting because the location of the cell 780 within the converged flow may become unpredictable immediately or shortly after the cell passes through the detection area 784.

Yet another solution, illustrated in FIG. 1F, utilizes one or more parabolic or ellipsoidal reflectors 802 to illuminate cells uniformly and/or to collect light radially from the cells. The system utilizes a nozzle 804 to emit a stream/jet 806 of liquid containing individual cells 792. The stream 806 moves through a detection region 794 and through a hole 796 in the reflector 802. At some point after passing through the detection region, the stream 806 is broken into droplets 790 which may be electrically charged. Thereafter, each of the droplets 790 may be sorted by, for example, deflecting the charged droplet 790 using electrically charged deflector plates 798 to deflect the droplets into one or more receptacles 800. Problematically, this "jet-in-air" configuration subjects the stream 806 (and the cells 792 contained within the stream 806) to a drop in pressure as the stream 806 exits the nozzle 804. Sudden changes in pressure (and the increased pressures within the nozzle itself), may adversely affect the viability of the cell 792 as can the subsequent impact of the cell 792 into the receptacle 800. Thus, the pressure and speed of the stream 806 exiting the nozzle 804 must remain below any threshold that could damage the cells 792, which decreases the throughput of the system. Additionally, the movement of the droplets 790 through the atmosphere may require environmental constraints including cleanliness of the room air (e.g., a "clean room") and temperature-control.

Thus, even with the relatively advanced state of flow cytometry, there exists an ongoing need in the art to provide more efficient, more sensitive, and more precise methods of and devices for cell identification and/or separation.

SUMMARY

In accordance with an embodiment of the disclosure, an apparatus for identifying analytes of a first type in a fluid sample comprising analytes of a plurality of types, comprises a closed flow cell. The flow cell comprises a sample inlet, a sample outlet, and a flow path defined between the sample inlet and sample outlet. The flow path passes through an interrogation region, wherein at least the portion of the flow path extending from immediately upstream of the interrogation region to immediately downstream of the interrogation region is bounded by a flow cell wall to form a continuous closed flow path, without division or bifurcation. The apparatus further includes a spherical element having a center point coincident with the interrogation region. A hydrodynamic focusing element upstream of the interrogation region creates a core-in-sheath flow along a flow axis of the flow path as it passes through the interrogation region, which core-in-sheath flow includes a core flow carrying the analytes. The apparatus also includes a concave, ellipsoidal collector element comprising a vertex, an optical axis, a first focal point disposed in the interrogation region of the flow path, and a second focal point. Still further, the apparatus includes illumination means comprising a plurality of beams of electromagnetic energy converging non-axisymmetrically at the interrogation region, each of the plurality of beams orthogonal to the flow axis.

BRIEF DESCRIPTION OF THE DRAWING FIGURES

FIG. 3 is a schematic illustration of a method and apparatus for detecting an analyte in accordance with embodiments of the disclosure;

FIGS. 4A and 4B are schematic illustrations of embodiments of the direction of flow of a sample in accordance with embodiments of the disclosure;

FIG. 5A is a schematic illustration of a hydrodynamic focusing element in accordance with embodiments of the disclosure;

FIG. 19 is a schematic illustration of an elliptical collector element collecting the detectable signal from an analyte at the interrogation region in accordance with an embodiment of the disclosure;

DETAILED DESCRIPTION

Figure 1A:
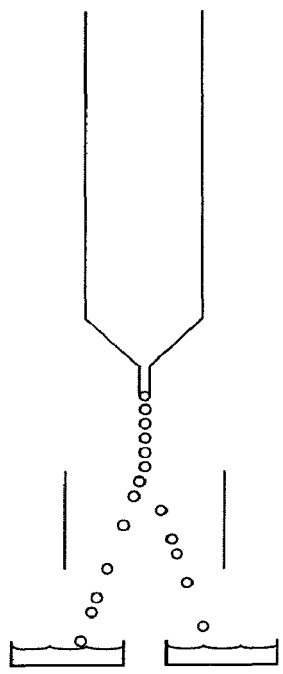
FIGS. 1A-1F are schematic illustrations of prior art methods of sorting a sample using flow cytometry.
Figure 1B:
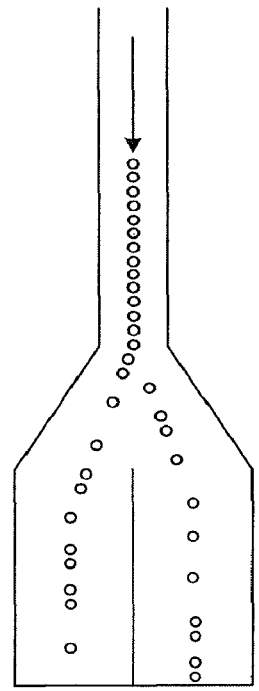
Figure 1C:
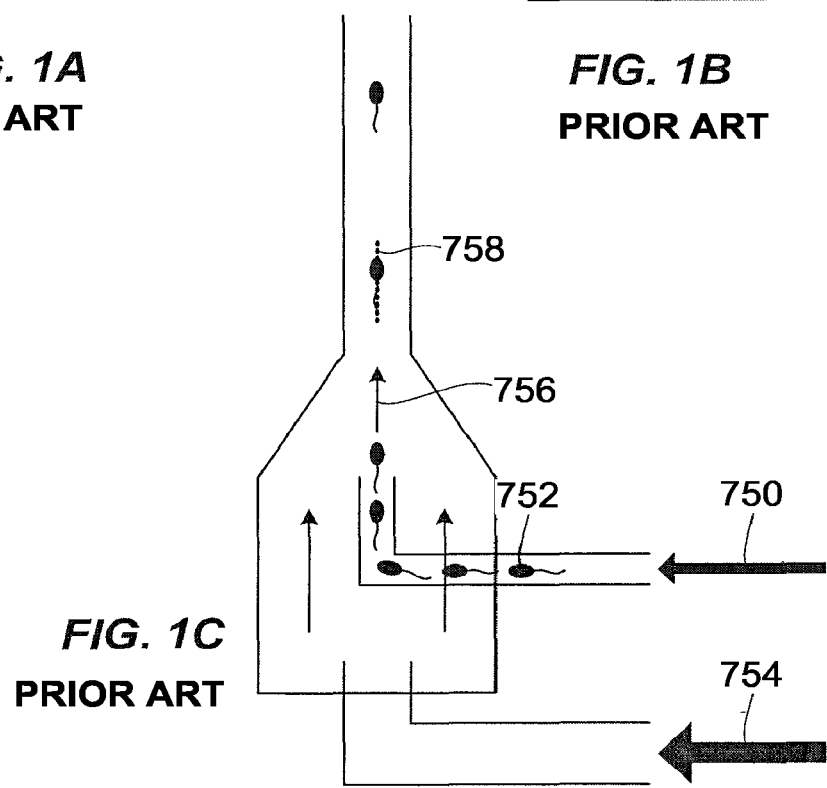
Figure 1D:
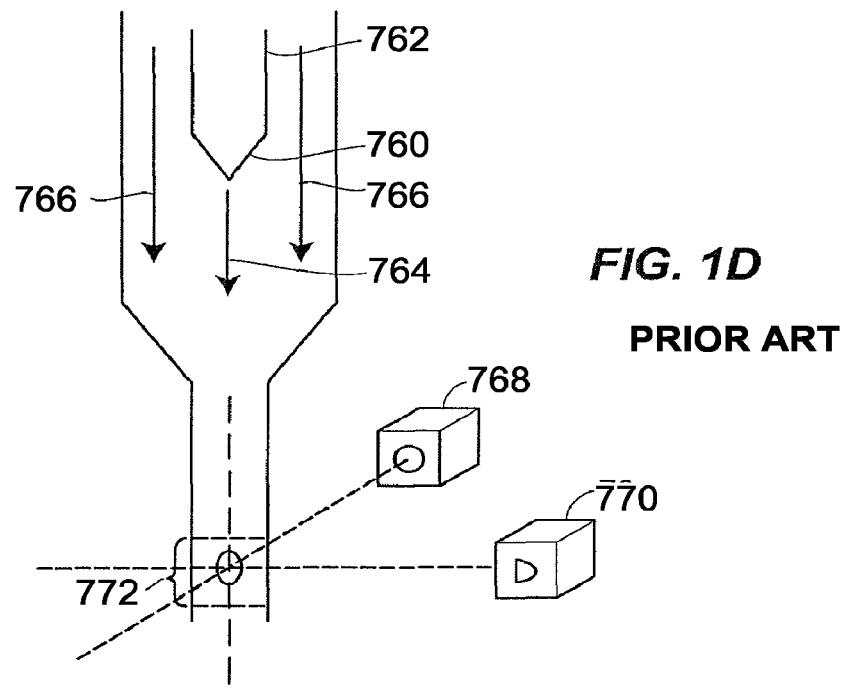
Figure 1E:
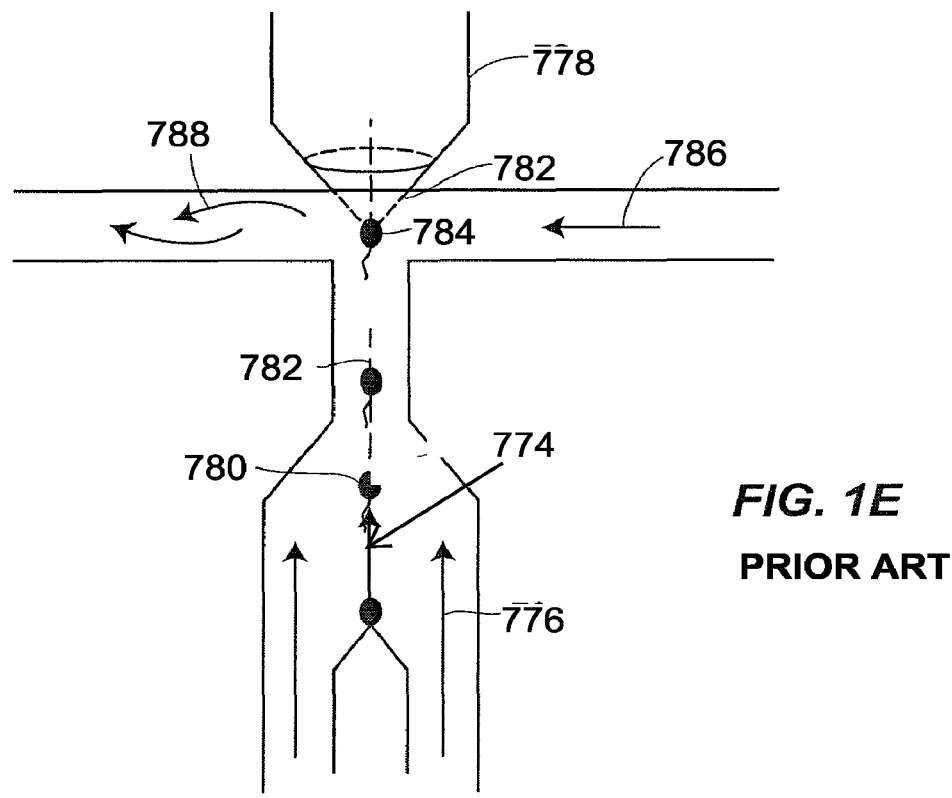
Figure 1F:
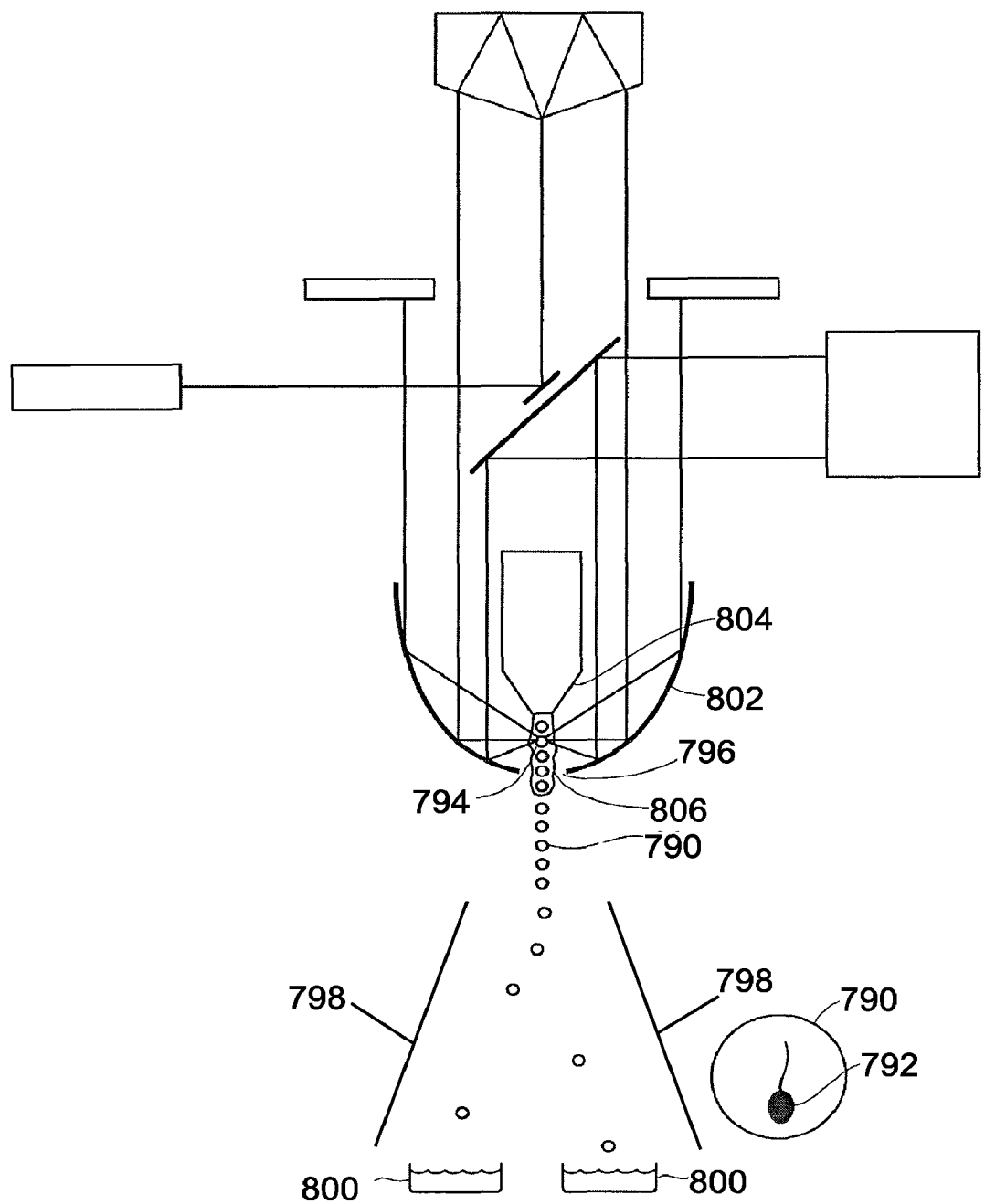

The described methods and apparatus permit identification of analytes of interest by detecting the presence or absence of any number of characteristics (e.g., a desired property) or parameters that can be determined, estimated, or reflected in measurements compatible with flow cytometric techniques. While described herein with respect to analytes in general and, occasionally, with respect to cells in particular, it should be understood that the methods and apparatus described herein are applicable to analytes generally and that, in specific instances, the case of a flow cytometer is described with respect to cells or, more specifically, with respect to spermatozoa. In any event, reference to "cells" or "cellular populations" in the description should be understood as not limiting, but rather merely as an application to a specific circumstance of the principles described.

Cytometric measurements used to define analytes or analyte populations of interest include in various aspects those discussed herein and those otherwise known in the art, as well as novel measurement methods, mechanisms, and/or apparatus that may be introduced or made applicable to flow cytometric analysis. Analytes subjected to cytometric analysis through practice of the presently described methods and apparatus, may be labeled or unlabelled, or otherwise modified or unmodified using techniques and reagents known in the art.

As used herein, the term "label" refers to a composition detectable by photometric, image analysis, spectroscopic, photochemical, biochemical, immunochemical, or chemical means. For example, useful labels include fluorescent dyes, electron-dense reagents, enzymes, biotin-streptavidin, dioxigenin, haptens, proteins for which antisera or monoclonal antibodies are available, or nucleic acid specific dyes. Thus, in the presently described methods and apparatus, the makeup, properties, and/or characteristic of analytes with respect to any substance or parameter, measured directly or indirectly in any way is the basis for the identification of analytes and analyte populations for selection or exclusion.

Examples of detectable makeup, properties, and/or characteristics of analytes include, but are not limited to, (1) measurements of properties of light interacting with the analytes or emitted by the analytes, such as absorbance, light scattering, luminescence, fluorescence, phosphorescence, polarization or depolarization of light, or other properties; (2) properties of electricity including, but not limited to inductance, capacitance, potential, current, or resistance of analytes or of the surrounding medium; (3) properties of electromagnetism including magnetism, paramagnetism, magnetic resonance, and/or interaction of the analyte with or emission of electromagnetic forces and/or waves; and (4) imaging, image properties, morphological properties, or related properties derived from the collection and/or analysis of image or image-like properties of analytes. In certain aspects, the measurement is an intrinsic quantity or quality of the analyte, or in alternative aspects, the measurement is a value that indirectly reflects, represents, or approximates, a quantity or quality of the analyte. In still other aspects, the measurement is both an intrinsic quantity or quality of the analyte and an indirect reflection, representation, or approximation of a quantity or quality of the analyte. By way of example and not limitation, a detection or measurement of the fluorescence generated by an analyte may represent the intrinsic fluorescence of the analyte or the presence and/or quantity of a fluorochrome or fluorescent particle that binds to or otherwise associates with the analyte, which can be directly and/or indirectly indicative of some property of the analyte.

In some aspects of the described methods and apparatus, the analytes are cells (e.g., mammalian spermatozoa) and a sorting cytometer employs a technique that results in the physical or spatial separation of cells and cell populations. In other aspects of the described methods and apparatus, a sorting cytometer utilizes a technique that physically and/or functionally modifies selected cells in populations to permit their functional and/or physical separation and/or differentiation, optionally for subsequent use. In some aspects of the described method and apparatus, a sorting cytometer does not rely on immediate separation of cells by position, location, vessel, or time, but instead provides cells are that inactivated, incapacitated, disrupted, disarticulated, fragmented, or otherwise altered (i.e., "modified") with respect to some desired property, that optionally allows separation or differentiation of subpopulations in the preparation. The nature of the modification depends, all or in part, on an intended application or use for identified cells, and thus, characteristics of the identified cells that are relevant in the application. For example and for purposes of explanation or clarification only, a malignant or otherwise immortal or rapidly growing cell might be considered functionally inactivated in the context of the preparation of normal somatic cells if the cell's capacity to reproduce is negatively affected or if the cell is killed. In another example, again for purposes of explanation or clarification only, where an application requires the removal from a population of a subpopulation of cells, for example a subpopulation that produces an undesirable protein or other substance, a sorting cytometer may achieve this result by abrogating production of the substance in these cells, by killing the cells, and/or by modifying the cells to permit their physical removal from the population.

The methods and apparatus presently described utilize, in some embodiments, a sorting energy source for modification of cells or for the induction or initiation of processes such as chemical activation that may modify cells. Modifications induced by the sorting energy source include in various aspects, direct effects on the analyte. For example, when the analyte is a cell, the direct effect on the cells can include, but is not limited to, (1) the modification of cellular components or chemicals including proteins, DNA, and substances involved in cellular metabolism; (2) disruption, heating, cavitation, or explosions occurring in or near the cells; permeabilization or perforation of cells; and (3) destruction, fragmentation, or morphological alteration of cells, including cells, viruses, bodies or particles.

In other embodiments, modifications can also or alternatively include indirect effects of the sorting energy source, mediated by the sorting energy source or by other factors, including, for example, (1) chemical activation and/or deactivation, chemical crosslinking, or chemical derivitization of the cells or of one or more cellular components, (2) the activation and/or deactivation of one or more chemical agents in or near the cell that causes the binding or association of such agents or derivatives thereof to the cell or its components, or (3) the induction of altered functionality of the cell. In certain embodiments, chemical agent(s) that react upon irradiation with the cell can be normally present in the cell or in the application, or the chemical agent(s) can be are added to the sample fluid as part of the method.

In some embodiments, the described methods and apparatus incorporate the use of photoactivatable compounds that are induced to bind or otherwise associate with cells or cellular components upon irradiation with light of an appropriate intensity and energy. In some embodiments, the photoactivatable compound can induce sufficient crosslinking or denaturation of one or more cellular components to affect cellular processes or metabolism of cells of interest. Alternatively, the photoactivatable compounds can induce sufficient crosslinking or denaturation of one or more cellular components to kill cells of interest. In another alternative, a photoactivatable compound can bind or otherwise associate with selected cells and alter one or more properties of cells of interest in such a way as to render the cells of interest amenable to identification and/or enrichment and/or depletion in subsequent processes.

Cells of interest that have been altered by chemical derivatization, such as by the addition of a chemical substance, are in certain aspects removed, concentrated, or purified in a subsequent step by methods that utilize the properties or interactions of such a substance. For example, and for purposes of explanation and clarification only, cells of interest are, in one aspect, derivatized by the addition of a substance that is subsequently bound by an antibody that permits the capture or retention of the derivatized cell of interest by various means. Many such substances are contemplated, and in one aspect, such substances include a class of compounds containing or related to the 2,4-dinitrophenyl group (DNP), which in one aspect is recognized and specifically bound by antibodies recognizing DNP. Accordingly, photoactivatable derivatives of DNP or related compounds are used in one aspect to derivatize cells of interest in an application of this type.

Alternatively, derivatized cells of interest can be captured or removed using strategies that cause the derivatized cells of interest to bind preferentially to certain substrates. For example and for purposes of explanation and clarification only, cells of interest derivatized using compounds containing or related to biotin are in one aspect captured or retained on substrates, surfaces, substances, media, compounds, or particles that bind or have been modified to bind biotin, for instance by the presence of avidin, streptavidin, biotin-binding antibodies, or other biotin-binding molecules. In another alternative related to this aspect, photoactivatable derivatives of biotin or related compounds are used to derivatize cells of interest in such an application. Alternately in other aspects, cells of interest are altered by the addition or association of chemical substances or compounds before being subjected to selection and modification. In such a case, therefore, an embodiment of the methods and apparatus described herein utilizes alteration of the added substance on selected cells to permit the differentiation of such cells from others in the population. For instance, and for purposes of explanation and clarification only, in one aspect all cells in a population are derivatized by the addition of a photolabile chemical compound before analysis, and in one aspect, specific cells are targeted for modification using the energy source of the apparatus to modify the photolabile chemical compound on those cells.

Figure 2:
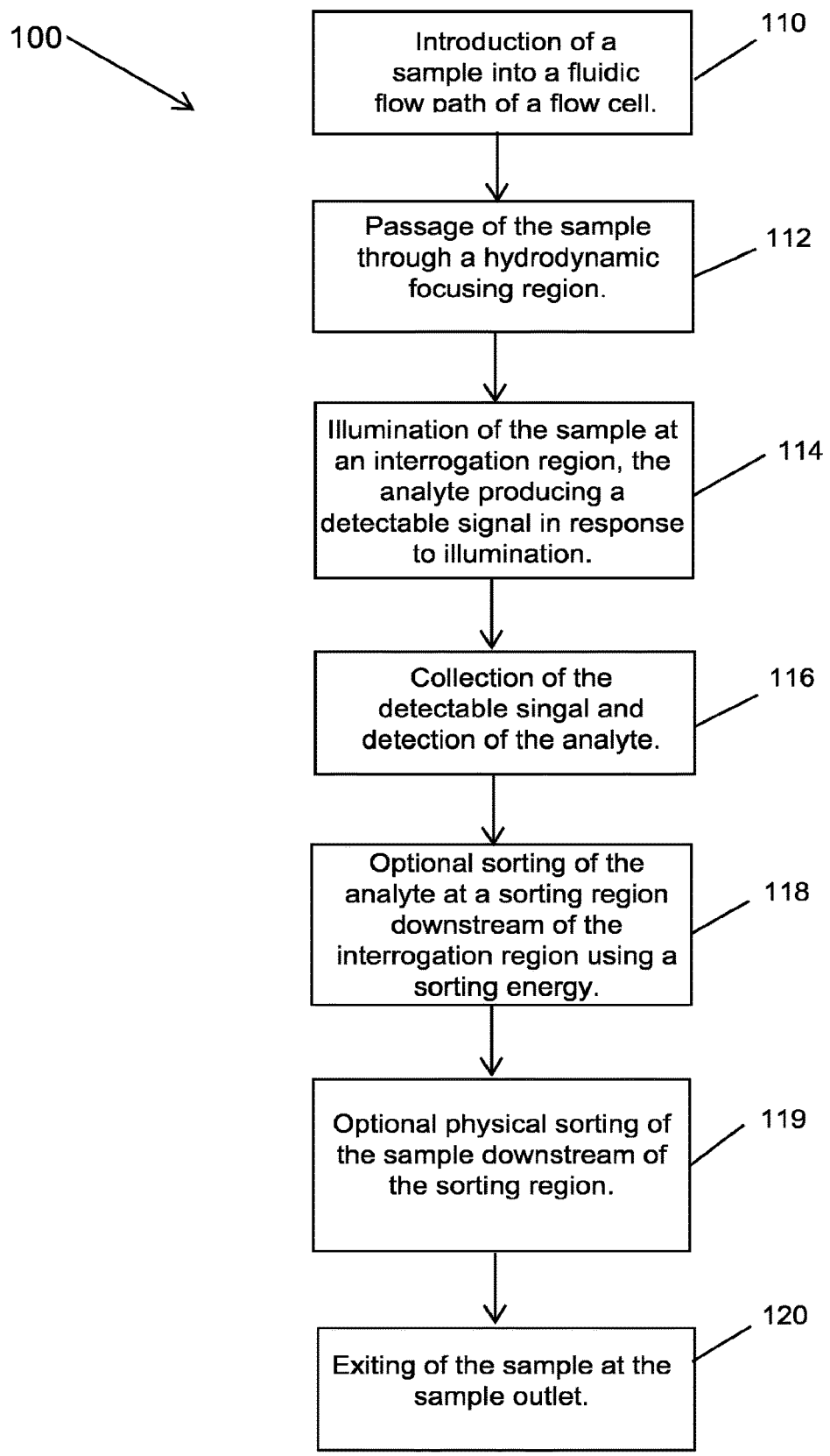
FIG. 2 is a flow diagram illustrating a method of detecting an analyte in accordance with embodiments of the disclosure.

Referring to FIG. 2, in an embodiment of the disclosure, a method 100 for detection and optionally high-speed sorting of an analyte may generally sequentially include, for example, introduction of a sample containing or suspected of containing an analyte into a fluidic flow path of a flow cell through a sample inlet (step 110), passing of the sample through a hydrodynamic focusing region (step 112), illumination of the sample at an interrogation region, the analyte generating a detectable signal in response to illumination (step 114), collection of a detectable signal and detection of the analyte or a desired feature of the analyte (step 116), optionally sorting the analyte or an analyte of interest using a sorting energy directed at the analyte in a sorting region downstream of the interrogation region, the sorting energy operable to modify, damage, or destroy the analyte (step 118), optionally physically sorting the sample at the sample outlet or other region downstream of the sorting region (step 119), and exiting of the sample through a sample outlet of the flow cell (step 120).

While the various steps of the methods are described separately above and in detail below, it should be understand that steps of the method can be performed simultaneously or substantially simultaneously. For example, introduction of the sample into the fluidic flow path and hydrodynamic focusing can occur simultaneously, for example, in embodiments in which the flow cell is formed of a capillary tube. The capillary tube can effect near immediate focusing of the sample. In another embodiment, a hydrodynamic focusing element can be provided at the sample inlet such that the sample inlet is the hydrodynamic focusing region and/or includes a hydrodynamic focusing apparatus and the sample becomes focused upon entry into the fluidic flow path of the flow cell. Alternatively, a hydrodynamic focusing element or region can be provide downstream of the sample inlet and the sample can be focused after introduction at the inlet.

Another example of steps that can occur simultaneously or substantially simultaneously include the optionally physical sorting of the sample downstream of the sorting region and exiting of the sample out the sample outlet. As described in detail below, the physical sorting can occur while the sample exits the sample outline. In other embodiments, a region of physical sorting upstream the sample outline, but downstream the sorting region can also be provided such that physical sorting occurs prior to exiting of the sample.

For example, illumination of the sample, collection of the detectable signal, and detection of the analyte can all occur substantially simultaneously as well. By substantially simultaneously, it should be understood that the illumination, collection, and detection steps are performed at the speed at which the sample can illumination, generate a detectable signal, and the detectable signal can be collected and transmitted to a detector. For example, such action can occur at about the speed of the electromagnetic energy and thus, can be considered substantially simultaneous.

The methods and apparatus for detecting an analyte in accordance with embodiments of the disclosure have improved accuracy and throughput as compared to conventional flow cytometry systems. The methods and apparatus have a variety of applications including differentiating cells for example, on the basis of the quantity of DNA they contain, specific proteins or other biomolecular markers they contain, and/or specific genetic markers they contain (naturally occurring or not). The methods and apparatus also have application in the differentiation of an analyte, for example cells, by the use of a florescence antibody or genetic probe or stain that results in a detectable difference between cells with or without the marker, or results in the ability to measure a difference in the expression or quantity of the marker. The methods and apparatus of the disclosure have particular utility for sexing sperm cells.

Embodiments of the apparatus advantageously provide a flow cytometry system in which the optical arrangement (i.e., a collector element and optionally optical elements) does not form a barrier or otherwise require diversion or redirection of the sample flow, between the interrogation region and the sorting region, around the optical arrangement, while allowing the sample to flow in any desired direction.

Reference to FIG. 3 in the following description of the general methods and apparatus is provided only for illustrative purposes and does not in any way limit the illumination method, optical arrangement, sorting method, or any other elements of the methods and apparatus of the disclosure, as are described in detail below. Referring to FIG. 3, the apparatus in accordance with embodiments of the disclosure generally include a closed flow cell 132 having a sample inlet 134, a sample outlet 136, and a flow path 138 extending between the sample inlet 134 and sample outlet 136. The flow cell 132 may optionally include a sheath fluid inlet and sheath fluid supply container (not shown) for introduction of the sheath fluid into a region of the flow cell for later formation of a core-in-sheath flow. The apparatus also include an illumination source (not shown) for illumination at an interrogation region 148 and a concave collector element 146 for collecting a detectable signal generated by the analyte 142 in response to illumination. The analyte can, upon illumination, reflect, emit, transmit, or otherwise generate the detectable signal. The concave collector element 146 has an associated vertex 159, optical axis 161, and focal point 163. As used herein, "vertex" shall be understood to include those regions of or related to the collector element 146 corresponding to a vertex regardless of whether the collector element 146 includes a physical vertex, is truncated, or includes an opening or gap where a physical vertex would otherwise be located. As used herein, "optical axis" refers to an axis of the collector element passing through the focal point and about which the concave collector element has rotational symmetry. As used herein, "focal point" is used in its ordinary meaning in the art, and for further clarity refers to a virtual point at which electromagnetic energy received by the collector element is focused. As the sample passes through the interrogation region, it has a flow axis 145 coincident with the optical axis 161 of the collector element 146. The apparatus also includes a detector 150 for detecting the collected detectable signal.

Figure 4B:
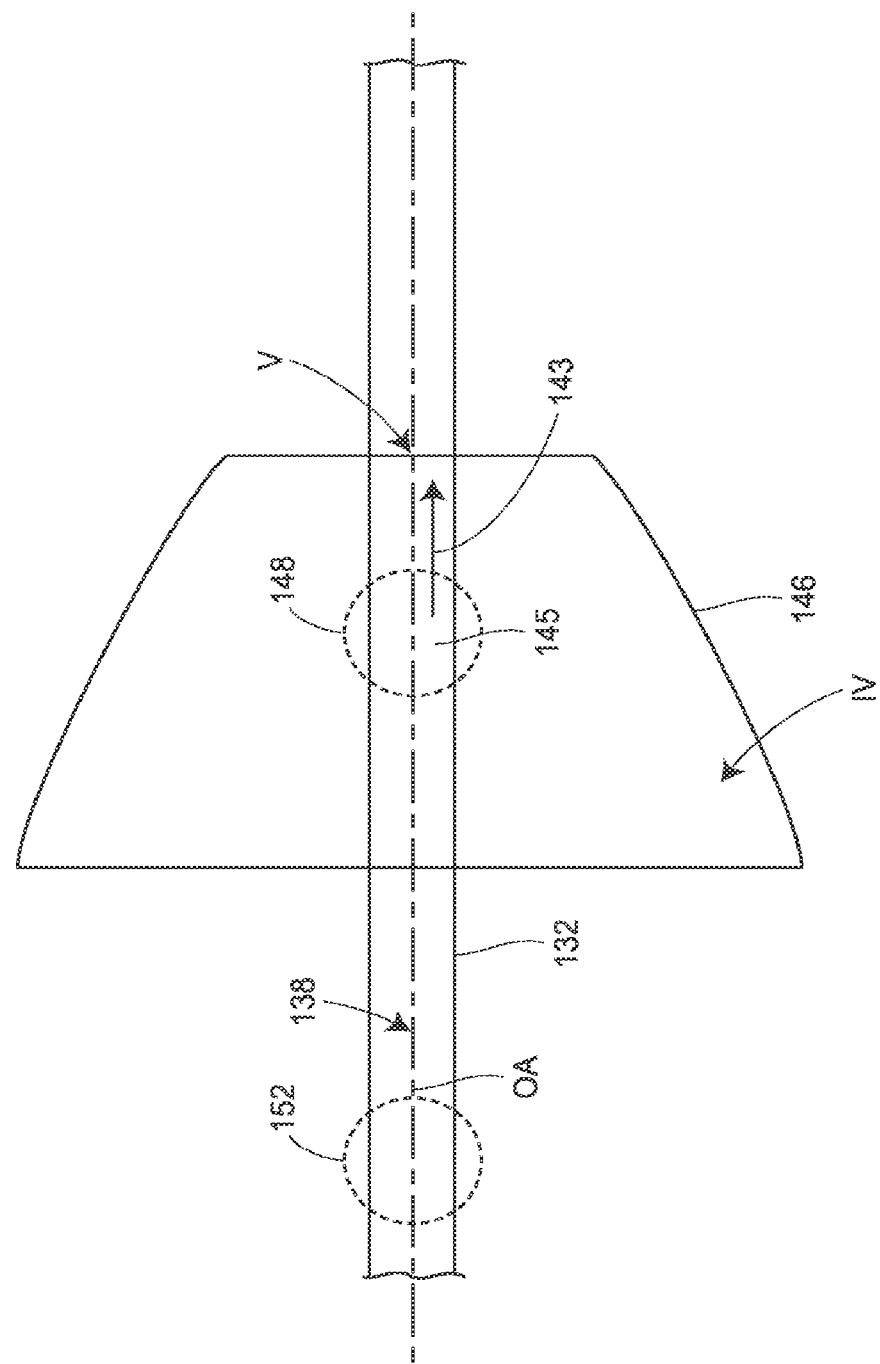

A sample comprising or suspected of comprising the analyte 142 is supplied to the closed fluidic flow cell 132 through the sample inlet 134. Referring to FIG. 4A, in some embodiments, the sample flows in the flow path 138 from the interrogation region 148 towards the vertex 159 of the collector element 146. Referring to FIG. 4B, in other embodiments, the sample flows in the flow path 138 from the vertex 159 of the collector element 146 toward the interrogation region 148. In both flow embodiments, a portion of the flow path 138 passes through an internal volume 167 of the collector element 146. FIG. 3 also illustrates an embodiment in which the sample flows from the vertex 159 of the collector element 146 towards the interrogation region 148.

In various embodiments, a portion of the flow cell 132 passes through the collector element 146 or a region or space in the wall of the collector element 146. For example, as shown in FIGS. 3, 4A and 4B, the collector element 146 is truncated and a portion of the flow cell 132 passes through the opening in the region corresponding to the vertex 159 of the collector element 146. It is contemplated that the flow cell 132 may pass through a portion or opening of the concave collector element including the vertex, a hole drilled in the vertex, and/or an opening or hole in one or more side walls.

The interrogation region 148 is coincident with the focal point 145 of the collector element 146. In some embodiments, the interrogation region 148 may be a single point that is coincident with a focal point 163 of the collector element 146. In other embodiments, for example, as shown in FIG. 4A, the interrogation region 148 may have a maximum outer boundary that is in a range of about 0 μm to about 150 μm upstream and/or downstream from the focal point FP of the collector element 146. Other suitable boundaries (upstream, downstream, or both upstream and downstream from the focal point 163 of the collector element 146) include, for example, 0 μm to about 100 μm, about 1 μm to about 80 μm, about 5 μm to about 70 μm, about 10 μm to about 60 μm, about 15 μm to about 50 μm, about 20 μm to about 40 μm, about 15 μm to about 30 μm, about 100 μm to about 150 μm, about 50 μm to about 150 μm and about 30 to about 100 μm. Suitable boundary distances may also include, for example, about 0, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, and 150 μm.

The portion of the flow path 138 passing through the interrogation region 148 is coaxially aligned with the optical axis 161 of the collector element 146.

As used throughout the disclosure, "coaxially" refers to alignment of elements about their respective axes within a tolerance of about 0° to about 15°. For example, suitable tolerances include about 0, 1, 2, 3, 4, 5, 6, 7, 8, 9, 10, 11, 12, 13, 14, and 15°.

The sample is illuminated at the interrogation region 148 by the illumination source (not shown in FIG. 3) or through focusing of the electromagnetic energy emitted by the illumination source onto the interrogation region 148 using an optical arrangement (exemplary embodiments of which are described in detail below). The analyte 142 produces a detectable signal in response to illumination. The collector element 146 collects the detectable signal and reflects or transmits the detectable signal to the detector 150 for detection of the analyte 142. The apparatus and method may optionally include a sorting energy source for sorting of the analyte 142 at a sorting region 152 downstream of the interrogation region 148.

The flow cell 132 is a closed flow cell having a sample inlet 134, a sample outlet 136, and a flow path 138 defined between the sample inlet 134 and sample outlet 136. The flow cell can have any suitable cross sectional shape, including, but not limited to, circular, elliptical, rectangular, square, or any other polygon. In various embodiments, the flow cell is cylindrical having a circular cross-sectional shape. In any of the embodiments described herein, the flow cell 132 may optionally include a spherical molding 154 (as shown in FIG. 3) surrounding the interrogation region 148. The spherical molding 154 may be formed of a material having an index of refraction within a suitable tolerance of the index of refraction of the wall of the flow cell 132 at the interrogation region. As discussed in detail below, the spherical molding may mitigate or eliminate refractive distortion of the detectable signal resulting from the flow cell wall-air interface. The tolerance may be for example in a range of 0 to 0.1.

As used herein, "closed flow cell" refers to a flow cell 132 wherein at least the portion of the flow path 138 passing through the interrogation region 148 and through the sorting region 152 is a closed flow path. As used herein, "closed flow path" refers to a flow path having a unitary flow path that is bounded by a flow cell wall and has no division or bifurcation. As used herein, "division" and "bifurcation" refer to any separation of the flow path into two or more separate paths. Accordingly, the closed flow cell 132 of the disclosure includes a flow path 138 between and through the interrogation region 148 and sorting region 152 that is completely bounded and undivided. Thus, in the flow cell 132 of the disclosure, sorting at the sorting region 152 is effected by a sorting energy focused on the sorting region 152 and not by physical sorting of the sample into divided flow paths. The closed flow cell advantageously eliminates the undesirable refractive effects on the electromagnetic energy caused by the interface between droplets in the sample and air in conventional, unclosed flow cells. As discussed in detail below, embodiments of the disclosure may, however, further include a region of physical sorting downstream of the sorting region 152, for example, at the sample outlet 136, for physically sorting the sample after application of the sorting energy, and/or for dividing the flowing fluid into separate components, for example and not by way of limitation, for separating some of the sheath fluid from the sample-containing analyte.

The stages of the method of the disclosure and the apparatus for performing the method will be described in detail below. Any combination of the hydrodynamic focusing elements, illumination methods, optical arrangements, and sorting methods individually described below may be used in methods and apparatus in accordance with embodiments of the disclosure.

Fluid Flow and Hydrodynamic Focusing

The sheath fluid and the analyte fluid are injected into the fluidic flow path 138. For example, a hydrodynamic focusing element may form in the flow cell a core-in-sheath flow of the analyte within a sheath fluid or a laminar flow. The core-in-sheath flow or laminar flow may be substantially stable prior to passing through the interrogation region 148. The flow rate of the core-in-sheath flow may be about 1 m/s to about 60 m/s. The analytes 142 within the core-in-sheath flow may be spaced such that about 10,000 to about 300,000 cells per second pass through the interrogation point 148. The spacing between the analytes 142 may be adjusted by, for example, adjusting the relative velocities and/or flow rates of the core and sheath flows, which may, in turn, be accomplished by a flow control system adjusting respective signals to pumps connected to the respective supplies of sheath fluid and sample fluid.

Some fluidic flow systems, such as, but not limited to, core-in-sheath flow, have the property of orienting non-symmetrical cells, particles, or analytes, such that the long axis of the cells, particles, or analyte is aligned coaxially with the direction of fluid flow. Such is well understood by those experienced in the art to be the case for certain spermatozoa, including many types of mammalian spermatozoa, and it has been demonstrated that sperm cells may align in a core-in-sheath flow such that the long axis of the cells is substantially coaxial with the flow. Thus, in some embodiments, a core-in-sheath flow or other methods of flow may provide a longitudinal alignment of particles (e.g., mammalian sperm cells) carried therein.

The longitudinal alignment of particles in flow is of practical benefit, by way of example, and without limitation, for the analysis of the deoxyribonucleic acid (DNA) content of spermatozoa. Spermatozoa carry DNA, and direct or indirect measurements of the relative quantity of DNA in the sperm cell may be made in a flow cytometer using fluorescent dyes such as 4',6-diamidino-2-phenylindole dihydrochloride or bisbenzimide (Hoechst 33312) with which the cells may be treated to derive a fluorescent measurement that correlates with the amount of DNA in the individual cell. Because sperm cells may, in some species including, but not limited to, many mammals, contain either an X or a Y chromosome, which is predictive of the female or male (respectively) sex of offspring of the union of the sperm cell with an oocyte, and because the X and Y chromosomes may be of different size, and further because other chromosomes and DNA in sperm cells may be relatively invariant in total amount, the fluorescence of appropriately fluorescently stained sperm cells may be used to determine whether they contain an X or a Y chromosome. However, sperm cells may be non-cylindrically symmetrical about the major longitudinal axis. Such is the case, for example and without limitation, for human and bovine sperm cells. Such cells have flattened cell bodies, also known as heads, and it is well understood by those skilled in the art that such asymmetrical bodies emit fluorescence anisotropically, such that the fluorescence in one direction may be significantly different from the fluorescence in another direction about the long axis of the sperm cell. For this reason, it is difficult to measure with precision the fluorescence of sperm cells from directions about the long axis of sperm cells without first determining the rotation angle with respect to the detector. Methods for orienting and/or determining the orientation of sperm cells in flow are known to those skilled in the art, and have achieved the necessary precision for the discrimination of X and Y chromosome bearing sperm cells, for instance Johnson, U.S. Pat. No. 5,135,759, the disclosure of which is incorporated herein by reference in its entirety. However, the fluorescence of sperm cells in the direction of the long axis is relatively invariant as a function of the rotation of the cells about the long axis. Meistrich and Gohde, et al. (1978: Resolution of X and Y spermatids by pulse cytophotometry. Nature 274(5673): 821-823) and others have demonstrated that the discrimination of X and Y chromosome bearing sperm cells is practically achievable when the sperm cells are oriented longitudinally in a fluid flow, for example a core-in-sheath flow, and when the fluorescence detection optics are oriented coaxially with the flow.

It has been advantageously determined that the stress exerted on a cell during hydrodynamic focusing may be measured according to the maximum local energy dissipation rate and such measurement provides a better prediction of the mortality rate of cells in a sample due to hydrodynamic focusing as compared to predictions based on the shear stress. The energy dissipation rate (EDR) may be calculated using the following formula:

$$\varepsilon = \mu(\nabla U + \nabla U^T):\nabla U$$

wherein $\varepsilon$ is the EDR, $\mu$ is the viscosity, $(\nabla U + \nabla U^T)$ is the stress tensor, $\nabla U$ is the velocity gradient tensor, $\nabla U^T$ and is the transpose of $\nabla U$. EDR accounts for both shear and extensional forces acting on a cell in suspension.

In some embodiments, a hydrodynamic focusing element may be incorporated into a portion of the flow cell 132 to form a core-in-sheath flow. The hydrodynamic focusing element may beneficially provide one or more of the following advantages: creating laminar flow of analyte particles within the core-in-sheath flow, eliminating or minimizing recirculation at the injection point 155 of the core flow into the sheath flow, attaining a dilution factor of the core with respect to the sheath of less than 20:1, maintaining stable core flow for more than 0.200 mm, and as much as several centimeters, minimizing shear stress experienced by the analyte particles, minimizing the maximum local energy dissipation experienced by the analyte particles, and/or creating a single file flow of analytes at a rate of greater than 10,000 particles per second and up to 300,000 particles per second. Other known advantages of hydrodynamic focusing are also contemplated herein.

The hydrodynamic focusing element may be placed in any suitable location in the flow path 138 so long as the stable laminar or core-in-sheath flow is established before the sample passes through the interrogation region 148.

Figure 5B:
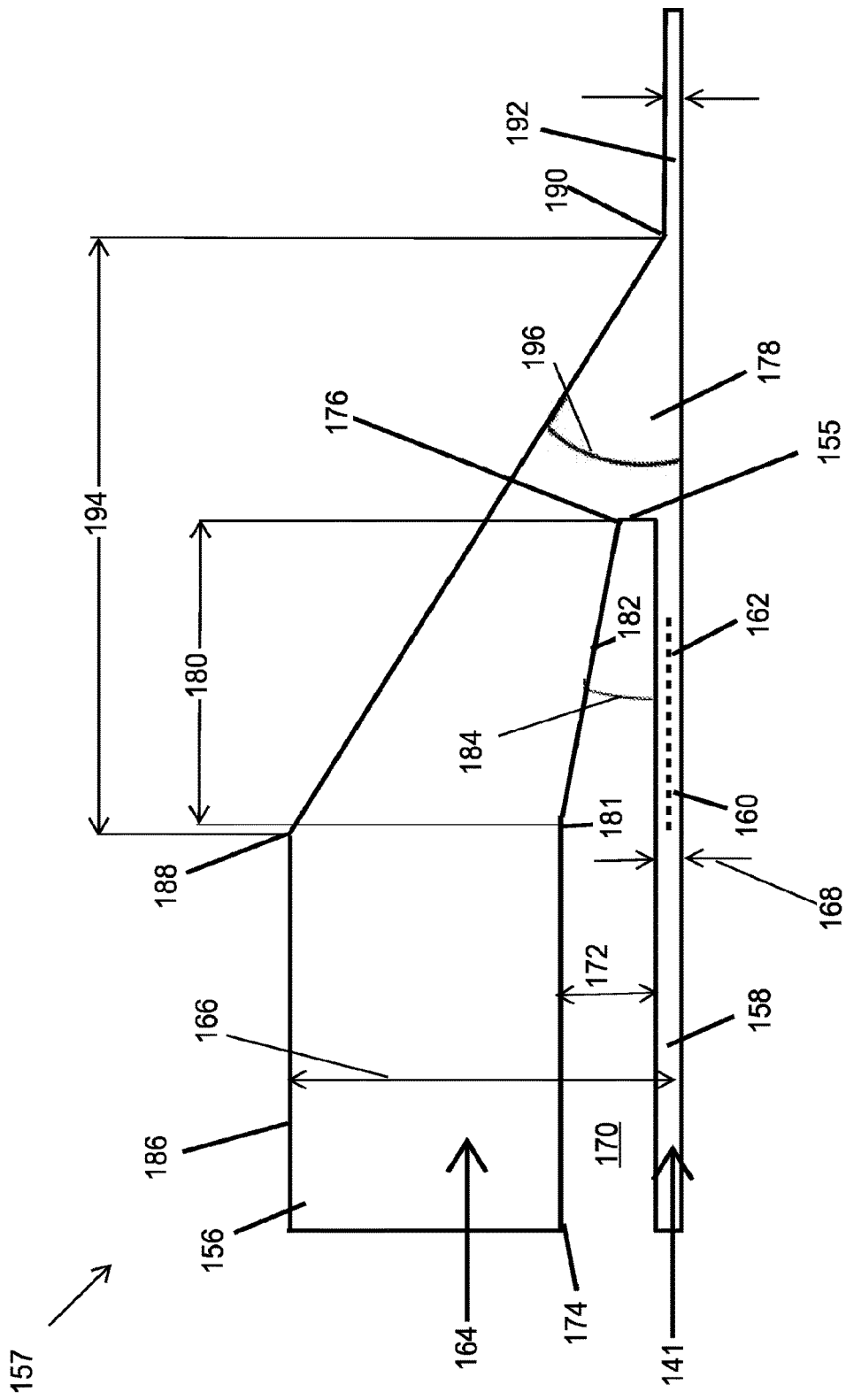
FIG. 5B is a schematic illustration of a cross section of the hydrodynamic focusing element of FIG. 5A taken through line A-A'.

FIG. 5A illustrates is an embodiment of a hydrodynamic focusing element 157 that may be used in the methods and apparatus of the present disclosure. FIG. 5B is a cross-sectional image of the hydrodynamic focusing element 157 of FIG. 5A through line A-A' shown on FIG. 5A. Referring to FIGS. 5A and 5B, an exemplary hydrodynamic focusing element 157 has an outer flow path 156 and an inner flow path 158 disposed inside the outer flow path 156. The inner flow path 158 and the outer flow path 156 may each have a respective flow axis 160, 162, and the flow axes 160, 162 may be coaxially aligned. The outer flow path may define a flow path, for example, for a sheath fluid 164, and the inner flow path may define a flow path, for example, for a sample 141 containing or suspected of containing an analyte 142.

The outer flow path 156 may have a maximum radius 166, for example, in a range of about 0.4 mm to about 20 mm, about 0.6 mm to about 15 mm, about 0.8 mm to about 10 mm, about 1 mm to about 8 mm, about 10 mm to about 20 mm, about 1 mm to about 20 mm, about 2 mm to about 18 mm, about 4 mm to about 16 mm, about 6 mm to about 14 mm, about 8 mm to about 12 mm, about 0.4 mm to about 1 mm, about 0.6 mm and about 0.7 mm, about 0.5 mm and about 0.7 mm, about 0.5 mm and about 1 mm, and about 0.4 mm and about 0.8 mm. Other suitable maximum radii 166 include, for example, about 0.4, 0.45, 0.5, 0.55, 0.6, 0.65, 0.7, 0.75, 0.8, 0.85, 0.9, 0.95, 1, 2, 3, 4, 5, 6, 7, 8, 9, 10, 11, 12, 13, 14, 15, 16, 17, 18, 19, and 20 mm. In some embodiments, the maximum radius 166 is about 0.628 mm.

The inner flow path 158 may have a maximum radius 168, for example, in a range of about 20 µm and about 1000 µm, about 30 µm and about 40 µm, about 35 µm and about 40 µm, about 35 µm and about 45 µm, about 30 µm and about 45 µm, about 20 µm and about 80 µm, about 20 µm and about 100 µm, about 20 µm and about 500 µm, about 10 µm and about 500 µm, about 10 µm and about 40 µm, about 10 µm and about 80 µm, about 10 µm and about 100 µm. Other suitable radii 168 include, for example, about 20, 30, 40, 50, 60, 70, 80, 90, 100, 200, 300, 400, 500, 600, 700, 800, 900, and 1000 µm. In some embodiments, the maximum radius 168 of the inner flow path is about 38 µm.

The hydrodynamic focusing element 157 may include a wall 170 surrounding the inner flow path 158. The wall 170 may have an outer diameter 172, for example, in a range of about 50 µm to about 300 µm, about 100 µm and about 200 µm, about 150 µm and about 200 µm, about 50 µm and about 250 µm, and about 100 µm to about 300 µm. Other suitable diameters 172 include, for example, about 50, 60, 70, 80, 90, 100, 125, 150, 175, 200, 225, 250, 275, and 300 µm. In some embodiments the outer diameter 172 is about 191 µm.

The outer surface 174 of the wall 170 surrounding the inner flow path 158 may be tapered at an end 176 disposed toward a point of convergence 178 of the inner and outer flow paths 158, 156. For example, a distance 180 from a beginning 181 of a taper 182 to the convergence 178 of the flow paths 156, 158 may be in a range of about 200 µm to about 1000 µm, about 500 µm and about 600 µm, about 550 µm and about 560 µm, about 550 µm and about 600 µm, about 400 µm and about 700 µm, about 400 µm and about 1 mm, about 200 µm and about 700 µm, or about 300 µm and about 600 µm. Other suitable distances 180 include, for example, about 200, 250, 300, 350, 400, 450, 500, 550, 600, 650, 700, 750, 800, 850, 900, 950, and 1000 µm. In some embodiments, the distance 180 is about 555 µm.

An angle 184 between the coaxial flow axes 160, 162 and the tapered outer surface 182 of the wall 170 surrounding the inner flow path 158 may be between about 0.1° and about 15°; alternately between about 0.1° and about 10°; alternately between about 5° and about 10°; alternately between about 5° and about 10°; alternately between about 8° and about 12°; alternately between about 5° and about 15°; alternately between about 9° and about 11°; alternately between about 9.5° and about 10.5°. Other suitable angles 184 include, for example, about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, and 15°. In some embodiments, the angle 184 is about 10°.

An outer surface 186 of the outer flow path 156 may be tapered from a first point 188 to a second point 190. The second point 190 may be a point corresponding to the formation of a stable core-in-sheath flow 192, while the first point 188 may, in some embodiments, be coplanar with the beginning of the taper 182 of the outer surface 174 of the wall 170 surrounding the inner flow path 158, on a plane orthogonal to both the inner and outer flow paths 158, 156. The distance 194 along the axis 160, 162 of the flow path 138 from the first point 188 to the second point 190 may be in a range of about 1 mm and about 1.1 mm, about 0.8 mm and about 1.1 mm, about 0.8 mm and about 1.2 mm, about 0.5 mm and about 1.2 mm, about 0.56 mm and about 1.1 mm, about 0.56 mm and about 1.2 mm. Other suitable distances 194 include, for example, about 0.5, 0.52, 0.54, 0.56, 0.58, 0.6, 0.62, 0.64, 0.66, 0.68, 0.7, 0.72, 0.74, 0.76, 0.78, 0.8, 0.82, 0.84, 0.88, 0.9, 0.92, 0.94, 0.96, 0.98, 1, 1.02, 1.04, 1.06, 1.08, 1.1, 1.12, 1.14, 1.16, 1.18, and 1.2. In some embodiments, the distance 194 is about 1.062 mm.

An angle 196 between the coaxial flow axes 160, 162 and the tapered outer surface 186 of the outer flow path 156 may be in a range of about 15° and about 45°, about 15° and about 35°, about 25° and about 45°, about 25° and about 35°, about 27° and about 33°, or about 29° and about 31°. Other suitable angles 196 include, for example, about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, and 45°. In some embodiments, the angle 196 is about 30°.

Sheath fluid 164 flowing through the outer flow path 156 may flow at a rate of between about 20 mm$^3$ per second and about 600 mm$^3$ per second; alternatively, between about 20 mm$^3$ per second to about 400 mm$^3$ per second, alternately between about 20 mm$^3$ per second and about 200 mm$^3$ per second; alternately between about 20 mm$^3$ per second and about 100 mm$^3$ per second; alternately between about 20 mm$^3$ per second and about 85 mm$^3$ per second; alternately between about 25 mm$^3$ per second and about 85 mm$^3$ per second; alternately between about 35 mm$^3$ per second and about 85 mm$^3$ per second; alternately between about 40 mm$^3$ per second and about 85 mm$^3$ per second; alternately between about 50 mm$^3$ per second and about 85 mm$^3$ per second; alternately between about 75 mm$^3$ per second and about 85 mm$^3$ per second; alternately between about 80 mm$^3$ per second and about 81 mm$^3$ per second, alternatively between about 500 mm$^3$ per second to about 600 mm$^3$ per second, alternatively between about 100 mm$^3$ per second to about 600 mm$^3$ per second, alternatively between about 200 mm$^3$ per second to about 400 mm$^3$ per second, alternatively between about 300 mm$^3$ per second to about 500 mm$^3$ per second, alternatively between about 400 mm$^3$ per second to about 500 mm$^3$ per second, alternatively between about 300 mm$^3$ per second to about 400 mm$^3$ per second; and specifically 80.3 mm$^3$ per second. For example, suitable rates include about 20, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, and 600 mm$^3$ per second.

Core fluid (i.e., the sample 141) may flow through the inner flow path 158 at a rate of between about 0.1 mm$^3$ per second to about 30 mm$^3$ per second, about 10 mm$^3$ per second to about 30 mm$^3$ per second, about 15 mm$^3$ per second to about 20 mm$^3$ per second, about 1 mm$^3$ per second to about 30 mm$^3$ per second, about 2 mm$^3$ per second to about 20 mm$^3$ per second, about 4 mm$^3$ per second to about 18 mm$^3$ per second, about 6 mm$^3$ per second to about 16 mm$^3$ per second, about 8 mm$^3$ per second to about 10 mm$^3$ per second, about 20 mm$^3$ per second to about 30 mm$^3$ per second, about 0.1 mm$^3$ per second and about 10 mm$^3$ per second; alternately between about 2 mm$^3$ per second and about 10 mm$^3$ per second; alternately between about 3 mm$^3$ per second and about 10 mm$^3$ per second; alternately between about 3 mm$^3$ per second and about 8 mm$^3$ per second; alternately between about 3 mm$^3$ per second and about 6 mm$^3$ per second; alternately between about 3.5 mm$^3$ per second and about 4.5 mm$^3$ per second; and specifically about 4 mm$^3$ or about 3.93 mm$^3$ per second. Other suitable rates include, for example, about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 mm$^3$ per second.

In various embodiments, the hydrodynamic focusing element 157 may result in a stable core-in-sheath flow 192 having a sheath diameter in a range of between about 10 μm and about 50 μm; alternately between about 10 μm and about 40 μm; alternately between about 10 μm and about 30 μm; alternately between about 10 μm and about 20 μm; alternately between about 20 μm and about 30 μm; alternately between about 20 μm and about 40 μm; alternately between 20 μm and about 50 μm; alternately between about 30 μm and about 40 μm; alternately between about 30 μm and about 50 μm; alternately between about 25 μm and about 35 μm; and specifically about 30 μm. In various embodiments, the hydrodynamic focusing element 157 may result in a stable core-in-sheath flow 192 having a core diameter in a range of between about 1 μm and about 10 μm; alternately between about 2 μm and about 9 μm; alternately between about 3 μm and about 10 μm; alternately between about 5 μm and about 10 μm; alternately between about 5 μm and about 7 μm; alternately between about 5 μm and about 15 μm; and specifically about 6 μm.

Figure 6:
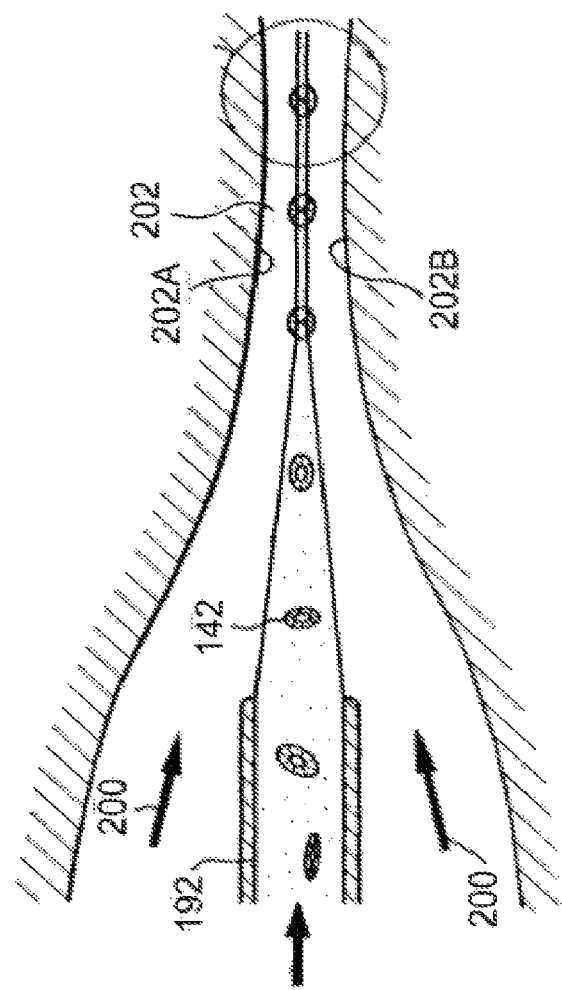
FIG. 6 is a schematic illustration of a prior art hydrodynamic focusing element in accordance with another embodiment of the disclosure.

In other embodiments, the core-in-sheath flow may be established, for example, as described in U.S. Pat. No. 5,007,732, the disclosure of which is incorporated herein by reference. Referring to FIG. 6, core-in-sheath flow may be established, for example, using a hydrodynamic focusing element 198 having a sample tube, through which the sample containing or suspected of containing the analyte 142 flows, disposed in the center of a sheath fluid flow 200. The hydrodynamic focusing element 198 includes a capillary flow passage 202 having one side wall 202A that has a smooth surface and the other side wall 202B has a roughened surface. A laminar flow forms within the capillary passage and, by virtue of the arrangement of the flow of the sample and the sheath fluids, forms a core-in-sheath flow. In some embodiments, the hydrodynamic focusing element 198 represented in FIG. 6 may be modified for injection of only a sample fluid without injection of the sheath fluid 200 to induce a laminar flow in the capillary region without necessarily forming a core-in-sheath flow.

Figure 7A:
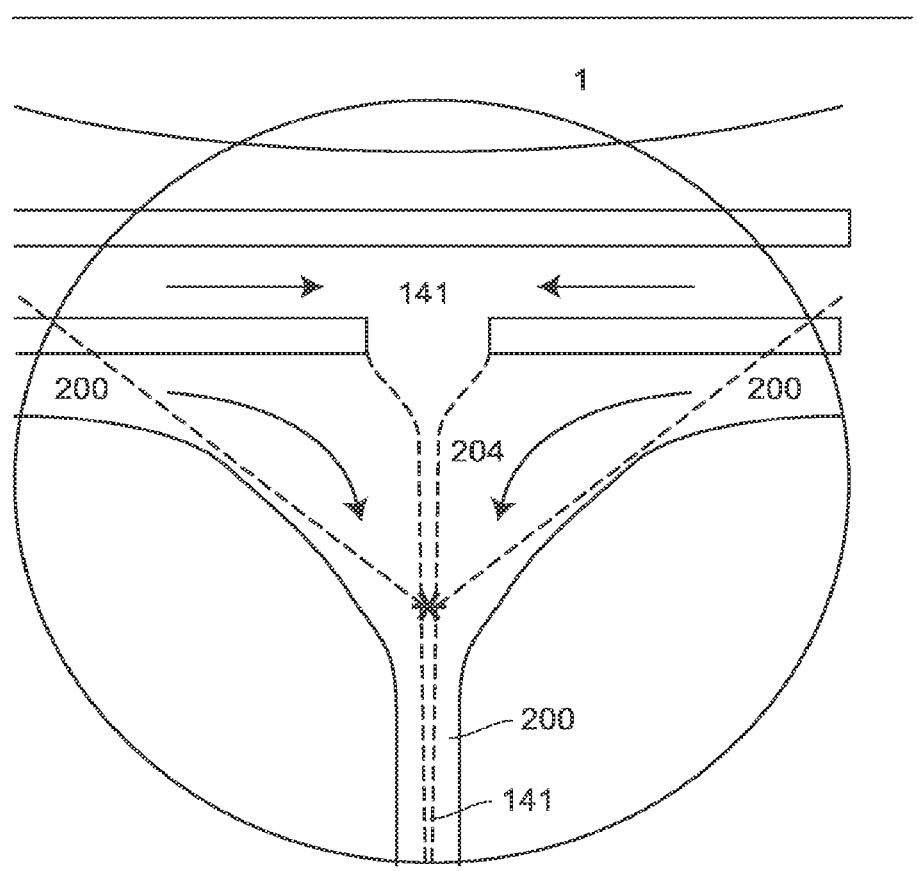
FIG. 7A is a schematic illustration of a method of forming a core-in-sheath flow in accordance with an embodiment of the disclosure.
Figure 7B:
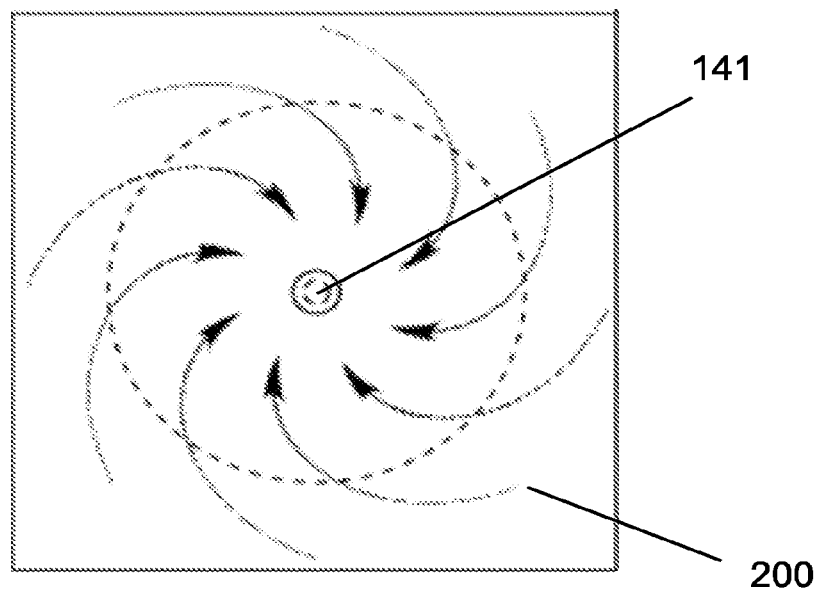
FIG. 7B is a schematic illustration of the flow formation of the method of FIG. 7A before the acceleration region.
Figure 7C:
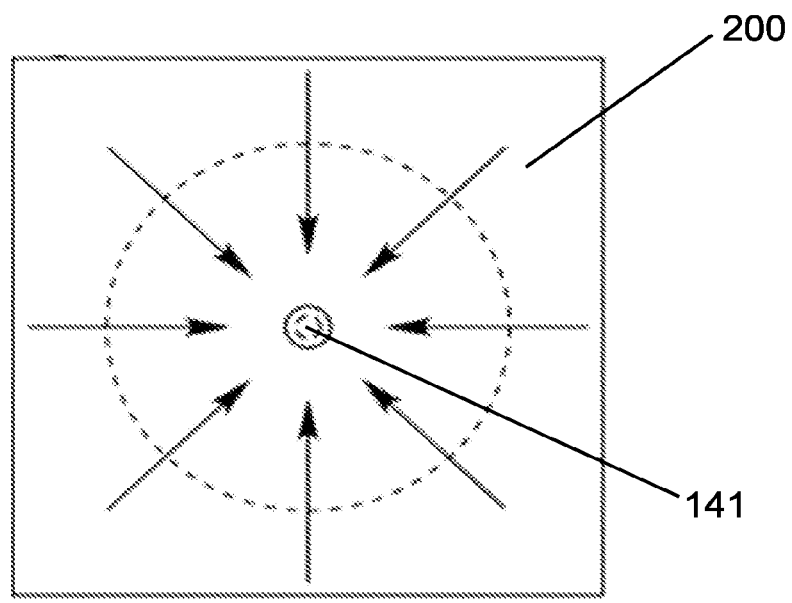
FIG. 7C is a schematic illustration of the core-in-sheath flow resulting from the method of FIG. 7A after the acceleration region.

Referring to FIG. 7A, the core-in-sheath flow may be formed for example by introduction of a sheath fluid 200 and a sample 141 containing the analyte 142 in a plane orthogonal to the optical axis of the collector element (not shown) and directing the flow through an acceleration region 204 for generating core-in-sheath type flow. The sample 141 is directed to enter through the center of the sheath flow 200 through an orifice or chamber disposed in the sheath fluid flow path. Both flows enter the acceleration region 204 and establishing a stable core-in-sheath flow. As shown in FIG. 7B, the sheath flow 200 may have a rotational flow above the acceleration region 204, which can aid in core formation of the sample 141. Referring to FIG. 7C, the flow stabilizes after the acceleration region 204 to form the stable core-in-sheath flow.

In yet other embodiments, laminar flow can be achieved by forming at least a portion of the flow cell of a capillary tube and passing the sample flow through the capillary tube, which results in ordering of the analyte.

Figure 8:
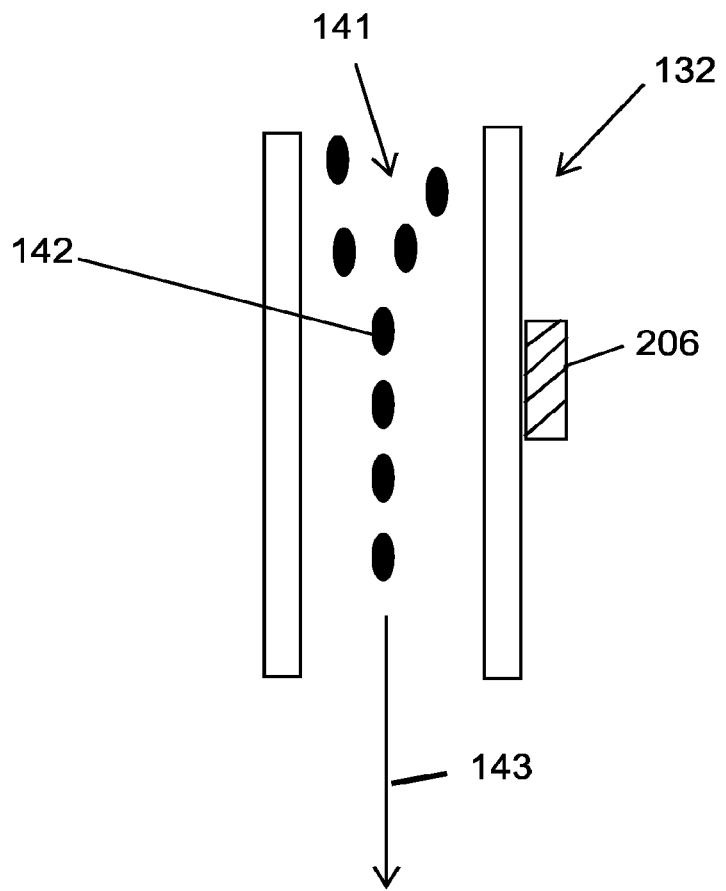
FIG. 8 is a schematic illustration of a conventional method of acoustically focusing a sample flow to enhance the central alignment of the analyte.

As described in U.S. Pat. No. 7,340,957, and U.S. Patent Publication Nos. 2010/0009333 and 2009/0162887, the disclosures of which are each incorporated herein by reference in their entireties, the flow cell and/or any of the above-described hydrodynamic focusing elements can be used with acoustical focusing devices for further refinement of the sample flow. For example, as illustrated in FIG. 8, the analytes 142 of a sample can be more centrally aligned within a sample stream using acoustic focusing. A sample flows through the flow cell past a transducer 206, which emits mechanical wavelengths inducing a standing wave in the sample fluid. The analytes are attracted to the center of the sample flow as this is the most stable region in the standing wave. Acoustic focusing can be used with any of the aforementioned hydrodynamic focusing methods to further enhance the sample flow for illumination and detection.

Illumination

The sample may be illuminated with any source of electromagnetic energy and any type of electromagnetic energy sufficient to excite or otherwise elicit a detectable signal from the analyte upon illumination. For example, electromagnetic energy from an illumination source (or focused therefrom by an optical arrangement) may fall incident upon the analyte, and may cause light to reflect off of, or be transmitted through, one or more elements within the analyte or on the surface of the analyte. Alternatively or additionally, electromagnetic energy may fall incident upon the analyte or upon an element within the analyte and may be absorbed or adsorbed by one or more elements within the analyte or on the surface of the analyte and may cause the one or more elements to emit a detectable signal, such as light or other electromagnetic energy. In some embodiments, the element within or on the surface of the element may be a marker (naturally occurring or otherwise) added to the analyte, for example, a cell. For example, the marker may emit a fluorescent signal in response to illumination. In an embodiment, the marker is a fluorescent dye such as 4',6-diamidino-2-phenylindole dihydrochloride or bisbenzimide (Hoechst 33312).

As used herein "illumination" refers to illumination, excitation, or other energetic stimulation of the analyte or an element or marker for generating a detectable response. For example, the electromagnetic energy may be light in the visible spectrum, light in the infrared spectrum, and/or light in the ultraviolet spectrum. Other types and wavelengths of suitable electromagnetic energy may also be used in any of the described embodiments of the disclosure.

The illumination source may be any suitable source of electromagnetic energy. For example, the illumination source may be a laser or a source of non-coherent light, such as, a mercury arc lamp, a tungsten lamp, a metal halide lamp, a xenon lamp, or a light emitting diode. In some embodiments, the electromagnetic energy may be circularly polarized, for example, by use of a quarter wave plate. Circular polarization may advantageously reduce polarization dependence of the detectable signal. In some embodiments, the detector or one or more flat mirrors aligned with the detector element (as described in detail below) may include polarization elements that may mitigate the dependence of the detected or measured signal on polarization of the illumination source.

In some embodiments, an illumination source 151 directly illuminates the sample at the interrogation region 148. For example, one or more illumination sources may illuminate the sample at any desired angle relative to the axis of flow at the interrogation region. For example, the illumination source may illuminate the sample in a plane orthogonal to the axis of flow at the interrogation region. Other angles of illumination may also be suitable. For example, in various embodiments, the illumination source may illuminate the sample coaxially with the axis of flow at the interrogation region.

The interrogation region may be illuminated from one or more directions over points, angels, solid angles, or regions of arbitration shape. Flat optical elements, such as flat mirrors may be incorporated into any of the illumination methods and configurations described in detail below to divert the path of the electromagnetic energy to the desired region of the apparatus, for example, another optical element or the interrogation region, to allow for versatility of the optical arrangement of the apparatus. For example, such flat optical elements may be used to align the collector element, detector, optical elements (if present), and sorting energy (if present) other than coaxially. In some embodiments, such redirection of the electromagnetic energy may allow for more compact arrangement of one or more of the collector element, detector, optical elements (if present), and sorting energy (if present).

In some embodiments, the interrogation region is illuminated with rotational symmetry. As used herein, "rotational symmetry" refers to illumination of the interrogation region that is rotationally symmetric about any given axis. In other embodiments, the interrogation region is illuminated axisymmetrically. As used herein, "axisymmetrically" refers to illumination of the interrogation region that is rotationally symmetric about the optical axis of the collector element. Illumination is considered rotationally symmetric or axisymmetric despite interruptions or obstructions in electromagnetic energy path, due to for example, an element of the apparatus, as long as the illumination would be rotationally symmetric or axisymmetric but for the interruption or obstruction. By way of example, coherent light sources incident on the interrogation region from any chosen direction may be chosen to have an angle of incidence that is approximately 54.7° from each other, or from the axis of the collection element, where 54.7° is an angle known in the art to be advantageous in some circumstances for the reduction of measurement difficulties related to polarization (Asbury et al. Cytometry 40:88-101 (2000)). Such illumination is rotationally symmetric.

In yet other embodiments, the interrogation region is illuminated from a single direction or from a multiplicity of directions that are not defined by rotational symmetry. By way of example only, and without limitation, such a non-symmetric illumination scheme may include the use of several laser beams converging on the interrogation point from the plane perpendicular to the flow axis at the interrogation region, such that the angles of incidence of the illumination sources are irregularly spaced and are not related by rotational symmetry.

In various embodiments, one or more illumination sources may be used to directly illuminate the sample at the interrogation region at various angles distributed about the axis of flow at the interrogation region. In such embodiments, light from the illumination source may be directly focused on the interrogation region at the desired angle of illumination or one or more flat optical elements may be used to direct the electromagnetic energy to the interrogation region at the angle of interest.

Figure 9:
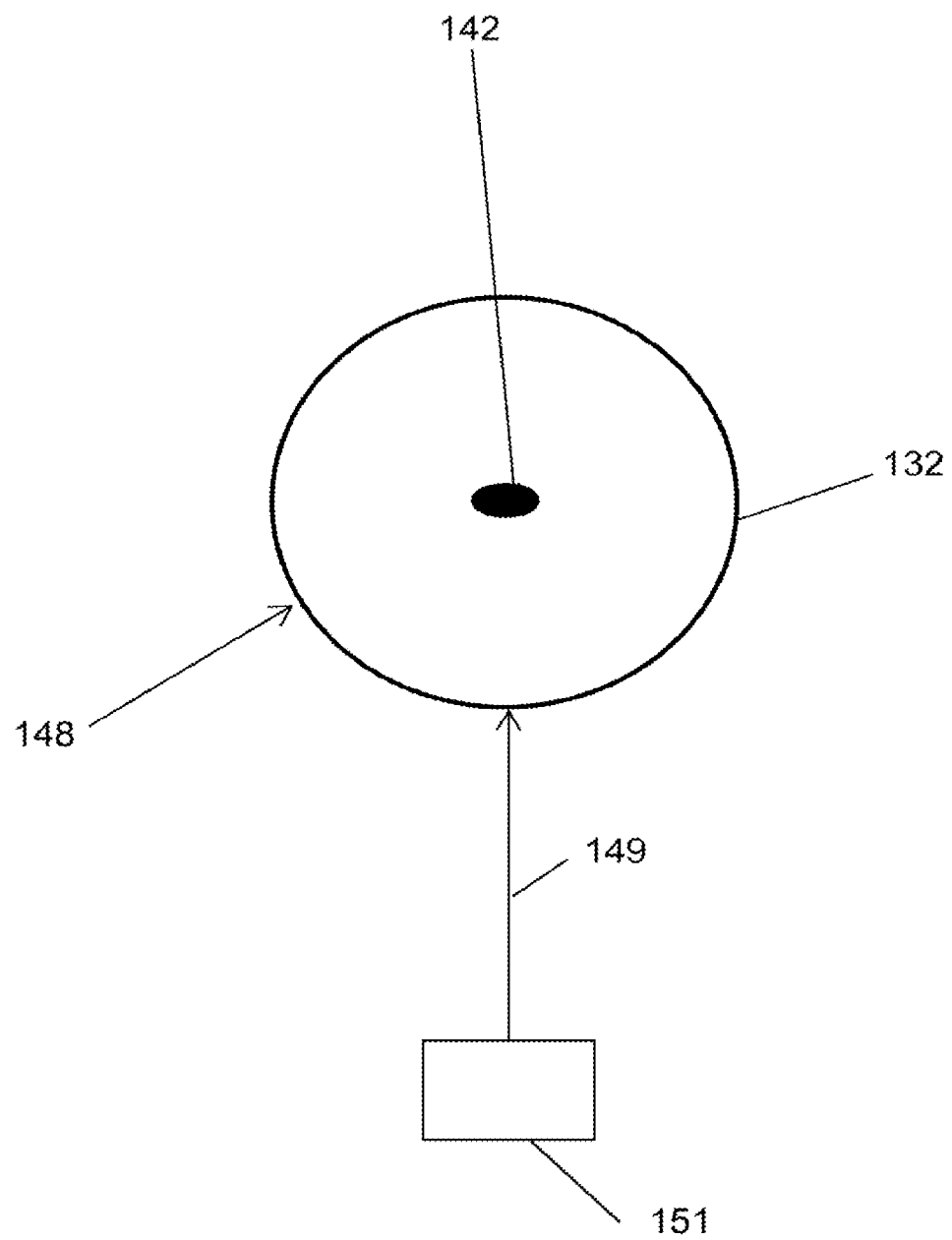
FIG. 9 is a schematic illustration of illumination of a sample at an interrogation region using a single illumination source illuminating at an angle orthogonal to the flow axis.

FIG. 9 illustrates an embodiment in which illumination of an analyte 142 at the interrogation region 148 at an angle orthogonal to the flow axis at the interrogation region 148, which is also orthogonal to the optical axis of the collector element (coaxially aligned with the flow axis in the vicinity of the interrogation region 148). In the embodiment depicted in FIG. 9, the illumination source 151 illuminates the interrogation region 148 directly. FIG. 9 illustrates the flow cell 132 at the interrogation region, with the optical axis of the collector element extending into and out of the page) extending into and out of the page. It is also contemplated that one or more optical elements may intervene between the illumination source 151 and the interrogation region 148 to direct the illumination at an angle orthogonal to the flow axis in the vicinity of the interrogation region 148. For example, a flat mirror at a 45° angle may direct the electromagnetic energy 90° from its path as emitted from the illumination source 151. Other angles and multiple mirrors may be used to divert the electromagnetic energy from the illumination source 151 to allow for more convenient and/or compact placement of the illumination source 151.

Figure 10:
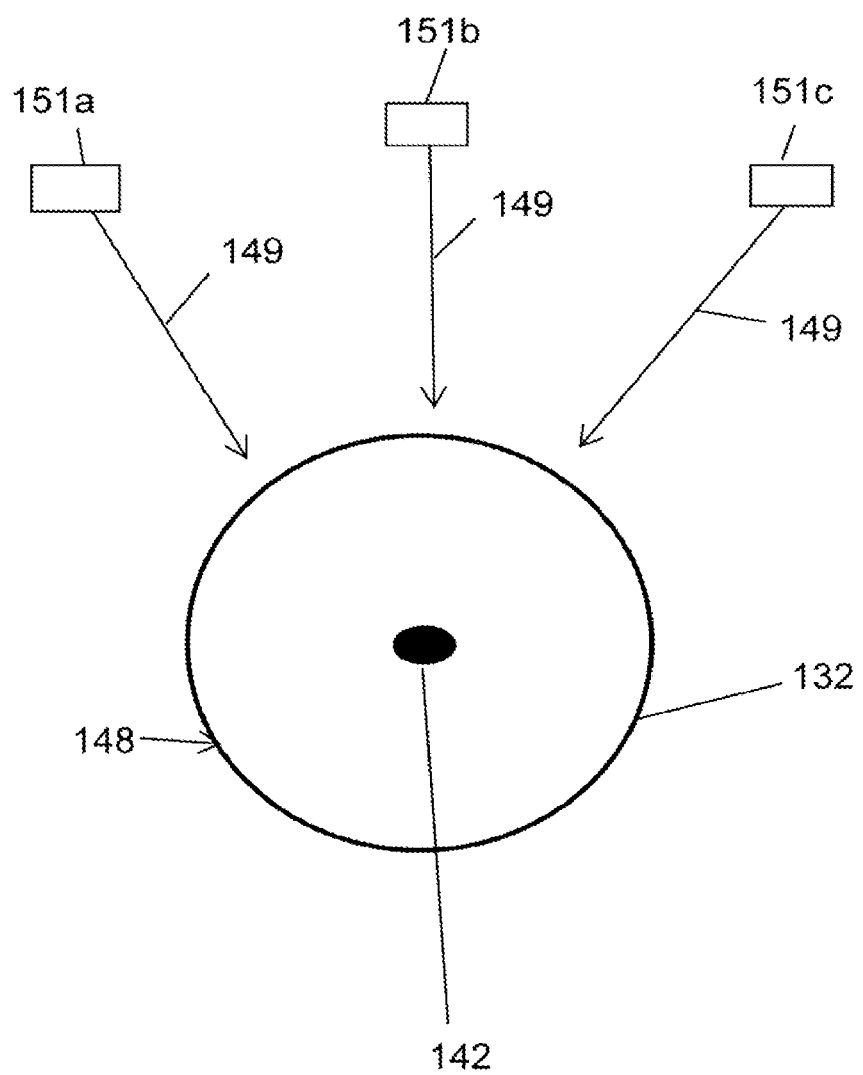
FIG. 10 is a schematic illustration of illumination of a sample at the interrogation region using multiple illumination sources illuminating at various angles in a plane orthogonal to the flow axis.

FIG. 10 illustrates an example of illumination (by beams of electromagnetic energy 149) of an analyte 142 at the interrogation region 148 at a plane orthogonal to the optical axis of the collector element (and consequently the flow axis in the vicinity of the interrogation region 148) using multiple illumination sources 151a, 151b, 151c. FIG. 10 illustrates the flow cell 132 at the interrogation region, with the optical axis of the collector element extending into and out of the page) extending into and out of the page. The one or more illumination sources may illuminate the sample from one or more directions, from angles of arc greater than 0° to less than 360° over a plane substantially orthogonal to the flow axis at the interrogation region. For example, axisymmetric illumination of the sample at the interrogation region 148 may be achieved using multiple illumination sources at angles distributed about the axis of flow at the interrogation region. For example, and without limitation, three illumination sources may be arranged at 90° (orthogonal to) the axis of flow at the interrogation region 148, 100°, 140°, and 120° degrees from each other. As used herein, such illumination is considered axisymmetric as there is rotational symmetry of the illumination about the optical axis of the collector element. In some embodiments, four illumination sources may be used to directly illuminate the interrogation region from directions offset by 90°. Any suitable number of illumination sources may be used.

In other embodiments, the one or more illumination sources may illuminate the sample from one or more directions, from angles of arc greater than 0° to less than 360° over a plane angled at any angle relative to the flow axis at the interrogation region 148. For example, the interrogation region 148 may be illuminated from an angle oblique to the flow axis (coaxially aligned with the optical axis of the collector element).

For example, 1, 2, 3, 4, 5, 6, 7, 8, 9, 10, or more illumination sources may be used. Embodiments employing multiple illumination sources may exhibit high signal strength and moderate specificity, while minimally impacting the collection of emitted, transmitted, or reflected electromagnetic energy by the collector element. One or more holes, gaps, or openings may be provided in the collector element to allow for illumination in multiple directions from multiple illumination sources.

Figure 11:
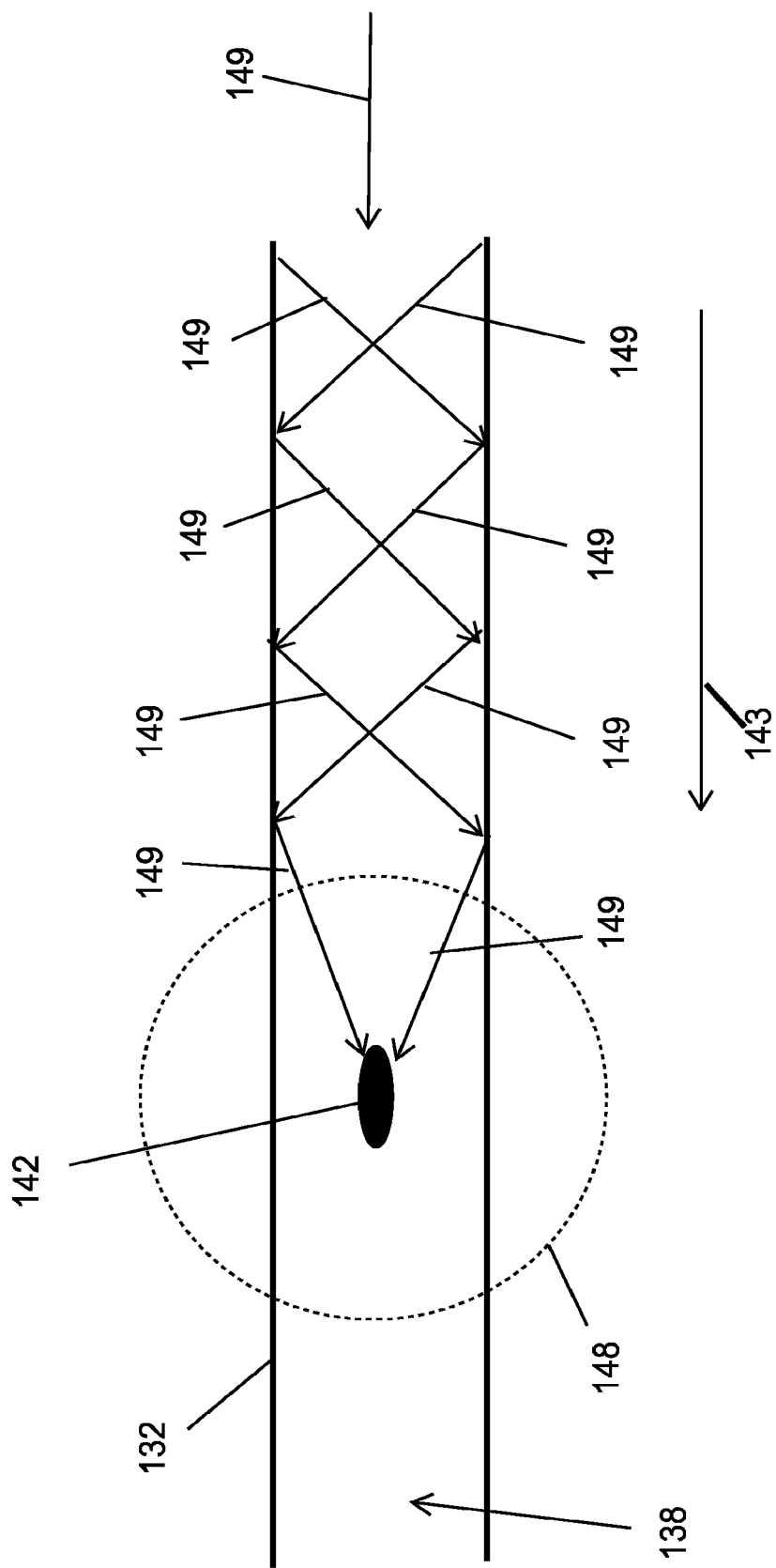
FIG. 11 is a schematic illustration of illumination of a sample at the interrogation region using the flow cell as a waveguide to direct the illumination onto the interrogation region.

Referring to FIG. 11, in some embodiments, the flow cell 132 may be used as a waveguide for illumination along at least portion of the flow cell 132, for example, the portion passing through the interrogation region 148. The illumination source 151 (not shown in FIG. 11) is focused on, or the electromagnetic energy from the illumination source 151 is directed using one or more optical elements to be focused on, an opening or translucent portion of the flow cell 132.

For example, an arc lamp may be used as the illumination source 151. The flow cell 132 relays the electromagnetic energy 149 through the flow cell 132 to the interrogation region 148, thereby illuminating an analyte 142 in the interrogation region 148. A capillary tube-type flow cell is particularly useful in such embodiments. Illumination through the capillary tube is advantageously insensitive to misalignment, is relatively easy to align, and provides uniform illumination of the analyte at the interrogation region 148, as there is little variation of intensity within the waveguide.

Figure 12:
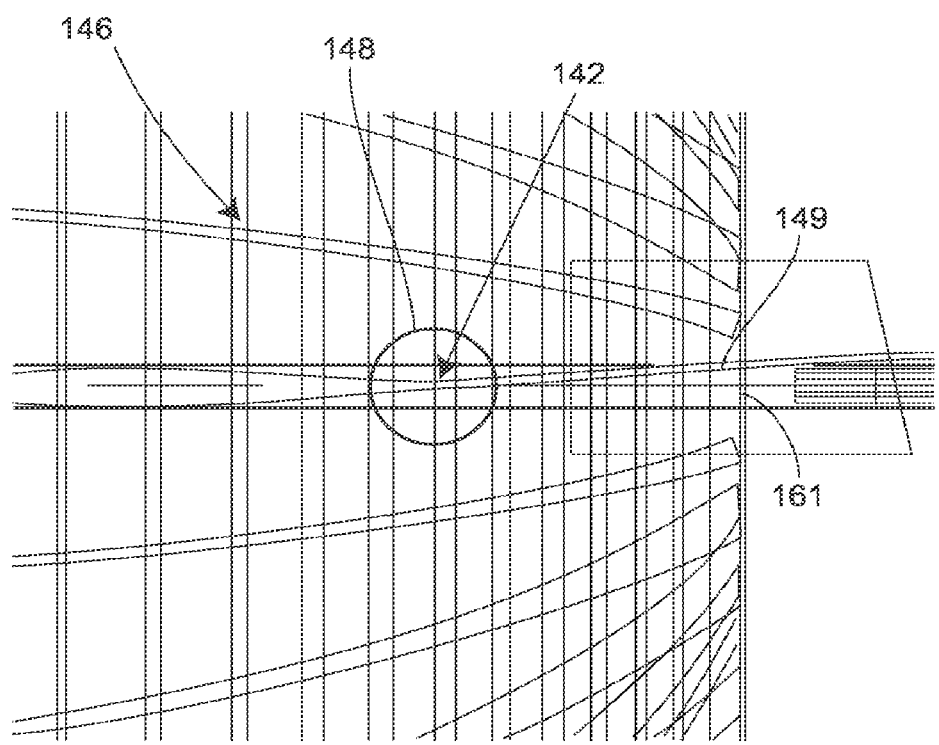
FIG. 12 is a schematic illustration of illumination of a sample at the interrogation region using slightly off-axis illumination.

FIG. 12 illustrates an embodiment in which the electromagnetic energy 149 illuminates the sample slightly off-axis relative to the flow axis of the sample in the vicinity of the interrogation region 148, which is coaxially aligned with the optical axis of the collector element 146.

Figure 13:
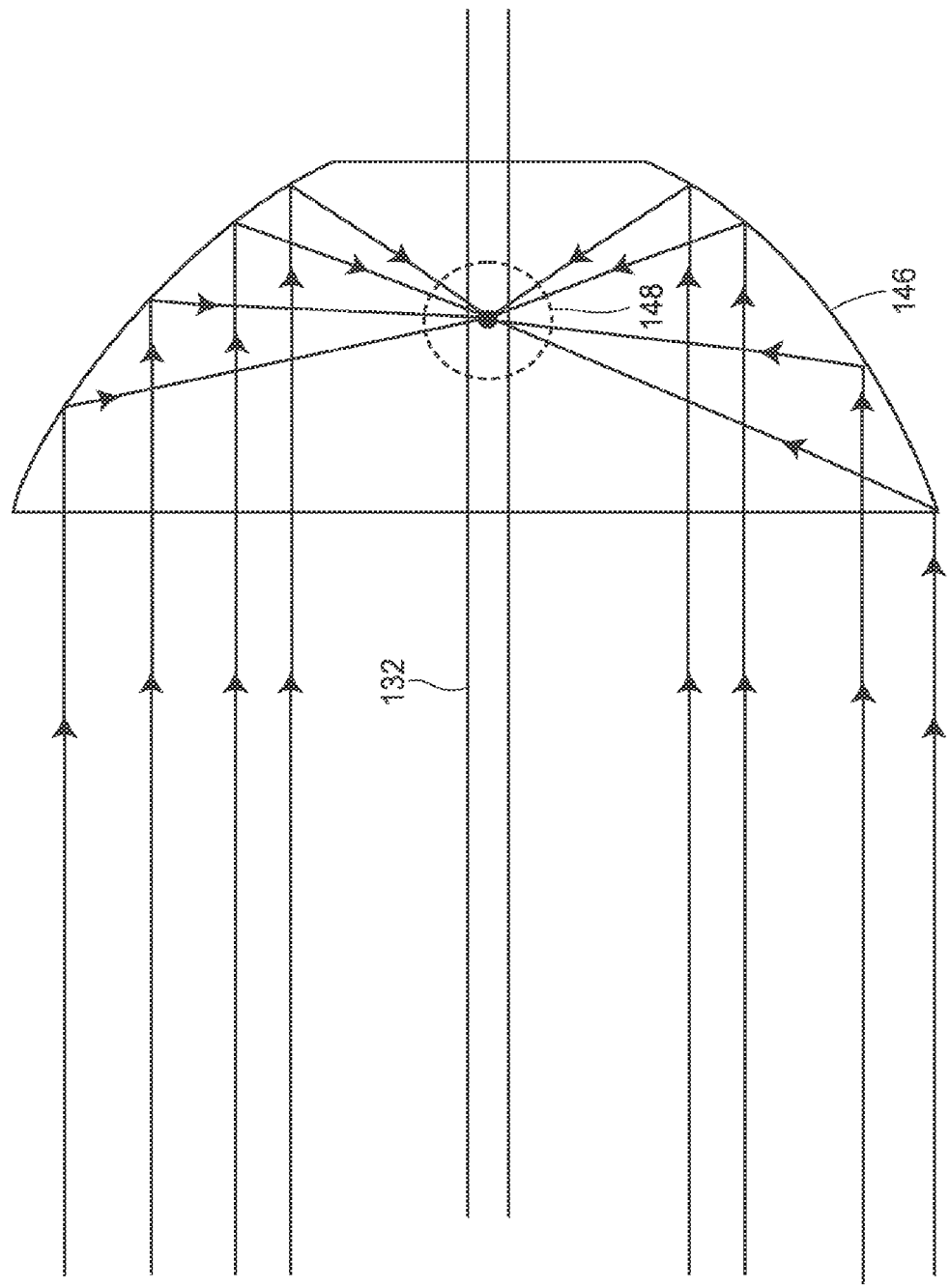
FIG. 13 is a schematic illustration of an embodiment of the disclosure in which the collector element also functions to focus the electromagnetic energy onto the interrogation region.

In other embodiments, one or more illumination optical elements and/or the collector element 146 may be used to direct and focus the electromagnetic energy from the illumination source 151 on the interrogation region 148. Referring to FIG. 13, the concave collector element 146, in some embodiments, may serve as both an optical element for illumination and a collection element. In such embodiments, the collector element 146 receives electromagnetic energy 149 from the illumination source 151 or from another optical element and focuses the electromagnetic energy 149 onto the interrogation region 148. In various embodiments, the concave collector element 146 may be the only optical element focusing the electromagnetic energy from the illumination source 151. In other embodiments, the collector element 146 may be a part of an optical arrangement and may serve as the final optical element for focusing the electromagnetic energy 149 onto the interrogation region 148.

Figure 14:
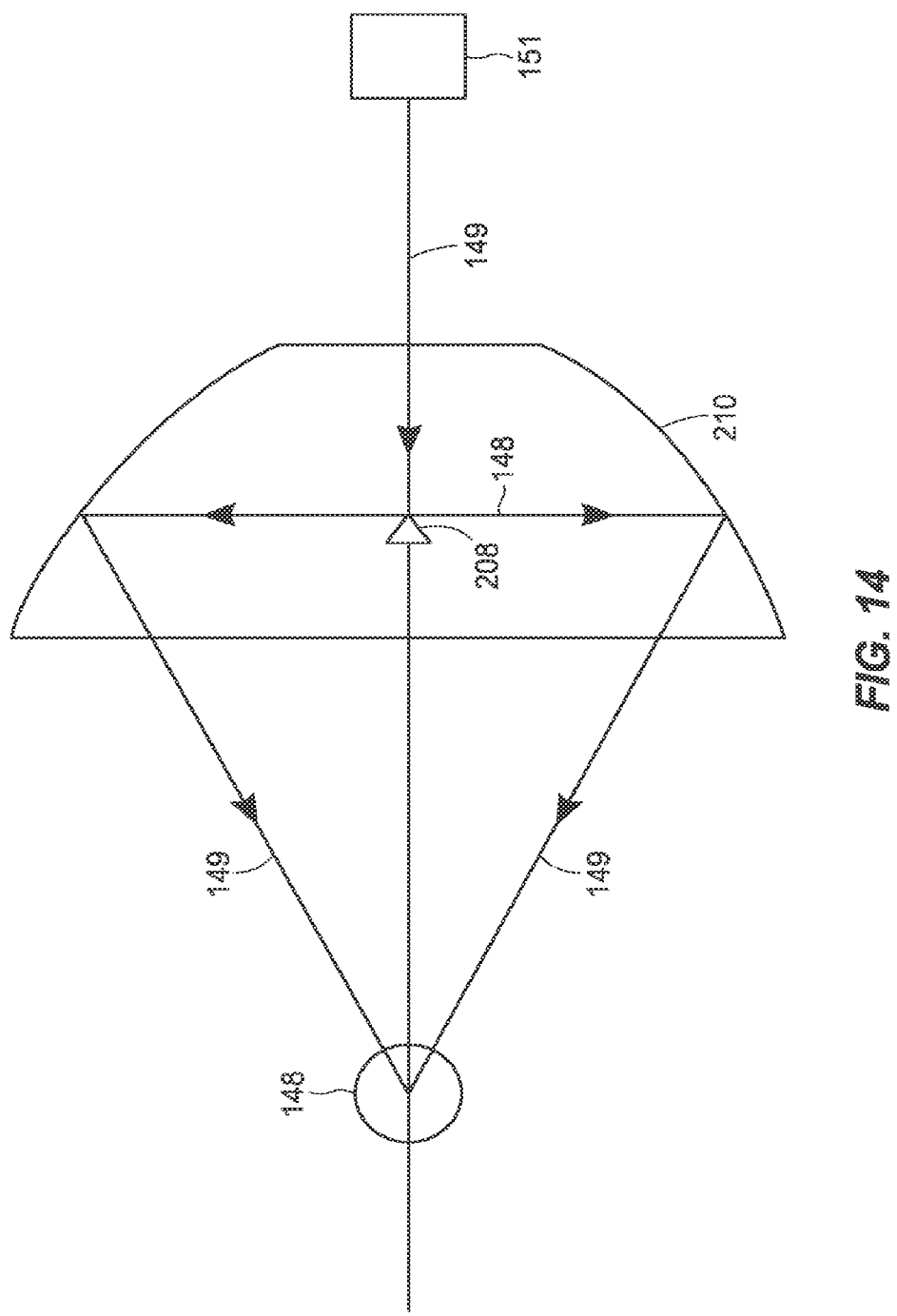
FIG. 14 is a schematic illustration of illumination of a sample at an interrogation region using a conical optical element and a concave optical element in accordance with an embodiment of the disclosure.

Referring to FIG. 14, in various embodiments, the illumination source 151 may be focused on a conical optical element 208, which transmits light to a concave optical element 210 or to the concave collector element 146 serving as an optical element. The concave optical element 210 focuses a ring, a cone, or other arbitrary shape of electromagnetic energy about the interrogation region 148. In some instances, the electromagnetic energy is focused rotationally symmetric about the interrogation region 148. In yet other instances, the electromagnetic energy is focused axisymmetrically about the interrogation region 148. This optical arrangement may further include a flat optical element (not shown) for further focusing of the electromagnetic energy from the concave optical element 210, if needed or desired.

The concave optical element 210 may, in some embodiments, be a ring-shaped optical element having a generally concave shape. Any other suitable shapes, such as paraboloids, conically shaped elements, hyperboloids, ellipsoids, and spheroids may be used as the concave optical element in this or any of the following optical arrangements. Other shapes, including, but not limited to, some surfaces of or related to the general mathematical form of equations of the second degree in three dimensions, e.g., $f(x, y, z) = ax^2 + by^2 + cz^2 + 2fyz + 2gxz + 2hxy + 2px + 2qy + 2rz + d = 0$ may also be used as the concave optical element. Unless otherwise specified, the terms "concave optical element," "first concave optical element," and "second concave optical element" should be understood throughout the disclosure as referring generally to all potential embodiments of the concave optical element. It will be understood, herein, that a concave optical element may be considered, for example, generally ellipsoidal or otherwise shaped despite disruptions or gaps in the wall of the optical elements. For example, in some embodiments, the concave optical element may include an opening at a vertex and/or at the sidewall of the optical element. For example, a ring-shaped optical element may be generally considered to be an ellipsoid, paraboloid, hyperboloid, or spheroid based on the general shape of the ring if the missing walls were provided. In some embodiments, the concave optical element is a mirror for reflecting the electromagnetic radiation to the desired location.

In the foregoing or any of the following embodiments utilizing a conical optical element 208, the conical optical element 208 may have any suitable base shape and may be a right cone or an oblique cone. The arrangement of the conical optical element 208 relative to the concave optical element 210 is dependent upon the shape of the concave optical element 210 and the shape (right or oblique) of the conical optical element 208. Arrangement of the conical optical element 208 and the concave optical element 210 to achieve transmission of a plane, ring, or any arbitrary shape of light may be achieved by placement of the conical optical element 208 relative to a point within the internal volume of the concave optical element 210, as is known in the art. The conical optical element 208 may be aligned along the optical axis of the concave optical element 210. For example, in some embodiments, the conical optical element 208 is coincident with the focal point of the concave optical element 210. In other embodiments, the conical optical element 208 may be displaced relative to the focal point of the concave optical element 210 either towards or away from a vertex of the concave optical element 210. In some embodiments, flat mirrors may be used to divert the illumination from the conical optical element 208 to the concave optical element 210 such that the conical optical element 208 need not be aligned coaxially with the concave optical element 210. The illumination source may be coaxially aligned with the conical optical element 208. In embodiments where the concave optical element 210, the conical optical element 208, and the illumination source 151 are coaxially aligned, the concave optical element 210 may include a gap or opening at the vertex to allow for unobstructed passage of the electromagnetic energy from the illumination source 151 to the conical optical element 208. Alternatively, the illumination source 151 may be misaligned relative 151 to the optical axis of the conical optical element 208 and one or more flat optical elements may be used to deflect the electromagnetic energy to the conical optical element 208. In such embodiments, the concave optical element 210 may also include a gap or opening at the vertex to allow for unobstructed passage of the electromagnetic energy.

Figure 15:
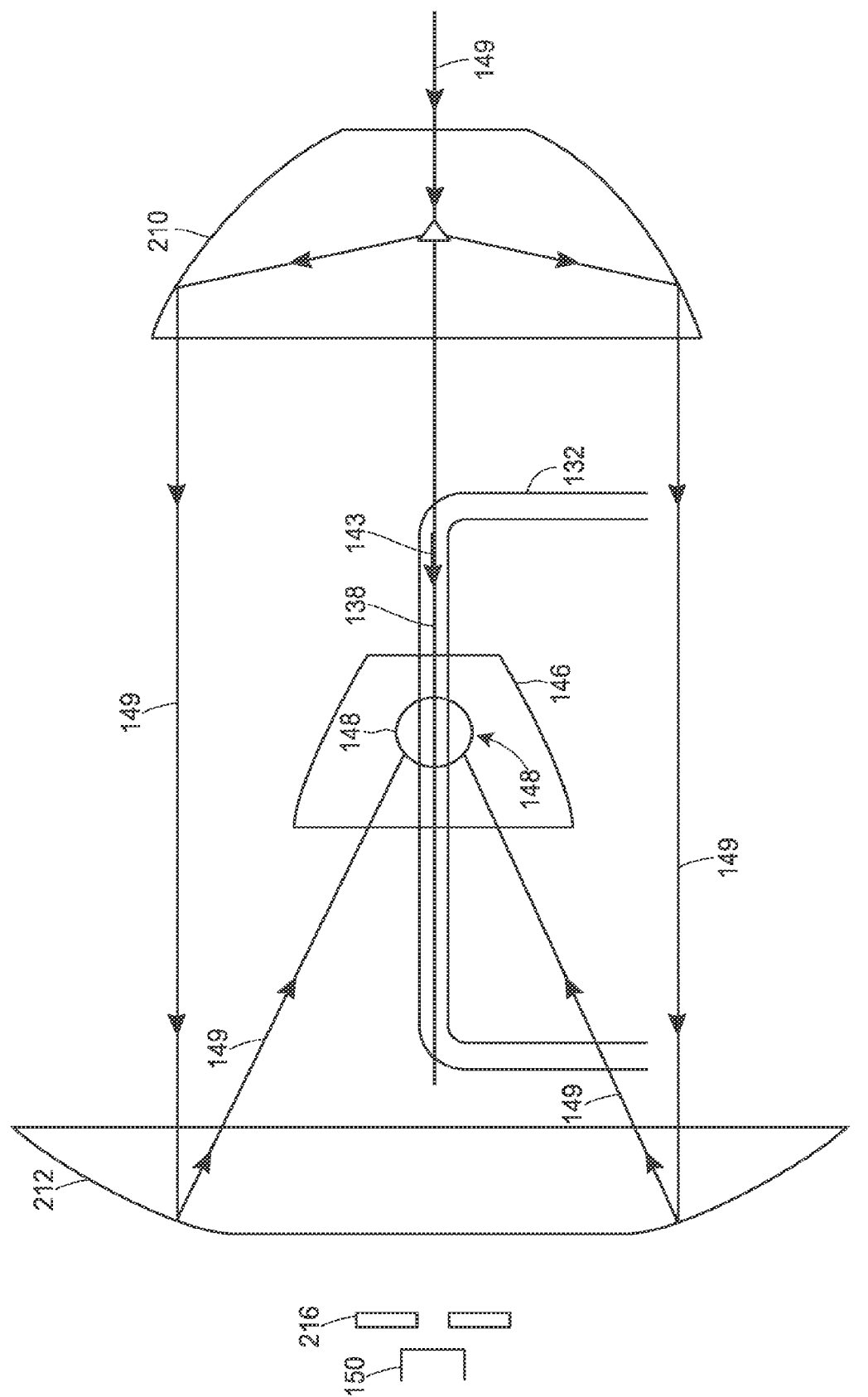
FIG. 15 is a schematic illustration of illumination of a sample at an interrogation region using two concave optical elements and a conical optical element in accordance with an embodiment of the disclosure.

FIG. 15 illustrates an embodiment employing multiple concave optical elements to illuminate the sample. As illustrated in FIG. 15, the optical arrangement may be as described above with reference to FIG. 14, but may further include a second concave optical element 212. The electromagnetic energy 149 transmitted by or reflected from the first concave optical element 210 is directed to the second concave optical element 212 rather than being focused directly on the interrogation region 148. For example, the conical optical element 208 may be arranged relative to the first concave optical element 210 such that the concave optical element 210 transmits or reflects an annulus of electromagnetic energy 149 to the second optical element 212. The second concave optical element 212 then focuses the annulus of electromagnetic energy 149 as a cone on the interrogation region 148. The second concave optical element 212 focuses the electromagnetic energy 149 about the interrogation region. In some instances, the electromagnetic energy is focused rotationally symmetric, in yet other instances, the electromagnetic energy is rotationally symmetric about optical axis of the collector element (i.e., axisymmetric, with the relevant axis being the optical axis of the collector element). In some embodiments, as illustrated in FIG. 15, the first and second optical elements 210, 212 and the conical elements 208 are coaxially aligned with each other and with the concave collector element 146. In other embodiments, one or more of the optical elements may be misaligned with another one or more of the optical elements and/or the collector element 146 and flat optical elements may be used to direct the electromagnetic energy 149 to the desired region or optical element.

In some embodiments, the first and second concave optical elements 210, 212 are paraboloids and the collector element 146 is an ellipsoid. In such embodiments, the first parabolic optical element 210 receives electromagnetic energy 149 from the conical optical element 208 and reflects or transmits the electromagnetic energy 149 as an annulus to the second parabolic optical element 212. The second parabolic optical element 212 focuses the received electromagnetic energy 149 onto the interrogation region 148.

The first and second concave optical elements 210, 212 may have any suitable shape. For example, one or both of the first and second concave optical elements 210, 212 may be an ellipsoid, paraboloid, hyperboloid, or spheroid so long as the elements are arranged such that the second concave optical element 212 receives the electromagnetic energy 149 from the first concave optical element 210 and focuses the electromagnetic energy 149 on the interrogation region 148 or the collector element 146. As noted above, the collector element 146 may also function, in some embodiments, as an optical element to focus the electromagnetic energy 149 onto the interrogation region 148. In embodiments using first and second concave optical elements 210, 212, it is also contemplated that the electromagnetic energy 149 be transmitted or reflected from the second concave optical element 212 onto the concave collector element 146, which then focuses the electromagnetic energy 149 onto the interrogation region 148. The concave collector element 146 will also serve to receive and collect the detectable signal if an analyte is illuminated in the interrogation region 148.

In the embodiment depicted in FIG. 15, the flow cell 132 enters the optical arrangement between the first concave optical element 210 and the concave collector element 146, and then passes through an opening at the vertex of the collector element 146. However, other flow cell arrangements are also contemplated. For example, the flow cell 132 may enter the internal volume of the collector element 146 through a side wall or gap (not shown) in the side wall region of the collector element 146 and then turn to pass through the interrogation region 148 such that the portion of the flow cell 132 passing through the interrogation region 148 is coaxially aligned with the optical axis of the collector element 146. Any other arrangements of the flow cell 132 relative to the collector element 146 and optical elements may be used so long as the flow axis in the vicinity of the interrogation region 148 is coaxially aligned with the optical axis of the collector element 146 and a stable laminar or core-in-sheath type flow is established upstream of the interrogation region 148.

Figure 16:
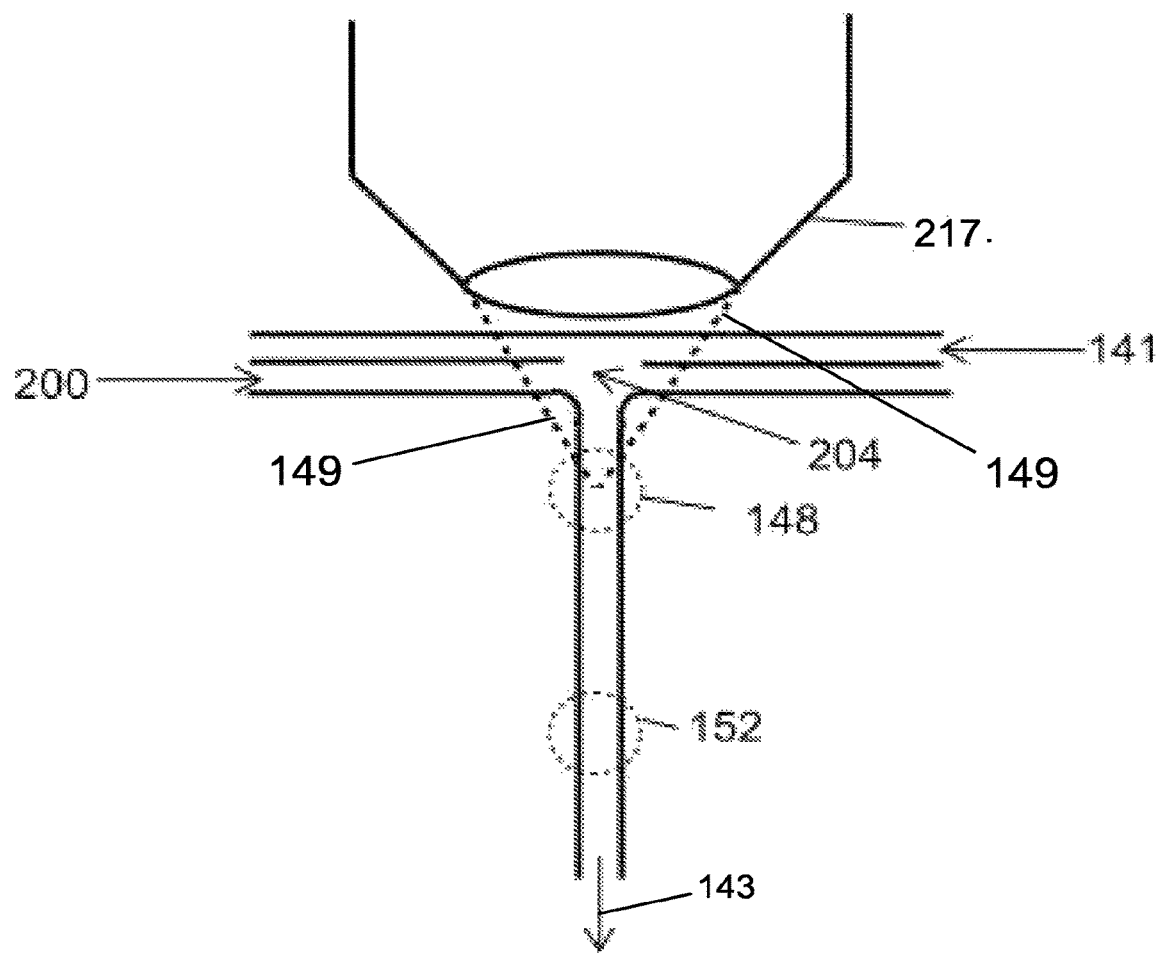
FIG. 16 is a schematic illustration of collection of a detectable signal from an analyte at an interrogation region using an objective lens as the collector element in accordance with an embodiment of the disclosure.
Figure 17:
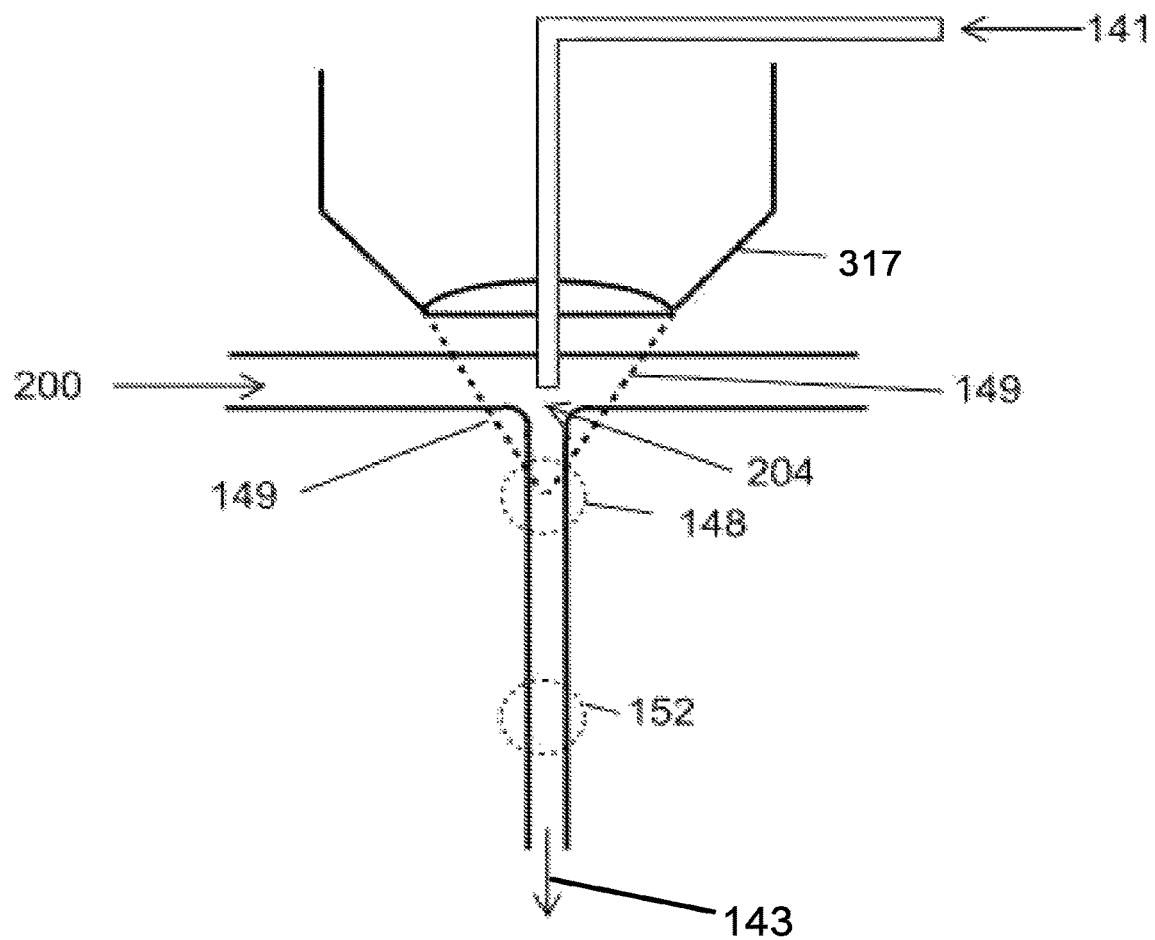
FIG. 17 is a schematic illustration of collection of a detectable signal from an analyte at an interrogation region using an objective lens as the collector element, the objective lens being modified to allow at least a portion of the sample flow to pass through the objective lens, in accordance with an embodiment of the disclosure.

In various embodiments, an objective lens may be used as an optical element for focusing electromagnetic illumination from the illumination source 151 onto the interrogation region 148. The objective lens may be coaxially aligned with the flow path 138 of the flow cell 132 in the vicinity of the interrogation region 148. In some embodiments, the sample may be directed to flow away from the objective lens. FIG. 16 illustrates an exemplary embodiment in which an objective lens 217 is used as a collector element and the sample flows away from the objective lens 217. In the embodiment shown in FIG. 16, hydrodynamic focusing is achieved from planar sample sources. However, other hydrodynamic focusing methods and apparatus may be used as described above. In the example depicted in FIG. 16, the sheath fluid 200 and the sample fluid 141 flow through the acceleration region 204 to generate a stable core-in-sheath flow upstream of the interrogation region 148. Referring now to FIG. 17, the objective lens 317 may be modified to allow for passage of a hydrodynamic focusing apparatus and/or the sample flow through the objective lens 317. In the embodiment depicted in FIG. 17, a flow path for introduction of the sample 141 passes through the modified objective lens 317.

Electromagnetic energy from the illumination source (not shown) is focused by the objective lens 217 or 317, or by another optical element, on the interrogation region 148. The objective lens 217 or 317 also acts as a collector element, having a focal point coincident with the interrogation region 148 and cooperating with one or more additional optical elements to direct energy emitted from the analyte in the interrogation region 148 to a detector. Such an arrangement advantageously allows for the use of the objective lens 217 or 317 without the need to divert the flow around the objection lens. This may advantageously provide for placement of the sorting region 152 further downstream of the interrogation region 148 than in conventional systems in which the flow must be diverted around the objective lens 217 or 317.

It will be appreciated that the embodiments illustrated in any of the foregoing optical arrangements may include additional components. In many embodiments, detectors, sorting energy sources, and flat mirrors for diversion of the electromagnetic energy may not be shown, but will be understood to be included in a suitable arrangement. Additional components may also include: optical components, such as those operable to module and/or attenuate an optical or other electromagnetic signal, to perform measurements based on a detected electromagnetic (e.g., optical) signal, to characterize a signal and/or a signal intensity; and fluidic components, such as those operable to cause a flow of sheath fluid or analyte, to measure a flow rate or flow volume, or to adjust a flow rate or flow volume.

Collection and Detection

The collector element 146 collects the energy (detectable signal) emitted or transmitted by and/or from the analyte 142, from an element within or on the surface of the analyte 142, or from a marker within or on the surface of the analyte 142. Any number of concave, reflective surface geometries may be employed as a collector element 146 to collect and/or focus the detectable signal received from the analyte 142 at the interrogation region 148 onto the detector 150, including paraboloid geometries, ellipsoidal geometries, and/or other shapes, including, but not limited to, some surfaces of or related to the general mathematical form of equations of the second degree in three dimensions, e.g., $f(x, y, z)=ax2+by2+cz2+2fyz+2gxz+2hxy+2px+2qy+2rz+d=0$. Unless otherwise specified, the term "collector element" should understood throughout the disclosure as referring generally to all potential embodiments of the collector element 146. Where a specific shape of a collector element 146 is contemplated (e.g., ellipsoidal, paraboloid, etc.), the phrase "collector element" will be preceded by an appropriate descriptor such as "paraboloid" or "ellipsoidal." It will be understood, herein, that a concave collector element 146 may be considered, for example, generally ellipsoidal or otherwise shaped despite disruptions or gaps in the wall of the collector element 146. For example, in some embodiments, the collector element 146 may include an opening at the vertex and/or in a sidewall of the collector element 146. For example, a ring-shaped collector element may be generally considered to be an ellipsoid, paraboloid, hyperboloid, or spheroid based on the general shape of the ring if the missing portions were provided.

Referring back to FIG. 3, by way of example only, the collector element 146 is generally concave having an interior volume 167. The collector element 146 also has an optical axis 161 and a focal point 163. The collector element 146 further includes a vertex 159. In some embodiments, the collector element 146 may have a ring or otherwise incomplete outer wall (e.g., generally forming a paraboloid, ellipsoid, or sphere). As used herein, "vertex" shall be understood to include those regions of the collector element 146 corresponding to a vertex regardless of whether the collector element 146 includes a wall or an opening at the vertex. For example, as shown in FIG. 3, a collector element 146 having a truncated shape is considered to have a vertex 159 where a physical vertex would be located if not for the truncation.

The optical axis 161 of the collector element 146 is coaxially aligned with the portion of the flow path 138 passing through the interrogation region 148. Additionally, the focal point FA of the collector element 146 is coincident with the interrogation region 148.

In some embodiments, the collector element 146 is coaxially aligned with one or more concave optical elements, such as the concave optical elements 210, 212. In other embodiments, one or more of the concave optical elements 210, 212 of an optical configuration may be aligned off-axis with respect to the optical axis 161 of the collector element 146 and one or more mirrors may be used to direct the reflected or transmitted electromagnetic energy 149 to the region of interest, for example, focused on the interrogation region 148.

In some embodiments, the collector element 146 may be coaxially aligned with the detector 150. In other embodiments, optical elements may be used to direct the collected detectable signal from the collector element 146 to the detector 150. For example, one or more flat mirrors may reflect, redirect, and/or focus the collected detectable signal to or on the detector 150.

Figure 18:
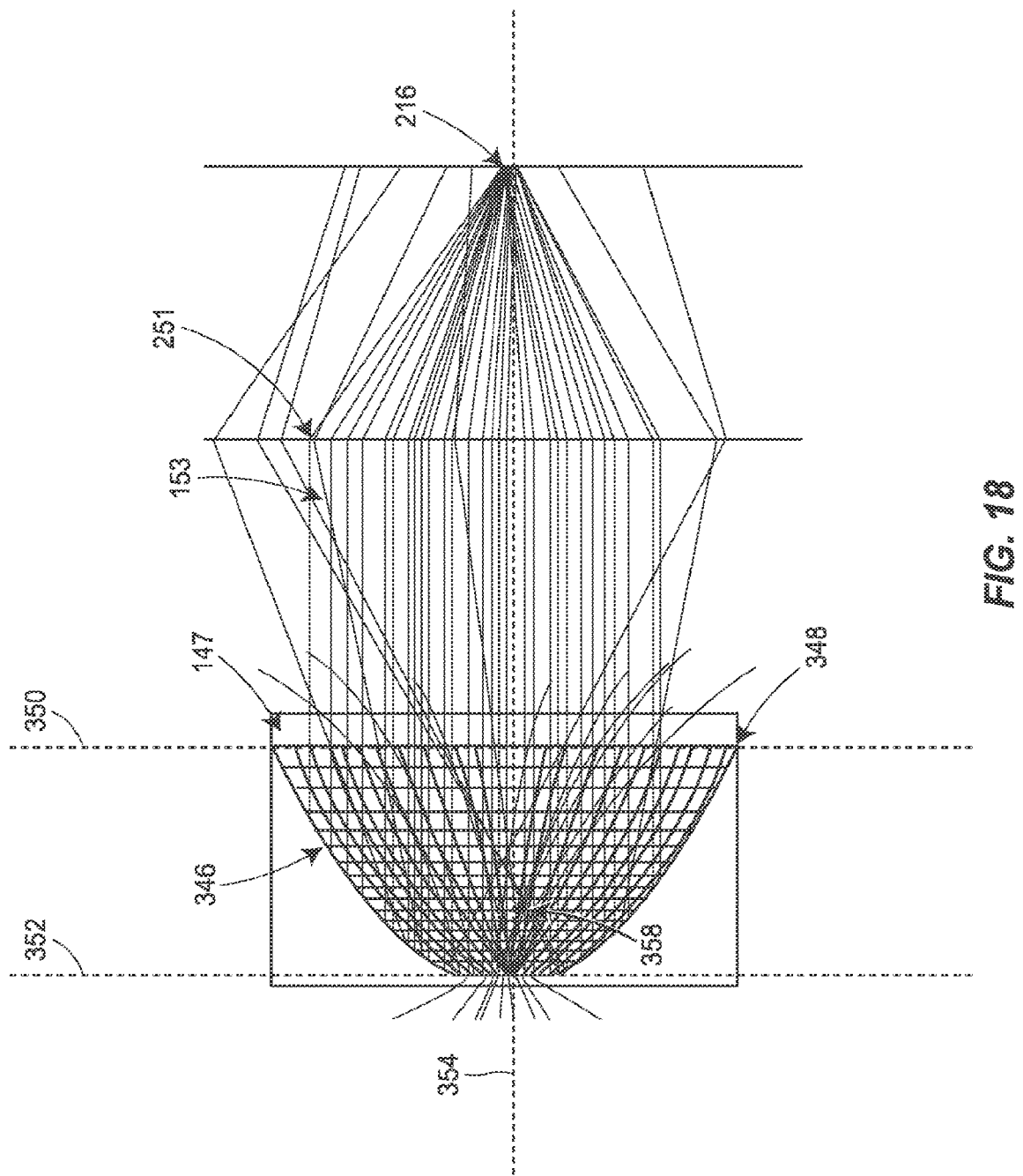
FIG. 18 is a schematic illustration of a parabolic collector element collecting the detectable signal from an analyte at the interrogation region in accordance with an embodiment of the disclosure.

Referring now to FIG. 18, use of the paraboloid collector element 346, for example, advantageously collects the detectable signal axisymmetrically from the analyte 142 with a very high numerical aperture. Additionally, a paraboloid collector element 346 exhibits high selectivity, being sensitive to the examined analyte and insensitive to other analytes and other sources of noise outside the focal point of the paraboloid collector element 346.

Referring still to FIG. 18, in some embodiments, the paraboloid collector element 346 may be a volume having an interior parabolic reflective surface 348 corresponding to the surface of a truncated circular paraboloid and, in particular, corresponding to the surface of a circular paraboloid truncated by first and/or second planes 350, 352 perpendicular to the axis 354 of the paraboloid. In some embodiments, electromagnetic energy from the illumination source 151 may enter the volume of the paraboloid collector element 346 passing through the first plane 350 prior to impinging on the analyte at the interrogation point 148 (i.e., at the focal point 358 of the paraboloid collector element 346), but does not fall incident upon the reflective surface 348 of the paraboloid collector element 346 prior to impinging on the analyte at the interrogation point 148. In other and/or additional embodiments, a detectable signal 153 collected by the paraboloid collector element 346 exits the paraboloid collector element 346 by passing through the first plane 350. In the embodiment depicted in FIG. 18, the detectable signal 153 passes through a paraxial lens 251 and a pinhole 216 before reaching the detector 150. The paraxial lens 251 and the pinhole 216 are optional and may be included when using any type of collector element to further focus the detectable signal 153 prior to detection. One or more such focusing elements may be particularly desirable when using a parabolic collector element 346 because the collected detectable signal is generally reflected as a parallel beam from a parabolic collector element.

The embodiment depicted in FIG. 18 illustrates a paraboloid collector element 346 filled with a medium to reduce diffraction effects on the detectable signal 153. The medium is represented by box 147. Filling the collector element 146 with a medium is discussed in detail below. It has been observed that a filled parabolic collector element 346 has a collection efficiency of about 68% at the focal point 358, while exhibiting a collection efficiency of only about 0.4% at 100 μm upstream of the focal point 358. Thus, the parabolic collector element 346 demonstrates high specificity as well as high collection efficiency. Misalignment of the flow axis through the interrogation region 148 relative to the optical axis of the collector element 346 may also decrease the collection efficiency of the collector element 346. Such arrangement, while not ideal, may be suitable for various embodiments. It has been observed that misalignment of the flow axis through the interrogation region 148 50 μm relative to the optical axis resulted in a collection efficiency of a parabolic collector element 346 of 34% and increased collection efficiency upstream of the interrogation region/point 148.

Referring to FIG. 19, in some embodiments, an ellipsoidal collector element 446 is employed to collect light from the interrogation point 148. The ellipsoidal collector element 446 may have any exterior surface shape, and is defined by a single, internal, on-axis ellipsoidal reflector surface corresponding to the surface of a truncated ellipsoid that may be formed by revolving an ellipse about its major axis. The ellipsoid may be truncated at a first point by a plane 450 defined by the minor axis of the ellipsoid or, alternatively, defined by a plane orthogonal to the major axis and disposed between the center point of the ellipsoid and the first focal point in the volume defined by the ellipsoidal collector element 446. In still another alternative, the ellipsoid may be truncated at the first point by a plane passing through the major axis of the ellipsoid and forming an acute angle with the plane defined by the minor axis of the ellipsoid. In some embodiments, the ellipsoid may additionally be truncated at a second point 452 between the first focal point 454 and the boundary of the ellipsoid defining the ellipsoidal collector element 446.

Like the paraboloid collector element 346, the ellipsoidal collector element 446 collects the detectable signal 153 axisymmetrically from the analyte 142 with a very high numerical aperture and exhibits high selectivity. Additionally, the ellipsoidal collector element 446 as described above advantageously reflects electromagnetic energy originating at the first focal point 454 toward a second focal point 456, which may correspond to the location of a pinhole 216 filtering unwanted electromagnetic energy (e.g., reflected illumination electromagnetic energy) from reaching a detector 150, without requiring an additional lens or mirror between the first focal point 454 and the pinhole 254. In some embodiments, the flow cell 132, which may be a tube containing a core-in-sheath flow such as that formed by a hydrodynamic focusing element, such as described above, may pass through a surface of the ellipsoidal collector element 446 and, in particular may pass through the ellipsoidal collector element 446 along its major axis between the first focal point 454 and the boundary of the ellipsoid defining the ellipsoidal collector element 446.

As with the embodiment depicted in FIG. 18, the elliptical collector element 446 is illustrated as filled with a medium (represented by box 147) to mitigate the refractive effects of the flow cell wall/air interface. It has been observed that a filled elliptical collector element 446 has a collection efficiency of about 68% at the first focal point 454 (coincident with the interrogation region 148), while exhibiting a collection efficiency of only about 0.003% at 100 μm upstream of the focal point 454. Thus, the elliptical collector element 346 demonstrates high specificity as well as high collection efficiency.

To reduce or eliminate the interference effects on the detectable signal resulting from the walls of the flow cell, the internal volume of the collector element 146 (e.g., the paraboloidal and ellipsoidal collector elements 346 and 446, respectively) may be filled with a medium having an index of refraction within a suitable tolerance of the index of refraction of the wall of the flow cell 132 at the interrogation region 148 such that diffraction of the energy of the detectable signal 153 resulting in a change in refractive index along the energy path is minimized or eliminated. The tolerance may be for example in a range of 0 to 0.1. Suitable mediums include, for example, materials well-known in the art as "refractive index matching fluids" or "refractive index matching oils". The filled collector element 146 may be used in combination with any of the hydrodynamic focusing methods and apparatus and optical arrangements described above. Further, the collector element 146 can be filled with a solid polymer matching the refractive index of the flow cell such that diffraction of the energy of the detectable signal resulting in a change in refractive index along the energy path is minimized or eliminated. Further, the flow cell may be manufactured in part within a solid material, for example as a channel passing through a solid material, and the collector element may be constructed integral to a surface portion of the solid material, for example as a concave (with respect to the interrogation region) optical element constructed on the outer surface of the solid material.

In other embodiments, the flow cell 132 includes an integrally formed spherical molding 154 at the interrogation region 148. The spherical molding 154 also reduces or eliminates interference in the detectable signal resulting from transmission of the light through the flow cell 132 wall. The detectable signal 153 emitted from, transmitted through, or reflected by the analyte generally impinges upon the spherical molding 154 at an angle orthogonal to the surface of spherical molding 154, thus mitigating or eliminating the effects of refraction as the light passes through the material-air (spherical molding surface-air) interface.

The spherical molding 154 may be formed of the same material as the flow cell 132 or, in an alternate embodiment, may be formed of a material having an index of refraction within a suitable tolerance of the index of refraction of the wall of the flow cell 132 at the interrogation region 148 such that diffraction of the energy of the detectable signal 153 resulting in a change in refractive index along the energy path is decreased or eliminated. The tolerance may be for example in a range of 0 to 0.1. The curvature of the spherical molding may be within a tolerance of about 0% to about 5%, about 1% to about 5%, about 2% to about 4%, and about 1% to about 3%. Other suitable tolerances include, for example, about 1, 2, 3, 4, and 5%. Additionally, centration of the spherical molding about the focal point of the collector element 146 may be within a tolerance of about 0 mm to about 5 mm, about 1 mm to about 4 mm, about 2 mm to about 3 mm, and about 1 mm to about 3 mm. Other suitable tolerances include, for example, about 0, 1, 2, 3, 4, and 5 mm.

The spherical molding 154 advantageously results in collection efficiencies of about 75% at the focal point of the collector element 146 and high selectivity on the order of a collection efficiency of about 0.00002% at a distance 50 μm upstream or downstream of the focal point. In such embodiments, the interrogation region 148 is advantageously very small and approaching collection at a single point.

Figure 20A:
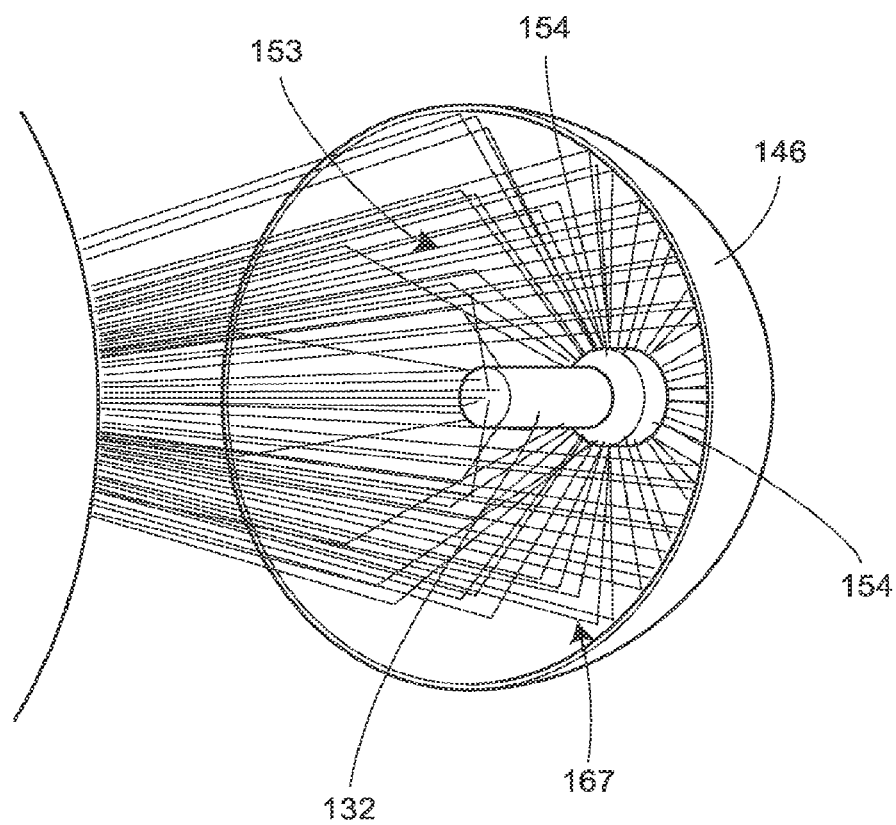
FIG. 20A is a schematic illustration of collection of a detectable signal emitted through a spherical molding on the flow cell, in accordance with an embodiment of the disclosure.
Figure 20B:
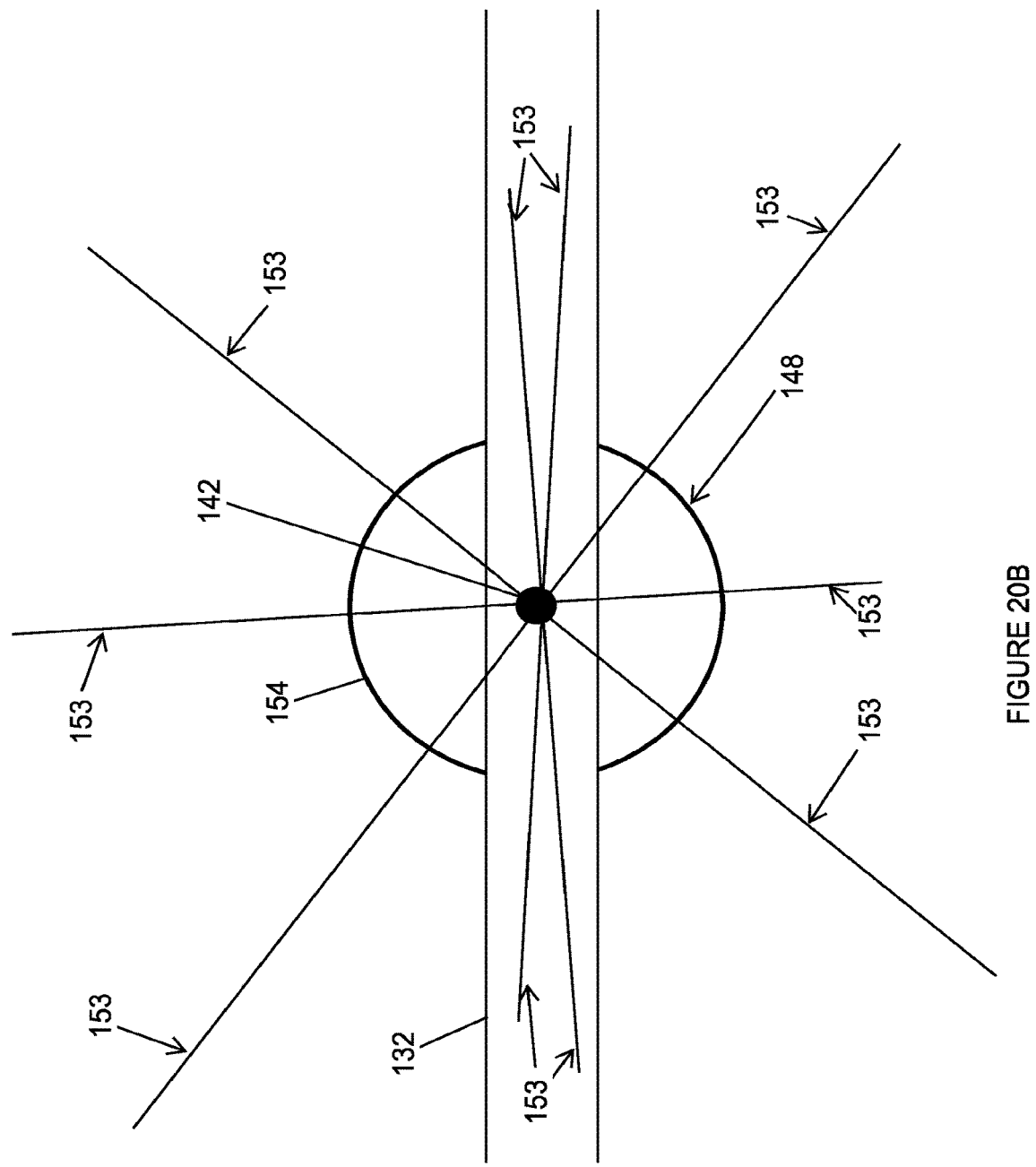
FIG. 20B is a zoomed in schematic illustration of FIG. 20A illustrating the detectable signal being emitted through the spherical molding.

FIG. 20A illustrates the spherical molding 154 and emission of the detectable signal 153 from the spherical molding 154 to the collector element 146 and transmission of the detectable signal 153 to the detector 150 or a flat optical element or pinhole 216 placed before the detector 150. FIG. 20B is a close up schematic of the emission of the detectable signal 153 through the spherical molding 154, demonstrating that the detectable signal 153 remains undisturbed by the molding wall.

In other embodiments, the refractive effects of the flow cell wall-air interface may be mitigated by making the flow cell wall at the interrogation region 148 thin. For example, the flow cell wall in the at the interrogation region 148 can have a thickness of about 20 μm to about 2000 μm, about 40 μm to about 1500 μm, about 60 μm to about 1000 μm, about 80 μm to about 800 μm, about 100 μm to about 600 μm, about 200 μm to about 400 μm, about 1000 μm to about 2000 μm, about 20 μm to about 50 μm, about 20 μm to about 80 μm, about 20 μm to about 200 μm, about 400 μm to about 1000 μm, or about 1500 μm to about 2000 μm. For example, suitable wall thicknesses can include about 20, 30, 40, 50, 60, 70, 80, 90, 100, 150 200, 250, 300, 350, 400, 450, 500, 550, 600, 650, 700, 750, 800, 850, 900, 950, 1000, 1100, 1200, 1300, 1400, 1500, 1600, 1700, 1800, 1900, and 2000 μm. Collection efficiencies for embodiments having thin flow cell walls at the interrogation region 148 without other mitigation elements (such as a filled collector or the spherical molding 154) may demonstrate collection efficiencies of up to about 50% at the focal point of the collector element 146 and about 3% at about 100 μm upstream of the focal point of the collector element 146.

Figure 26:
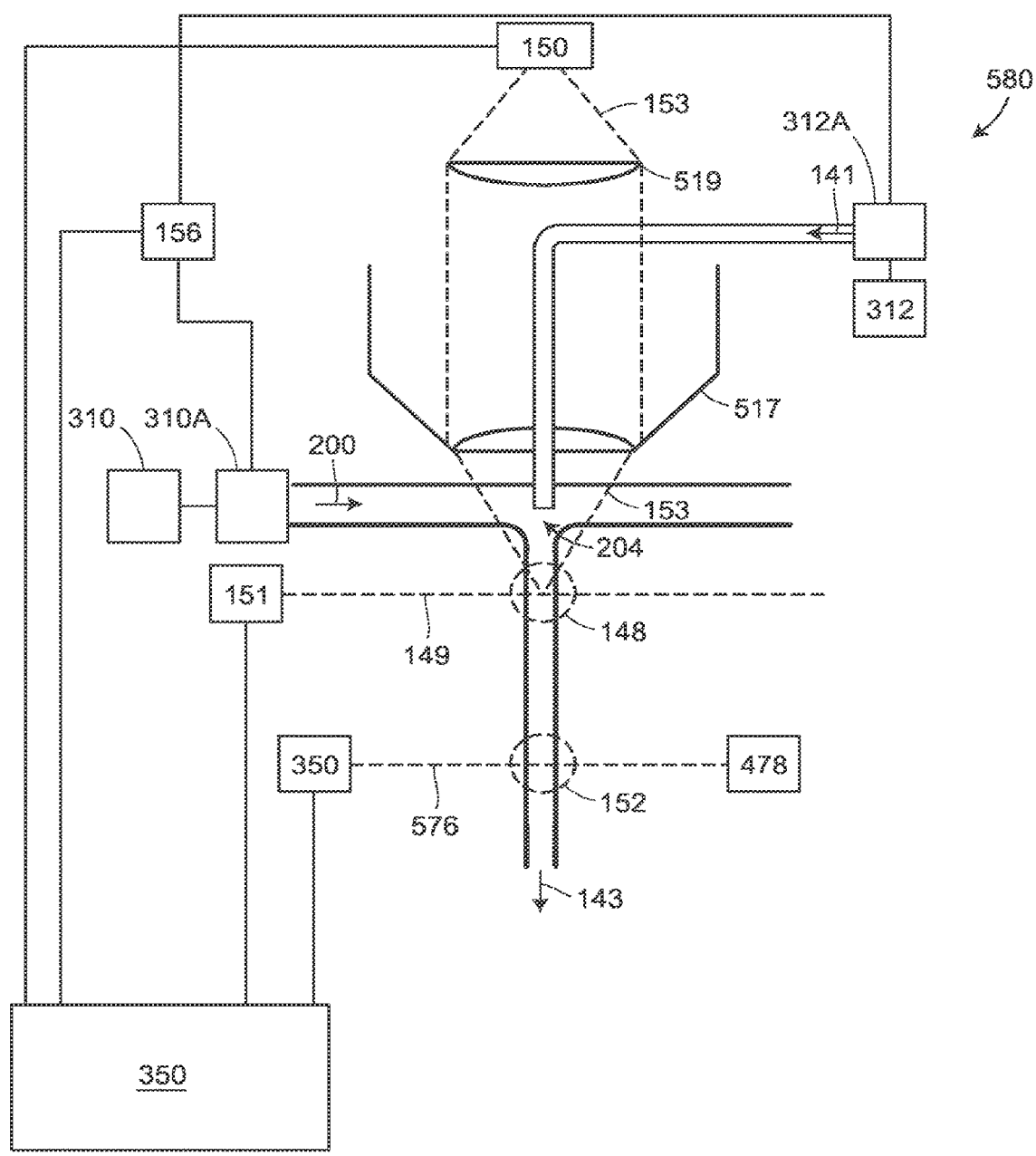
FIG. 26 is a schematic illustration of an exemplary system for detection of an analyte in accordance with another embodiment of the disclosure.

Referring to FIG. 26, the collector element can be, for example, an objective lens 517, with the focal point of the objective lens being coincident with the interrogation region 148. The detectable signal is collected by the objective lens and transmitted as an annulus to another lens 517 to or other focusing element that focuses the detectable signal 153 onto the detector 150. As described above with respect to FIGS. 16 and 17, in some embodiments, the objective lens can also be used for illumination of the sample. In other embodiments, the objective lens can be used for collection and illumination can be achieved using any of the above-described methods, including, for example, illumination from an illumination source orthogonal to the interrogation region 148, as illustrated in FIG. 26.

In various embodiments, the apparatus may further include the pin hole 216 or flat optical element, for example a dichroic mirror, aligned with the detector 150 to focus the collected detectable signal 153 prior to detection by the detector 150.

Sorting

In some aspects of the described methods and apparatus, a sorting cytometer utilizes a technique that physically and/or functionally modifies selected cells in populations to permit their differentiation. That is, instead of relying on immediate separation of cells by position, location, vessel, or time, the described embodiments instead provide cells are that inactivated, incapacitated, disrupted, disarticulated, fragmented, or otherwise altered (i.e., "modified") with respect to some desired property, which property optionally allows separation or differentiation of subpopulations in the preparation. The nature of the modification depends, all or in part, on an intended application or use for identified cells, and thus, characteristics of the identified cells that are relevant in the application. For example and for purposes of explanation or clarification only, a malignant or otherwise immortal or rapidly growing cell might be considered functionally inactivated in the context of the preparation of normal somatic cells if the cell's capacity to reproduce is negatively affected or if the cell is killed. In another example, again for purposes of explanation or clarification only, where an application requires the removal from a population of a subpopulation of cells that produce an undesirable protein or other substance, a sorting cytometer may achieve this result by abrogating production of the substance in these cells, by killing the cells, and/or by modifying the cells to permit their physical removal from the population.

The methods and apparatus presently described utilize, in some embodiments, an energy source for modification of cells or for the induction or initiation of processes such as chemical activation that may modify cells. Modifications induced by the energy source include in various aspects, direct effects on the cells, including but not limited to the modification of cellular components or chemicals including proteins, DNA, and substances involved in cellular metabolism; disruption, heating, cavitation, or explosions occurring in or near the cells; permeabilization or perforation of cells; and destruction, fragmentation, or morphological alteration of cells, including cells, viruses, bodies or particles. In other embodiments, modifications also or alternatively include indirect effects of the energy source, mediated by the energy source or by other factors, including chemical activation and/or deactivation, chemical crosslinking, or chemical derivitization of the cells or of one or more cellular components, the activation and/or deactivation of one or more chemical agents in or near the cells that cause the binding or association of such agents or their derivatives to the cell or its components, or the induction of altered functioning of the cells. In certain embodiments, chemical agents that react upon irradiation with the cells are normally present in the cells or in the application, or they are added as part of the method.

In some embodiments, the described methods and apparatus incorporate the use of photoactivatable compounds that are induced to bind or associate with cells or cellular components upon irradiation with light of an appropriate intensity and energy. Such compounds in certain aspects induce sufficient crosslinking or denaturation of one or more cellular components that affect cellular processes or metabolism of cells of interest. Alternatively, such compounds in certain aspects induce sufficient crosslinking or denaturation of one or more cellular components that kill cells of interest. In another alternative, photoactivatable compounds used in the described methods and apparatus bind to selected cells and alter one or more properties of cells of interest in such a way as to render the cells of interest amenable to identification and/or enrichment and/or depletion in subsequent processes. Cells of interest that have been altered by chemical derivatization, such as the addition of a chemical substance, are in certain aspects removed, concentrated, or purified in a subsequent step by methods that utilize the properties or interactions of such a substance. For example, and for purposes of explanation and clarification only, cells of interest are, in one aspect, derivatized by the addition of a substance that is subsequently bound by an antibody that permits the capture or retention of the derivatized cell of interest by various means. Many such substances are contemplated, and in one aspect, such substances include a class of compounds containing or related to the 2,4-dinitrophenyl group (DNP), which in one aspect is recognized and specifically bound by antibodies recognizing DNP. Accordingly, photoactivatable derivatives of DNP or related compounds are used in one aspect to derivatize cells of interest in an application of this type. Alternatively, derivatized cells of interest are captured or removed using strategies that cause the derivatized cells of interest to bind preferentially to certain substrates. For example and for purposes of explanation and clarification only, cells of interest derivatized using compounds containing or related to biotin are in one aspect captured or retained on substrates, surfaces, substances, media, compounds, or particles that bind or have been modified to bind biotin, for instance by the presence of avidin, streptavidin, biotin-binding antibodies, or other biotin-binding molecules. In another alternative related to this aspect, photoactivatable derivatives of biotin or related compounds are used to derivatize cells of interest in such an application. Alternately in other aspects, cells of interest are altered by the addition or association of chemical substances or compounds before being subjected to selection and modification. In such a case, therefore, an embodiment of the methods and apparatus described herein utilizes alteration of the added substance on selected cells to permit the differentiation of such cells from others in the population. For instance, and for purposes of explanation and clarification only, in one aspect all cells in a population are derivatized by the addition of a photolabile chemical compound before analysis, and in one aspect, specific cells are targeted for modification using the energy source of the apparatus to modify the photolabile chemical compound on those cells.

After illumination, the analyte, if present, flows from the interrogation region 148 to the sorting region 152. Due to the predictable and stable core-in-sheath or laminar flow, it is possible to know for each analyte its position for some distance after the analyte exits the interrogation region 148 and flows towards the sorting region 152. In some embodiments, a sorting energy source 350 (depicted in FIG. 22) may be controlled to irradiate the analyte or a portion of the analyte in the sample at the sorting region to disable, modify, or destroy the analyte.

In other embodiments, the sample may include first and second analytes, which may be differentially detected using the methods and apparatus described herein. Sorting of the first and second analytes may be achieved, for example, by irradiation of the first or second analyte after detection. For example, the detector 150 may be configured to detect and determine whether a detectable signal 153 is from the first or second analyte. Upon detection of the particular analyte, for example, the second analyte, for sorting, the sorting energy source 350 may be controlled to irradiate the second analyte to disable, modify, or destroy the second analyte.

In some embodiments, the sorting energy source 350 may be aligned to irradiate the sample orthogonally to the flow path 138 at the sorting region 152. In other embodiments, the sorting energy source 350 may be aligned to irradiate the sample at an oblique angle relative to the sorting energy.

In some embodiments the sorting energy source 350 is a laser emitting electromagnetic energy, for example, ultraviolet light, visible light, and infrared light.

For example, the sorting energy source 350 may be a UV laser. UV wavelengths of less than about 350 nm may be absorbed by nucleic acids, proteins, and/or dyes used to absorb light and may transfer the energy to a region of the analyte (e.g., a cell) resulting in modification, damaging, or killing of the cell.

The sorting energy source 350 may be, for example, a visible/infrared laser. Visible/infrared wavelengths of about 775 nm and above may be absorbed by cellular constituents and/or dye used for absorbing light and/or water and may transfer the energy to a region of the analyte (e.g., a cell) resulting in modification, damaging, or killing of the cell.

The sorting energy source 350 may be, for example, a visible laser. Visible wavelengths of 350 nm to about 775 nm may be absorbed by cytochromes and/or dye used for absorbing light and/or water may transfer the energy to a region of the analyte (e.g., a cell) resulting in modification, damaging, or killing of the cell.

In embodiments where the analyte is a cell and sorting is to be achieved by death of the cell, the sorting energy may be selected to heat the internal temperature of the cell to about 70° C. Such heating may be achieved, for example, with an instantaneous power of about 50 W. Sources capable of killing a cell include, for example, a laser diode array, low duty cycle pulsing, and modulated continuous or quasi-continuous energy source of appropriate wavelength or power.

Any of these or other known sorting energy sources 350 may be used for killing, modifying, or damaging the analyte at the sorting region 152. The sorting energy source 350 may damage a cell in variety of ways including, for example, disruption of membranes or other cellular organelles or components, denaturation of biomolecules in cells, and crosslinking or displacement of biomolecules. Disruption of membranes or other cellular organelles or components may be achieved by cavitation of water within the cell and damage to proximal cellular components or by energy-induced dissociation of water or biomolecules in the cell. Denaturation of biomolecules and crosslinking or displacement of biomolecules results in associated changes in or loss of function of the biomolecules and/or the cells.

Upon detection of an analyte or an undesirable analyte, the sorting energy source 350 may be engaged, or its output modulated or redirected, to target the analyte. Sorting using the sorting energy source 350 is achieved by modifying, disabling, or destroying the analyte. The sorting energy source 350 may damage, modify, or disable an analyte in a sample in a variety of manners including, for example, causing cavitation of the sample fluid in the region of the analyte (at the sorting region), causing heating of the sample fluid in the region of the analyte (at the sorting region), causing molecular breakdown and/or cross-linking within the analyte, and causing chemical modification of the analyte either directly or by inducing chemical reagents within the sample fluid to bind to the analyte.

In some embodiments, the sorting energy source 350 may be a source of heat, such as a heating element, microwaves, or electric discharge. The sample is sorted in the sorting region 152 by heating of the fluid around the analyte at the sorting region 152 to damage, modify, or destroy the analyte.

In some embodiments, sorting may be achieved using electroporation or through forces exerted on the sample at the sorting region. The force may be, for example, ultrasound.

Sample Collection after Detection and Sorting

Figure 21A:
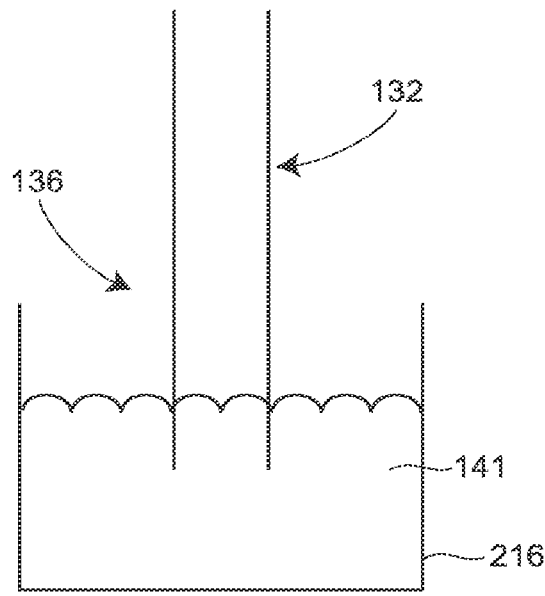
FIGS. 21A-21C are schematic illustrations of collection of the sample at the outlet of the flow cell after detection, in accordance with embodiments of the disclosure.

After the sample has passed through the interrogation region 148 for illumination and detection and through the sorting region 152 for optional sorting, the sample flows to the outlet 136 of the flow cell 132 and may be collected in an open or closed container at the outlet of the flow cell. FIG. 21A illustrates and example of collection in an open container 218.

Figure 21B:
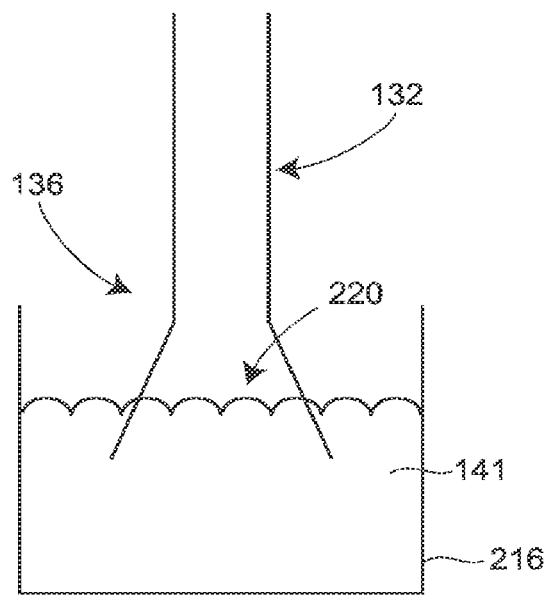

In some embodiments, the outlet 136 end of the flow cell 132 may have an enlarged diameter to allow for collection of the sample 141 with reduced pressure and/or velocity. FIG. 21B illustrates an example of collection through a region 220 of the flow cell 132 having an enlarged diameter resulting in a region of reduced pressure and/or velocity. The sample 141 may be collected in an open or closed container (an open container 218 is exemplified in FIG. 21B) at the outlet 136. Other means may also be used to slow the velocity of the output stream in order to minimize damage to the analyte.

Figure 21C:
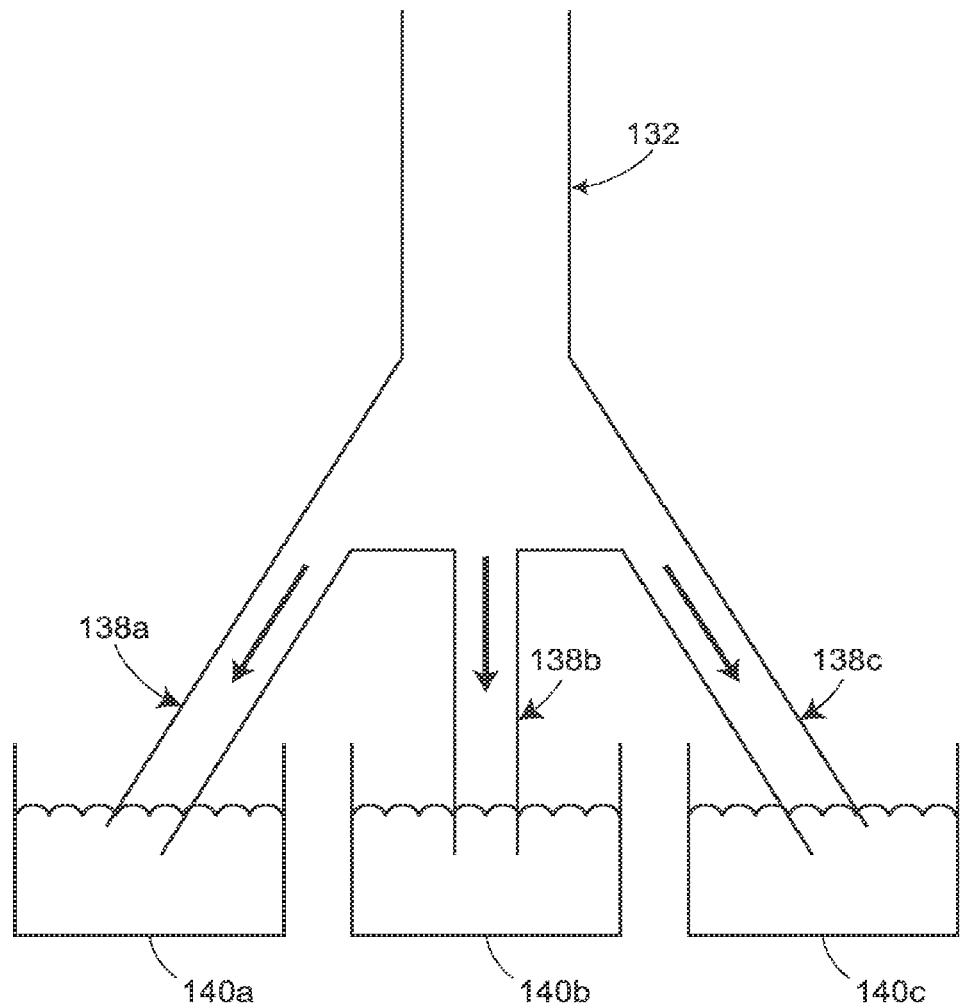

In yet other embodiments, physical sorting at the outlet 136, downstream of the sorting region 152 may be achieved by division of the flow path 138 at the outlet end into two or more flow paths. FIG. 21C illustrates, for example, an embodiment in which the flow path 138 is divided into three flow paths 138a, 138b, 138c at the outlet 136 end of the flow cell 132, downstream of the sorting region 152. The analytes 142 in the core of the fluid flow may be directed to the center flow path 138b, while the sheath fluid may be diverted to the outer flow paths 138a and 138c. Separate containers 140a, 140b, 140c may be used to collect from the flow paths 138a, 138b, 138c. The containers may be open or closed. The flow cell 132 may optionally include a component (not shown) to ensure position of the particles relative to the divided flow paths. The optional component may include, for example, optical apparatus for the detection of particles of the analyte entering the center flow path 138b. In some embodiments, variable flow rate at the outlet or region of physical separation can be used to divert the analyte and/or analyte of interest and/or modified analyte to one of the flow paths, for example, as described in U.S. Pat. No. 7,355,696, the disclosure of which is incorporated herein by reference in its entirety.

The flow cell 132 will be understood herein to be a closed flow path so long as the flow path 138 is a single, unitary and bounded flow path in the region passing through the interrogation region 148 and through the sorting region 152. Division of the flow path 138 downstream of the sorting region 152 does not affect the characterization of the flow cell 132 as being closed.

Control System

Figure 22:
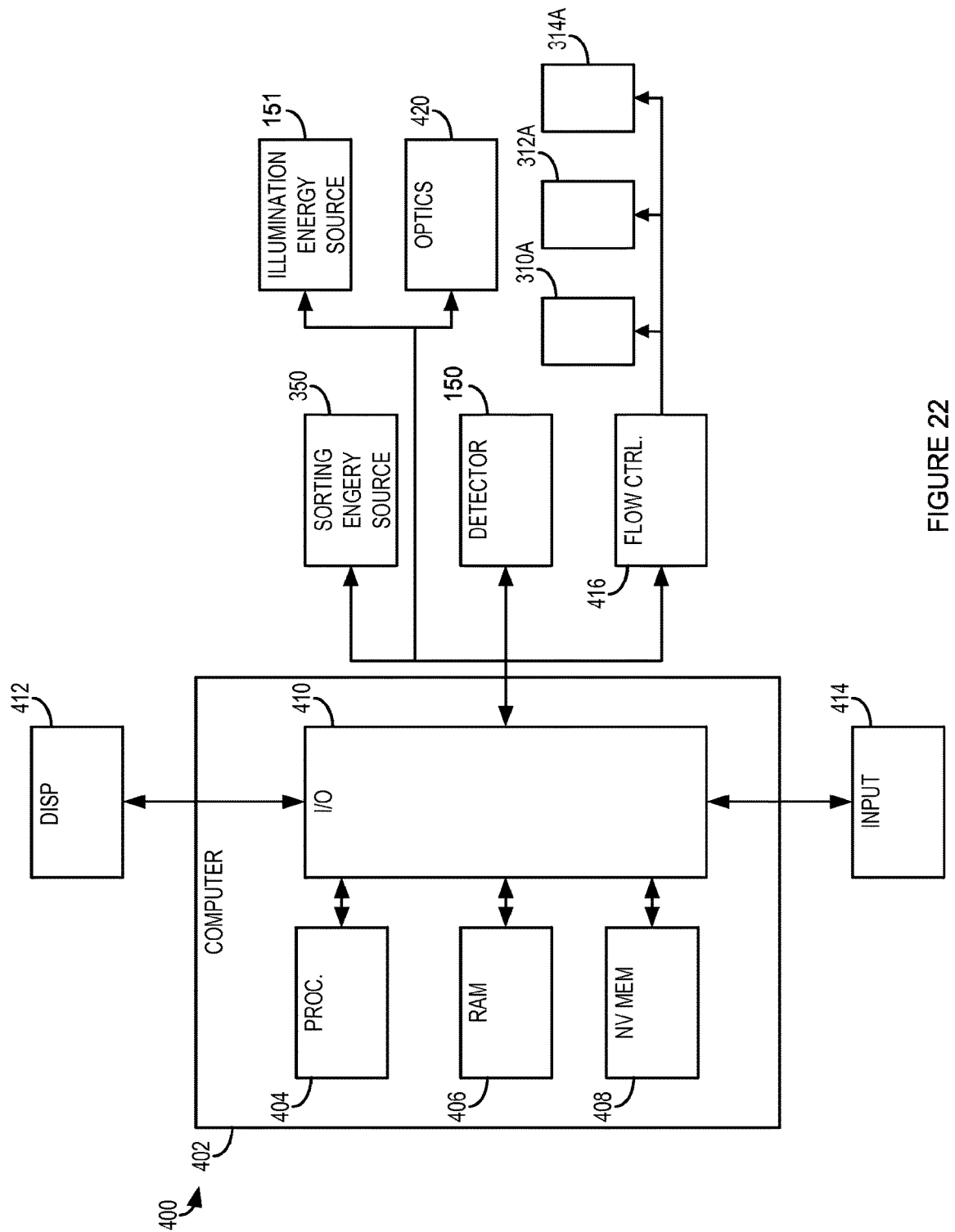
FIG. 22 is a schematic illustration of a control system for an apparatus and method in accordance with an embodiment of the disclosure.

Referring to FIG. 22, the flow cytometry system may also include a computer control system 400. The computer control system may include one or more computer devices 402, such as workstations, laptop computers, tablet computers, netbook computers, personal digital assistants, and the like. As generally known, each computer device 402 may include or have access to one or more microprocessor devices 404, one or more volatile memory devices (e.g., RAM) 406, and one or more non-volatile memory devices (e.g., hard disk drives, optical memory devices, etc.) 408. The microprocessor device 404 may store instructions and data on the volatile memory device 406 during runtime operation and, similarly, may store instructions and/or data on the non-volatile memory device 408. For example, as is generally known, instructions for one or more routines or programs may be stored in the non-volatile memory device 408 for retrieval by the microprocessor device 404. The microprocessor device 404 may, upon execution of a routine, retrieve the routine from the non-volatile memory device 408 and store a copy of the routine in the volatile memory device 406. During execution of the routine, the microprocessor device 404 may additionally store data in one or both of the volatile and non-volatile memory devices 406 and 408, respectively. Additionally, the microprocessor device 404 may receive, process, and/or store in the memory devices 406, 408 data from one or more devices external to the computer 402 as described below. One or more input/output (I/O) devices 410 may facilitate communication between the microprocessor 404 and the external devices and, additionally, between the microprocessor 404 and the memory devices 406, 408. Further, the I/O device 410 may communicate with a display device 412, which may be internal or external to the computer device 402, and may be used to display a user interface for allowing an operator to control the cytometry system. One or more input devices 414 (e.g., a mouse, a touch screen, a keyboard, etc.) may allow the user to input data or commands to the cytometry system.

The I/O device 410 may facilitate communication between the microprocessor 404 and the cytometry hardware, such as the sorting energy source, the detector 150, the illumination source 151 and the fluidic system. With respect to the fluidic system, specifically, the I/O device 410 may facilitate communication between the microprocessor 404 and a flow control subsystem 416 operating to control the flow of sheath fluid and sample fluid from the supplies of sheath fluid and sample fluid, respectively, and to the collection container. For example, the flow control subsystem 416 may control a pump 310A in fluid communication with the sheath fluid supply 310, may control a pump 312A in fluid communication with the sample fluid supply 312, and/or may control a pump 314A in fluid communication with the collection container 314. Further, the flow control subsystem 416 may include or communicate with sensors operable to sense the volume or rate of flow of the sheath fluid, of the sample fluid, of the fluid entering the collection container 140, and/or of the core-in-sheath flow formed within the flow cytometry system. Lastly, the I/O device 410 may facilitate communication between the microprocessor 404 and one or more components 420 of an optical subsystem. The components 420 may include one or more movable optical elements (e.g., mirrors or lenses) and/or one or more electrochromic devices which may be used to selectively direct, redirect, and/or block energy from the sorting energy source and/or the illumination energy source 418. Additionally, the components 420 may include one or more movable optical elements operable to calibrate, or to facilitate the calibration of: (1) the position of an optical element; (2) the direction of illumination energy, sorting energy, and/or detected energy; and/or (3) the intensity of illumination energy, sorting energy, and/or detected energy.

As will be appreciated, the computer 402 may store and execute various computer-readable instructions for implementing the one or more routines, which may include control routines, analysis routines, sorting routines, etc. and, in particular, to control the relative flow of the sheath and sample fluids, to receive and analyze data output by the detector 150, to control the illumination source, to control the sorting energy source, to control the configuration of an optical element, to analyze one or more properties of the fluid flow, etc. While the routines are described as stored on memory devices and executed by a microprocessor device, the routines may also be hardware modules. A hardware module is a tangible unit capable of performing certain operations and may be configured or arranged in certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described above.

In various embodiments, a hardware module may be implemented mechanically or electronically. For example, a hardware module may comprise dedicated circuitry or logic that is permanently configured (e.g., as a special-purpose processor, such as a field-programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

An Exemplary Method of Sorting Spermatozoa

Figure 23:
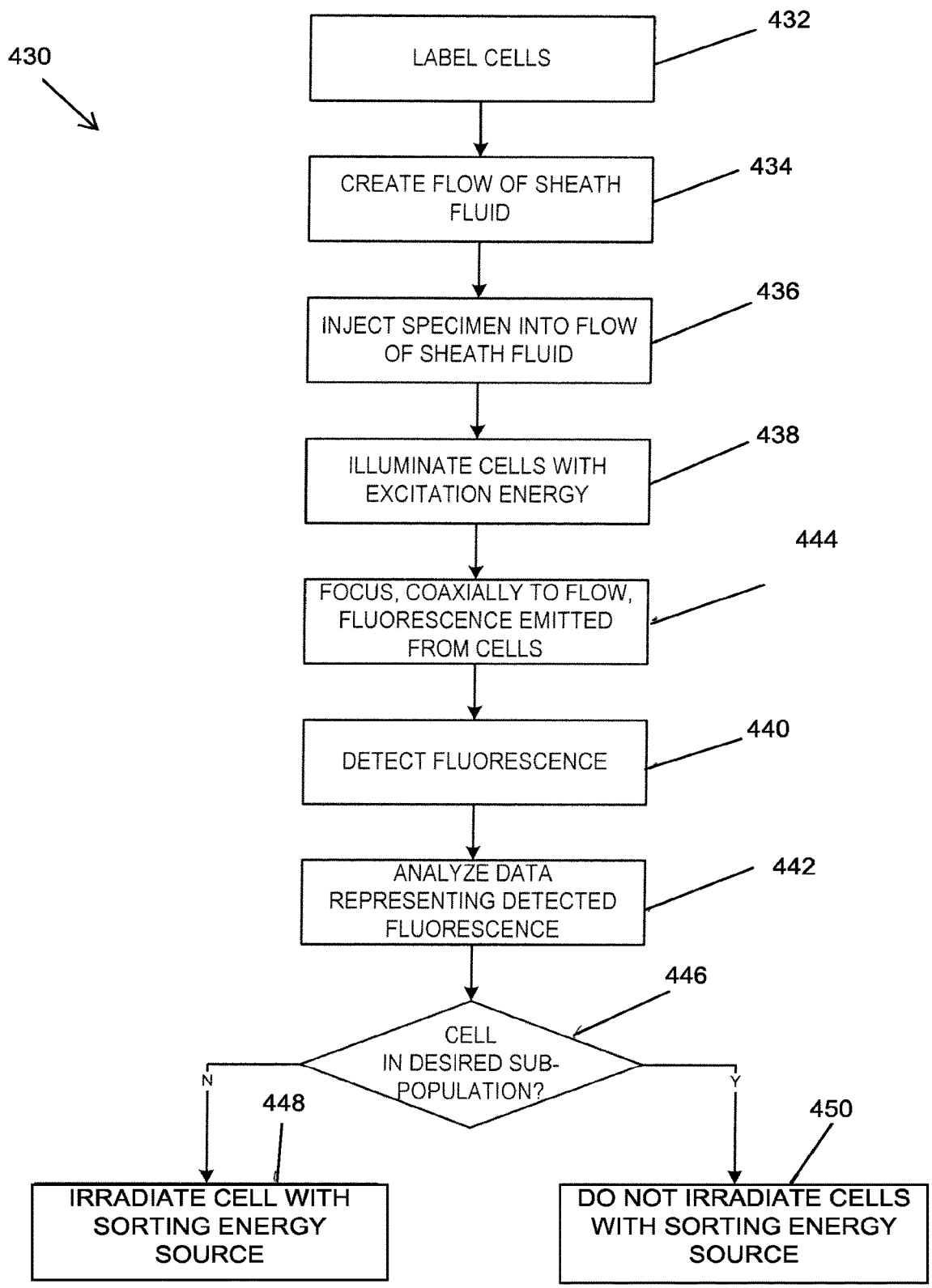
FIG. 23 is a schematic illustration of an exemplary method of detecting and sorting an analyte in accordance with an embodiment of the disclosure.

FIG. 23 illustrates an exemplary embodiment of the methods described herein and, in particular, a method 430 of selecting a desired sub-population of cells from a sample of cells (e.g., selecting X or Y chromosome-bearing cells from a sample containing a mixture of X and Y chromosome-bearing cells). In some embodiments, the method 430, or portions thereof, is stored in one of the memories 406, 408 as a set of machine-readable instructions making up a control routine for one or more associated apparatus. The processor 404 may read the instructions from the memory 406, 408 and execute the instructions to perform the method 430. In another embodiment, the method 430 includes several routines. The routines may individually control one or more apparatus, may analyze data collected by the one or more apparatus, and/or may make one or more determinations based on the analyzed data, etc. As generally known, a technician or apparatus may label (e.g., by applying a Hoechst stain) a specimen for analysis (e.g., a collection of sperm cells) (block 432). Labeling the cells may be accomplished within a sorting flow cytometer, or in a separate process or procedure outside of the sorting flow cytometer. Moreover, the particular label applied to the cells may depend upon the cytometric application. In some embodiments, the parameters of the labeling process may be determined by the processor 404 and/or the labeling process, or a portion thereof, may controlled by the processor 404. The cells can be labeled, for example, such that the cells and/or the labeling component generates a detectable signal in response to illumination.

In any event, after labeling the cells, an apparatus in accordance with the present description and, in particular, a sorting flow cytometer, may create a flow of sheath fluid in the flow path 138 (block 434). Through a separate input, the sorting flow cytometer may inject a specimen (i.e., the labeled cells in a suitable liquid) into the flow path 138 (block 436), preferably at or near the center of the flow of sheath fluid. Also preferably, the specimen enters the flow of sheath fluid slowly relative to the flow of sheath fluid, such that the cells within the specimen (e.g., the sperm cells) align with a long axis parallel to the flow of sheath fluid, and such that the cells flow in a generally single-file pattern. The flow control subsystem 416 may control the flow of sheath fluid and sample fluid from the supplies of sheath fluid and sample fluid, according to a routine executed by the processor 404, to optimize the relative flows of the sheath fluid and the sample fluid. The flow control subsystem 416 may include various sensors and/or detectors providing inputs to the routine executed on the processor 404, to facilitate optimization of the relative flows.

As the cells move through the flow path 138, an illumination energy source 151, such as a UV laser, illuminates the specimen (block 438) in the interrogation region 148. The illumination energy source may continually illuminate the interrogation region 148, or a routine executing on the processor 404 may control the illumination energy source 151 to illuminate the interrogation region 148 selectively (e.g., only when a specimen is present in the interrogation region 148). The cells and/or a component or label of or associated with the cells generates a detectable signal in response to illumination.

The concave collector element 146 operates to focus energy emitted, transmitted, or reflected from each cell (e.g., fluorescent light emitted by the label in response to the illumination) (block 440). That is, the combined sheath flow and specimen within the flow path 138 move generally along an optical axis of the concave collector element 146, which optical axis is generally coaxial with the flow and, nominally, each cell within the specimen passes through a focal point (coincident with the interrogation region 148) of the concave collector element 146. The detector 150 receives the focused energy from the concave collector element 146 (block 442), and sends a signal representative of the detected energy to the processor 404. In some embodiments, the detector 150 may detect individually the focused energy from more than 40,000 cells per second, may detect individually the focused energy from more than 75,000 cells per second, may detect individually the focused energy from more than 100,000 cells per second, may detect individually the focused energy from more than 200,000 cells per second, or may detect individually the focused energy from more than 300,000 cells per second.

The processor 404 receives the signal representative of the detected energy and analyzes the data (block 444) to determine (at block 446) whether the data represent a cell within the desired sub-population or a cell not within the desired sub-population. In some embodiments, the processor 404 may also determine whether the data represent an indeterminate cell, which can neither be determined to be in the desired sub-population nor be determined not to be in the desired sub-population. In the latter case, the processor 404 may treat the cell as though the detector 150 determined that the cell was not in the desired sub-population. If the processor 404 determines that the cell is not in the desired sub-population or is indeterminate, the processor 404 may send a signal to the sorting energy source 350, such as an infrared laser, to irradiate the cell (e.g., to alter the cell, destroy the cell, render the cell non-viable, etc.) (block 448) at a suitable time once the cell has passed from the interrogation region 148 to the sorting region 152; the sorting energy source being focused on the sorting region 152. Alternatively, if the processor 404 determines that the cell is in the desired sub-population, the processor 404 may send a signal to the sorting energy source 350 (or refrain from sending a signal) such that the sorting energy source 350 does not irradiate the cell (block 450) when the cell passes through the sorting region 152. The sorting energy source may be configured such that it either delivers energy to the specimen or does not deliver energy to the specimen during the time periods when desired or undesired cells are expected to be present in the sorting region 152. In other words, the sorting energy source 350 may either deliver energy or not deliver energy to the specimen by default, and may be signaled by the processor 404 to change its state of delivering or not delivering energy at an appropriate time as determined by the processor 404. Of course, it will be understood that, instead of or in addition to controlling a signal to the sorting energy source 350, the modulation and/or attenuation of the sorting energy provided by the sorting energy source 350 may be accomplished by controlling the optics 420, which may include attenuators, movable optical elements, and the like.

The apparatus may collect the cells for use and/or further processing (e.g., separating the cells) at the end of the process. In some embodiments, which may include the embodiment depicted in FIG. 15, the processor 404 sends a signal to the sorting energy source 350 and/or to the optics 420 to leave unaltered (i.e., not to irradiate) cells determined to be in the desired sub-population, and the resulting collection of processed cells comprises a ratio of cells in the desired sub-population of cells to total unaltered cells greater than or equal to 60%. Further, in some embodiments, which may include the embodiment depicted in FIG. 15, the processor 404 sends a signal to the sorting energy source 350 and/or to the optics 420 to leave unaltered (i.e., not to irradiate) cells determined to be in the desired sub-population, and the resulting collection of processed cells comprises a ratio of altered cells in the desired sub-population to total cells in the desired sub-population less than or equal to 50%.

Of course, the method described above reflects one or more embodiments of the presently described methods, but may also encompass one or more additional steps or routines, as described throughout this specification with respect to various embodiments. Moreover, some embodiments may omit one or more of the steps or routines described with reference to method 430. By way of example and not limitation, in some embodiments, the cell or a component of the cell may emit a detectable signal intrinsically, for example by phosphorescence or chemiluminescence, thereby eliminating the need to label the specimen with a label for generating the detectable response. Further, in some embodiments (as described above), the method may reverse blocks 448 and 450, allowing cells determined not to be in the desired sub-population to pass without irradiation by the controllable energy source, while causing the controllable energy source to irradiate cells determined to be in the desired sub-population.

First Exemplary System Embodiment

Figure 24:
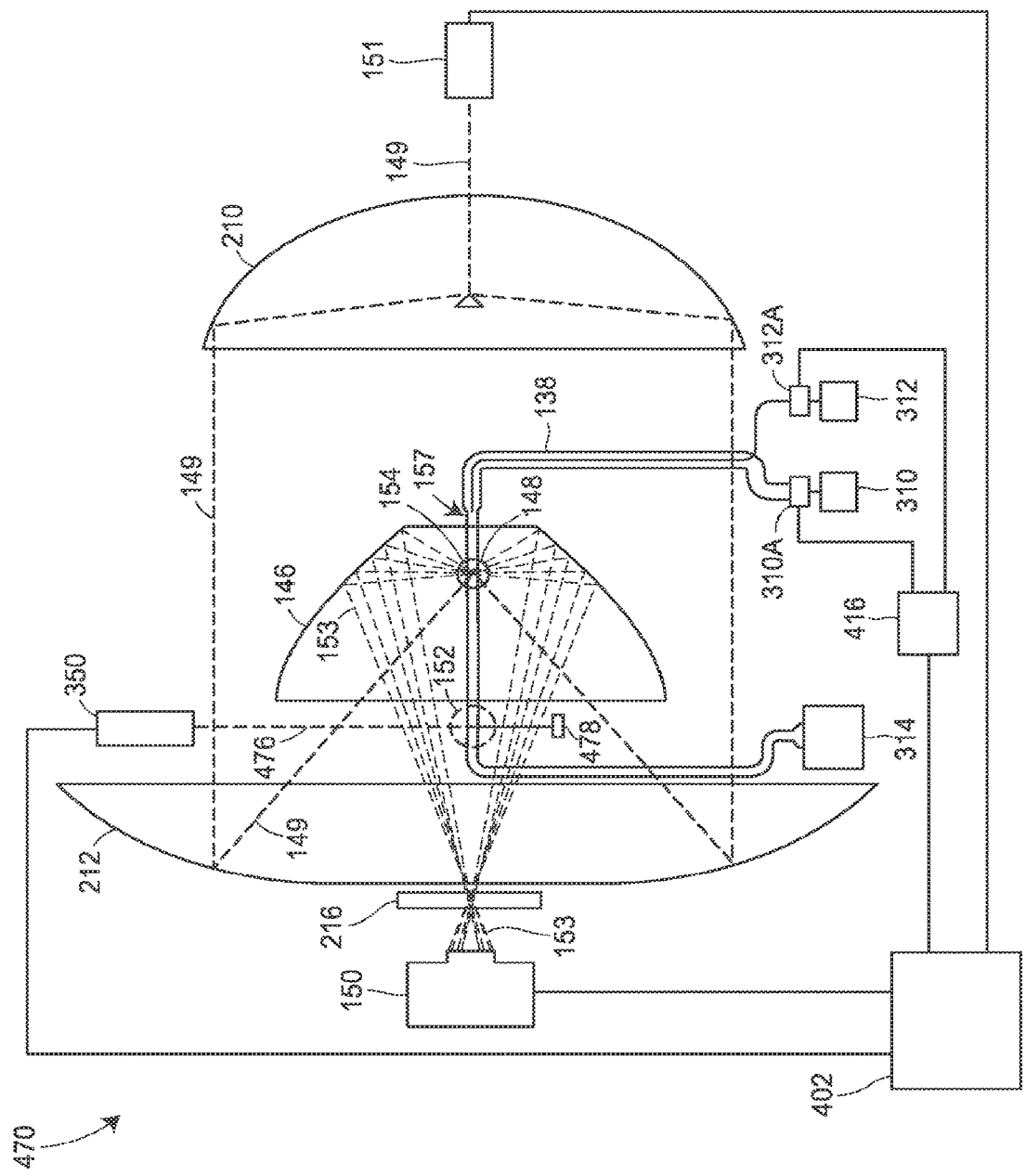
FIG. 24 is a schematic illustration of an exemplary system for detection of an analyte in accordance with an embodiment of the disclosure.

FIG. 24 depicts a first exemplary embodiment of a system 470 for performing flow cytometry. The computer 402, as described above, controls the system 470. The computer 402 receives sensor signals and other information from the flow control subsystem 416, and sends control signals back to the flow control subsystem 416. The flow control subsystem 416 operates in accordance with the signals received from the computer 402 to control the pump 310A pumping sheath fluid from the sheath fluid supply 310 and to control the pump 312A pumping sample fluid from the sample fluid supply 312. As a result, a flow is created along a flow path 138. The flow path 138 includes a hydrodynamic focusing element 157 that operates to create a core-in-sheath flow. A routine executed by the processor 404 of the computer 402 causes the computer 402 to provide signals to the flow control subsystem 416 such that the flow control subsystem 416 maintains and/or adjusts the flows of sheath fluid and sample fluid to maintain a stable flow and to optimize the spacing of the analyte particles within the core-in-sheath flow.

The computer 402 is also communicatively coupled to the illumination energy source 151, providing one or more control signals for selectively energizing the illumination energy source 151 and/or determining a power setting of the illumination energy source 151. Illumination energy 149 is projected from the illumination energy source 151 through an opening in the first parabolic optical element 210. The illumination energy 149 falls incident on the conical optical element 210, which redirects the illumination energy 149 toward the surface of the first parabolic optical element 210. The first parabolic optical element 210 reflects the illumination energy 149 as an annulus to the second parabolic optical element 212. As the annulus of illumination energy 149 falls incident on the second parabolic optical element 212, the illumination energy 149 is reflected (having a generally conical shape) toward the focal point of the second parabolic optical element 212, which focal point is coincident with the interrogation region 148 in the flow path 138. The spherical molding 154 integrally formed in the flow cell at the interrogation region 148 ensures that the illumination energy 149 remains focused as it falls incident on the analyte.

As the illumination energy 149 falls incident on the analyte, it causes the analyte to emit the detectable signal 153 in the form of fluorescence. The spherical molding 154 integrally formed in the flow cell at the interrogation region 148 minimizes refraction of the detectable signal 153 as it leaves the flow cell. The detectable signal 153 falls incident on the ellipsoidal collector element 146, which has a first focal point coincident with the interrogation region 148 in the flow path 138. The ellipsoidal collector element 146 reflects the detectable signal 153 toward the second focal point of the ellipsoidal collector element 146, which second focal point corresponds to the location of the pinhole 216. The detectable signal 153 passes through the pin hole and falls incident on the detector 150.

The detector 150, communicatively coupled to the computer 402, sends to the computer 402 a signal corresponding to the detectable signal 153. The computer 402 executes a routine operable to receive the signal from the detector 150, and to determine from the detector whether the analyte from which the detectable signal 153 was emitted is in a desired sub-population or not in the desired sub-population.

The computer 402 is further communicatively coupled to the sorting energy source 350. The computer 402 sends a signal to the sorting energy source 350 to selectively energize the sorting energy source 350 at a time when the analyte from which the detectable signal 153 was emitted will be in a sorting region 152, which is disposed in the path of electromagnetic radiation 476 emitted by the sorting energy source 350. The computer 402 causes the sorting energy source 350 to emit electromagnetic radiation 476 when the analyte is not in the desired sub-population, and causes the sorting energy source 350 not to emit electromagnetic radiation 476 when the analyte is in the desired sub-population. A routine executing on the computer 402 may determine when the analyte will be in the sorting region 152 according to known parameters of the flow, which are, in any event, also controlled by the computer 402 via the flow control subsystem 416. A beam stop 478 prevents the electromagnetic radiation 476 from falling incident on other parts of the system 470.

The collection container 314 collects the fluid containing the sorted sample at the end of the flow path 138.

As FIG. 24 depicts, the flow cell 132 is remains closed (i.e., the core-in-sheath flow is not exposed to the atmosphere) and uninterrupted (i.e., the core-in-sheath flow does not bifurcate) at least from before it passes through the interrogation region 148 to after it passes through the sorting region 152. Additionally, the flow axis of the flow path 138 as it passes through the interrogation region 148 is coaxial with the optical axis of the ellipsoidal collector element 146, is coaxial with the optical axis of the second parabolic optical element 212, and is coaxial with the optical axis of the first parabolic optical element 210.

Second Exemplary System Embodiment

Figure 25:
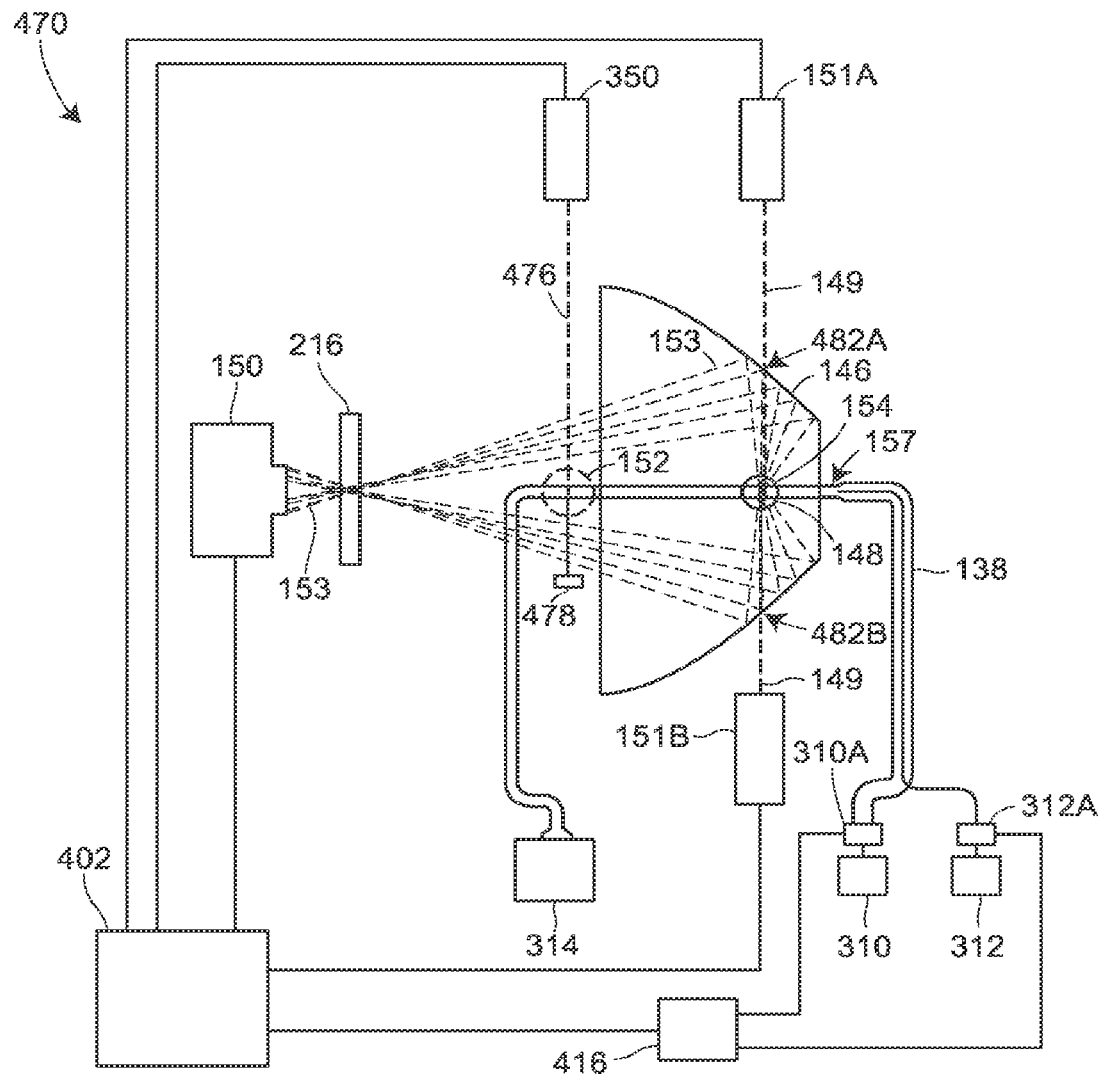
FIG. 25 is a schematic illustration of an exemplary system for detection of an analyte in accordance with another embodiment of the disclosure.

FIG. 25 depicts a second exemplary embodiment of a system 480 for performing flow cytometry. The computer 402, as described above, controls the system 480. The computer 402 receives sensor signals and other information from the flow control subsystem 416, and sends control signals back to the flow control subsystem 416. The flow control subsystem 416 operates in accordance with the signals received from the computer 402 to control the pump 310A pumping sheath fluid from the sheath fluid supply 310 and to control the pump 312A pumping sample fluid from the sample fluid supply 312. As a result, a flow is created along a flow path 138. The flow path 138 includes a hydrodynamic focusing element 157 that operates to create a core-in-sheath flow. A routine executed by the processor 404 of the computer 402 causes the computer 402 to provide signals to the flow control subsystem 416 such that the flow control subsystem 416 maintains and/or adjusts the flows of sheath fluid and sample fluid to maintain a stable flow and to optimize the spacing of the analyte particles within the core-in-sheath flow.

The computer 402 is also communicatively coupled to the illumination energy sources 151A and 151B, providing to each one or more control signals for selectively energizing the illumination energy source 151A, 151B and/or determining a power setting of the illumination energy source 151A, 151B. Illumination energy 149 is projected from each of the illumination energy sources 151A, 151B through a respective opening 482A, 482B in the ellipsoidal collector element 146. The illumination energy 149 is directed toward the interrogation region 148 in the flow path 138. The spherical molding 154 integrally formed in the flow cell at the interrogation region 148 ensures that the illumination energy 149 is not refracted as it falls incident on the analyte.

As the illumination energy 149 falls incident on an analyte within the interrogation region 148, it causes the analyte to emit the detectable signal 153 in the form of fluorescence. The spherical molding 154 integrally formed in the flow cell at the interrogation region 148 minimizes refraction of the detectable signal 153 as it leaves the flow cell. The detectable signal 153 falls incident on the ellipsoidal collector element 146, which has a first focal point coincident with the interrogation region 148 in the flow path 138. The ellipsoidal collector element 146 reflects the detectable signal 153 toward the second focal point of the ellipsoidal collector element 146, which second focal point corresponds to the location of the pinhole 216. The detectable signal 153 passes through the pin-hole 216 and then falls incident on the detector 150.

The detector 150, communicatively coupled to the computer 402, sends to the computer 402 a signal corresponding to the detectable signal 153. The computer 402 executes a routine operable to receive the signal from the detector 150, and to determine from the detector whether the analyte from which the detectable signal 153 was emitted is in a desired sub-population or not in the desired sub-population.

The computer 402 is further communicatively coupled to the sorting energy source 350. The computer 402 sends a signal to the sorting energy source 350 to selectively energize the sorting energy source 350 at a time when the analyte from which the detectable signal 153 was emitted will be in a sorting region 152, which is disposed in the path of electromagnetic radiation 476 emitted by the sorting energy source 350. The computer 402 causes the sorting energy source 350 to emit electromagnetic radiation 476 when the analyte is not in the desired sub-population, and causes the sorting energy source 350 not to emit electromagnetic radiation 476 when the analyte is in the desired sub-population. A routine executing on the computer 402 may determine when the analyte will be in sorting region 152 according to known parameters of the flow, which are, in any event, also controlled by the computer 402 via the flow control subsystem 416. A beam stop 478 prevents the electromagnetic radiation 476 from falling incident on other parts of the system 470.

The collection container 314 collects the fluid containing the sorted sample at the end of the flow path 138.

As FIG. 25 depicts, the flow cell 132 is remains closed (i.e., the core-in-sheath flow is not exposed to the atmosphere) and uninterrupted (i.e., the core-in-sheath flow does not bifurcate) at least from before it passes through the interrogation region 148 to after it passes through the sorting region 152. Additionally, the flow axis of the flow path 138 as it passes through the interrogation region 148 is coaxial with the optical axis of the ellipsoidal collector element 146.

Third Exemplary Embodiment

FIG. 26 depicts a third exemplary embodiment of a system 580 for performing flow cytometry. The computer 502, as described above, controls the system 580. The computer 502 receives sensor signals and other information from the flow control subsystem 516, and sends control signals back to the flow control subsystem 516. The flow control subsystem 516 operates in accordance with the signals received from the computer 502 to control the pump 310A pumping sheath fluid from the sheath fluid supply 310 and to control the pump 312A pumping sample fluid from the sample fluid supply 312. As shown in FIG. 26, an objective lens 517 of the flow cytometer can be modified to allow the sample fluid 141 to pass through the lens 517 and be pumped into the sheath fluid as a core fluid. In particular, the sample 141 is directed to enter through the center of the sheath flow 200 through an orifice or chamber disposed in the sheath fluid flow path. Both flows enter the acceleration region 204 and establish a stable core-in-sheath flow. A routine executed by the processor 504 of the computer 502 causes the computer 502 to provide signals to the flow control subsystem 516 such that the flow control subsystem 516 maintains and/or adjusts the flows of sheath fluid and sample fluid to maintain a stable flow and to optimize the spacing of the analyte particles within the core-in-sheath flow.

The computer 502 is also communicatively coupled to the illumination energy source 151, providing one or more control signals for selectively energizing the illumination energy source 151 and/or determining a power setting of the illumination energy source 151. The illumination energy 149 is directed toward the interrogation region 148 in the flow path 138.

As the illumination energy 149 falls incident on an analyte within the interrogation region 148, it causes the analyte to emit the detectable signal 153 in the form of fluorescence. The detectable signal 153 falls incident on the objective lens 517, which has a first focal point coincident with the interrogation region 148 in the flow path 138. The objective lens 517 reflects the detectable signal 153 toward a second lens 519, which focuses the detectable signal 153 onto the detector, located at the focal point of the second lens 519.

The detector 150, communicatively coupled to the computer 502, sends to the computer 502 a signal corresponding to the detectable signal 153. The computer 502 executes a routine operable to receive the signal from the detector 150, and to determine from the detector 150 whether the analyte from which the detectable signal 153 was emitted is in a desired sub-population or not in the desired sub-population.

The computer 502 is further communicatively coupled to the sorting energy source 350. The computer 402 sends a signal to the sorting energy source 350 to selectively energize the sorting energy source 350 at a time when the analyte from which the detectable signal 153 was emitted will be in a sorting region 152, which is disposed in the path of electromagnetic radiation 576 emitted by the sorting energy source 350. The computer 502 causes the sorting energy source 350 to emit electromagnetic radiation 576 when the analyte is not in the desired sub-population, and causes the sorting energy source 350 not to emit electromagnetic radiation 576 when the analyte is in the desired sub-population. A routine executing on the computer 502 may determine when the analyte will be in sorting region 152 according to known parameters of the flow, which are, in any event, also controlled by the computer 502 via the flow control subsystem 516. A beam stop 478 prevents the electromagnetic radiation 576 from falling incident on other parts of the system 570.

The collection container 314 collects the fluid containing the sorted sample at the end of the flow path 138.

As FIG. 26 depicts, the flow cell 132 remains closed (i.e., the core-in-sheath flow is not exposed to the atmosphere) and uninterrupted (i.e., the core-in-sheath flow does not bifurcate) at least from before it passes through the interrogation region 148 to after it passes through the sorting region 152. Additionally, the flow axis of the flow path 138 as it passes through the interrogation region 148 is coaxial with the optical axis of the objective lens 517.

In any of the embodiments described herein, the flow cytometry system may also include a computer control system as described generally in 170-173. Specifically, the computer control system may communicate with one of, any combination of, or all of the sorting energy source, the detector, the illumination source and the fluidic system. With respect to the fluidic system, specifically, the computer control system may control a flow control subsystem operating to control the flow of sheath fluid and/or sample fluid from the supplies of sheath fluid and sample fluid, respectively, and to the collection container, as described above. Lastly, the computer control system my control various components of an optical subsystem that may include one or more movable optical elements (e.g., mirrors or lenses) and/or one or more electrochromic devices which may be used to selectively direct, redirect, and/or block energy from the sorting energy source and/or the illumination energy source, and may include one or more movable optical elements operable to calibrate, or to facilitate the calibration of: (1) the position of an optical element; (2) the direction of illumination energy, sorting energy, and/or detected energy; and/or (3) the intensity of illumination energy, sorting energy, and/or detected energy.

What is claimed:

1. An apparatus for identifying analytes of a first type in a fluid sample comprising analytes of a plurality of types, the apparatus comprising:
   a closed flow cell comprising:
      a sample inlet;
      a sample outlet;
      a flow path defined between the sample inlet and sample outlet, the flow path passing through an interrogation region, wherein at least the portion of the flow path extending from immediately upstream of the interrogation region to immediately downstream of the interrogation region is bounded by a flow cell wall to form a continuous closed flow path, without division or bifurcation;
   a spherical molding surrounding the flow path and having a center point coincident with the interrogation region such that electromagnetic energy propagating from the interrogation region to an exterior surface of the spherical molding intersects the exterior surface at an angle orthogonal to the exterior surface;
   a hydrodynamic focusing element upstream of the interrogation region and fluidically coupled with the flow path of the flow cell and creating a core-in-sheath flow along a flow axis of the flow path as it passes through the interrogation region, the core-in-sheath flow comprising a core flow carrying the analytes, the hydrodynamic focusing element comprising (i) an outer flow path configured for fluidic coupling to a source of sheath fluid and having a sheath fluid flow axis and (ii) an inner flow path, disposed within the outer flow path, configured for fluidic coupling to a source of the fluid sample, wherein the sample flow axis is generally coaxial with the sheath fluid flow axis, and (iii) a wall surrounding the inner flow path upstream of the interrogation region;
   a concave, ellipsoidal collector element comprising a vertex, an optical axis, a first focal point disposed in the interrogation region of the flow path, a second focal point, and a reflective surface disposed in an optical path between the first focal point and the second focal point, such that the reflective surface directs a signal from the analyte in the interrogation region to the second focal point;
   illumination means comprising a plurality of beams of electromagnetic energy converging non-axisymmetrically at the interrogation region, each of the plurality of beams orthogonal to the flow axis.

2. An apparatus according to claim 1, wherein the spherical molding, or a portion thereof, is formed of a material having an index of refraction that is within 0.1 greater than or less than an index of refraction of the flow cell wall.

3. An apparatus according to claim 1, wherein the flow path is divided downstream of a sorting region of the flow path, and configured to separate all or part of the core flow from the sheath flow downstream of the interrogation region.

4. An apparatus according to claim 1, wherein the flow path comprises, at an end proximal to the sample outlet, an enlarged diameter to reduce the velocity of the fluid sample.

5. An apparatus according to claim 1, further comprising a source of direct, destructive radiation, configured to deliver the radiation to a point in the flow path between the interrogation region and the sample outlet.

6. An apparatus according to claim 5, wherein the source of direct, destructive radiation comprises a pulsed laser.

7. An apparatus according to claim 1, wherein the hydrodynamic focusing element is configured to keep an energy dissipation rate (EDR) below a predetermined threshold, the EDR calculated according to the equation $\varepsilon = \mu(\nabla U + \nabla U T) := U$, wherein $\varepsilon$ is the EDR, $\mu$ is the viscosity, $(\nabla U + \nabla U T)$ is the stress tensor, $\nabla U$ is the velocity gradient tensor, and $\nabla U T$ is the transpose of $\nabla U$.

8. An apparatus according to claim 1, wherein the wall surrounding the inner flow path of the hydrodynamic focusing element has an outer surface tapered at an end disposed toward a point of convergence of the inner and outer flow paths.

9. An apparatus according to claim 1, wherein the optical axis of the ellipsoidal collector element is coaxial with the flow path as the flow path passes through the interrogation region.

* * * * *